(12) United States Patent
Catanese, III et al.

(10) Patent No.: US 8,211,118 B2
(45) Date of Patent: Jul. 3, 2012

(54) APPARATUS AND METHOD FOR MANIPULATING OR RETRACTING TISSUE AND ANATOMICAL STRUCTURE

(75) Inventors: Joseph Catanese, III, San Leandro, CA (US); Theodore C. Lamson, Pleasanton, CA (US); Joshua Makower, Los Altos, CA (US); Amik Nagpurkar, Toronto (CA); Daniel Merrick, Dublin, CA (US); Jacqueline Nerney Welch, Pacifica, CA (US); Richard G. Vecchiotti, Stanford, CA (US); Scott West, Livermore, CA (US); Claude Vidal, Santa Barbara, CA (US); Russell J. Redmond, Goleta, CA (US); Michael Collinson, Gelta, CA (US)

(73) Assignee: Neotract, Inc., Pleasanton, CA (US)

( * ) Notice: Subject to any disclaimer, the term of this patent is extended or adjusted under 35 U.S.C. 154(b) by 59 days.

(21) Appl. No.: 12/986,890

(22) Filed: Jan. 7, 2011

(65) Prior Publication Data

US 2011/0152607 A1 Jun. 23, 2011

Related U.S. Application Data

(60) Division of application No. 11/492,690, filed on Jul. 24, 2006, now Pat. No. 7,896,891, which is a continuation-in-part of application No. 11/318,246, filed on Dec. 22, 2005, now Pat. No. 7,645,286, which is a continuation-in-part of application No. 11/134,870, filed on May 20, 2005, now Pat. No. 7,758,594.

(51) Int. Cl.
 *A61B 17/10* (2006.01)

(52) U.S. Cl. ..................... 606/139; 606/151
(58) Field of Classification Search ............... 606/99, 606/139, 151, 213, 232; 604/27; 623/17.16
See application file for complete search history.

(56) References Cited

U.S. PATENT DOCUMENTS

| | | | |
|---|---|---|---|
| 659,422 | A | 10/1900 | Shidler |
| 780,392 | A | 1/1905 | Wanamaker et al. |
| 789,467 | A | 5/1905 | West |
| 2,579,192 | A | 12/1951 | Kohl |
| 2,646,298 | A | 7/1953 | Leary |
| 2,697,624 | A | 12/1954 | Thomas et al. |
| 2,734,299 | A | 2/1956 | Masson |
| 2,825,592 | A | 3/1958 | Semple |

(Continued)

FOREIGN PATENT DOCUMENTS

DE 10159470 6/2003

(Continued)

OTHER PUBLICATIONS

Richard Berges et al., "Alternative Minimalinvasive Therapien Beim Benignen Prostatasyndrom", Medizin, Jg. 104, Heft 37, Sep. 14, 2007, cited by other.

(Continued)

*Primary Examiner* — Corrine M McDermott
*Assistant Examiner* — Gregory Anderson
(74) *Attorney, Agent, or Firm* — Steptoe & Johnson LLP

(57) ABSTRACT

Integrated systems and associated method for manipulating tissues and anatomical or other structures in medical applications for the purpose of treating diseases or disorders or other purposes. In one aspect, the system includes a delivery device configured to deploy and implant anchoring devices for such purposes.

9 Claims, 47 Drawing Sheets

U.S. PATENT DOCUMENTS

| | | | |
|---|---|---|---|
| 3,326,586 A | 6/1967 | Frost et al. | |
| 3,470,834 A | 10/1969 | Bone | |
| 3,521,918 A | 7/1970 | Hammond | |
| 3,664,345 A | 5/1972 | Dabbs et al. | |
| 3,713,680 A | 1/1973 | Pagano | |
| 3,716,058 A | 2/1973 | Tanner, Jr. | |
| 3,756,638 A | 9/1973 | Stockberger | |
| 3,873,140 A | 3/1975 | Bloch | |
| 3,875,648 A | 4/1975 | Bone | |
| 3,931,667 A | 1/1976 | Merser et al. | |
| 3,976,079 A | 8/1976 | Samuels et al. | |
| 4,006,747 A | 2/1977 | Kronenthal et al. | |
| 4,210,148 A | 7/1980 | Stivala | |
| 4,235,238 A | 11/1980 | Ogiu et al. | |
| 4,291,698 A | 9/1981 | Fuchs et al. | |
| 4,409,974 A | 10/1983 | Freedland | |
| 4,493,323 A | 1/1985 | Albright et al. | |
| 4,513,746 A | 4/1985 | Aranyi | |
| 4,621,640 A | 11/1986 | Mulhollan et al. | |
| 4,657,461 A | 4/1987 | Smith | |
| 4,669,473 A | 6/1987 | Richards et al. | |
| 4,705,040 A | 11/1987 | Mueller et al. | |
| 4,714,281 A | 12/1987 | Peck | |
| 4,738,255 A | 4/1988 | Goble et al. | |
| 4,741,330 A | 5/1988 | Hayhurst | |
| 4,744,364 A | 5/1988 | Kensey | |
| 4,750,492 A * | 6/1988 | Jacobs | 606/230 |
| 4,762,128 A | 8/1988 | Rosenbluth | |
| 4,823,794 A | 4/1989 | Pierce | |
| 4,899,743 A | 2/1990 | Nicholson et al. | |
| 4,926,860 A | 5/1990 | Stice et al. | |
| 4,946,468 A | 8/1990 | Li | |
| 4,955,913 A | 9/1990 | Robinson | |
| 4,968,315 A | 11/1990 | Gatturna | |
| 5,002,550 A | 3/1991 | Li | |
| 5,041,129 A | 8/1991 | Hayhurst et al. | |
| 5,046,513 A | 9/1991 | Gatturna et al. | |
| 5,053,046 A | 10/1991 | Janese | |
| 5,080,660 A | 1/1992 | Buelna | |
| 5,100,421 A | 3/1992 | Christoudias | |
| 5,123,914 A | 6/1992 | Cope | |
| 5,129,912 A | 7/1992 | Noda et al. | |
| 5,192,303 A | 3/1993 | Gatturna et al. | |
| 5,203,787 A | 4/1993 | Noblitt et al. | |
| 5,207,672 A | 5/1993 | Roth et al. | |
| 5,217,470 A | 6/1993 | Weston | |
| 5,217,486 A | 6/1993 | Rice et al. | |
| 5,234,454 A | 8/1993 | Bangs | |
| 5,236,445 A | 8/1993 | Hayhurst et al. | |
| 5,258,015 A | 11/1993 | Li et al. | |
| 5,267,960 A | 12/1993 | Hayman et al. | |
| 5,269,809 A | 12/1993 | Hayhurst et al. | |
| 5,322,501 A | 6/1994 | Mahmud-Durrani | |
| 5,330,488 A | 7/1994 | Goldrath | |
| 5,334,200 A | 8/1994 | Johnson | |
| 5,336,240 A | 8/1994 | Metzler et al. | |
| 5,354,271 A | 10/1994 | Voda | |
| 5,358,511 A | 10/1994 | Gatturna et al. | |
| 5,364,408 A | 11/1994 | Gordon | |
| 5,366,490 A | 11/1994 | Edwards et al. | |
| 5,368,599 A | 11/1994 | Hirsch et al. | |
| 5,370,646 A | 12/1994 | Reese et al. | |
| 5,380,334 A | 1/1995 | Torrie et al. | |
| 5,391,182 A | 2/1995 | Chin | |
| 5,403,348 A | 4/1995 | Bonutti | |
| 5,405,352 A | 4/1995 | Weston | |
| 5,411,520 A | 5/1995 | Nash et al. | |
| 5,417,691 A | 5/1995 | Hayhurst | |
| 5,435,805 A | 7/1995 | Edwards et al. | |
| 5,470,337 A | 11/1995 | Moss | |
| 5,472,446 A | 12/1995 | de la Torre | |
| 5,480,406 A | 1/1996 | Nolan et al. | |
| 5,499,994 A | 3/1996 | Tihon et al. | |
| 5,501,690 A | 3/1996 | Measamer et al. | |
| 5,507,754 A | 4/1996 | Green et al. | |
| 5,522,846 A | 6/1996 | Bonutti | |
| 5,531,763 A | 7/1996 | Mastri et al. | |
| 5,536,240 A | 7/1996 | Edwards et al. | |
| 5,540,704 A | 7/1996 | Gordon et al. | |
| 5,545,171 A | 8/1996 | Sharkey et al. | |
| 5,545,178 A | 8/1996 | Kensey et al. | |
| 5,550,172 A | 8/1996 | Regula et al. | |
| 5,554,162 A | 9/1996 | DeLange | |
| 5,554,171 A | 9/1996 | Gatturna et al. | |
| 5,562,689 A | 10/1996 | Green et al. | |
| 5,569,305 A | 10/1996 | Bonutti | |
| 5,571,104 A | 11/1996 | Li | |
| 5,573,540 A | 11/1996 | Yoon | |
| 5,578,044 A | 11/1996 | Gordon et al. | |
| 5,591,177 A | 1/1997 | Lehrer | |
| 5,593,421 A | 1/1997 | Bauer | |
| 5,611,515 A | 3/1997 | Benderev et al. | |
| 5,626,614 A | 5/1997 | Hart | |
| 5,630,824 A | 5/1997 | Hart | |
| 5,647,836 A | 7/1997 | Blake, III et al. | |
| 5,665,109 A | 9/1997 | Yoon | |
| 5,667,486 A | 9/1997 | Mikulich et al. | |
| 5,669,917 A | 9/1997 | Sauer et al. | |
| 5,690,677 A | 11/1997 | Schmieding et al. | |
| 5,697,950 A | 12/1997 | Fucci et al. | |
| 5,707,394 A | 1/1998 | Miller et al. | |
| 5,716,368 A | 2/1998 | de la Torre et al. | |
| 5,718,717 A | 2/1998 | Bonutti | |
| 5,725,556 A | 3/1998 | Moser et al. | |
| 5,725,557 A | 3/1998 | Gatturna et al. | |
| 5,733,306 A | 3/1998 | Bonutti | |
| 5,741,276 A | 4/1998 | Poloyko et al. | |
| 5,746,753 A | 5/1998 | Sullivan et al. | |
| 5,749,846 A | 5/1998 | Edwards et al. | |
| 5,752,963 A | 5/1998 | Allard et al. | |
| 5,782,862 A | 7/1998 | Bonutti | |
| 5,782,864 A | 7/1998 | Lizardi | |
| 5,800,445 A | 9/1998 | Ratcliff et al. | |
| 5,807,403 A | 9/1998 | Beyar et al. | |
| 5,810,848 A | 9/1998 | Hayhurst | |
| 5,814,072 A | 9/1998 | Bonutti | |
| 5,830,179 A | 11/1998 | Mikus et al. | |
| 5,830,221 A | 11/1998 | Stein | |
| 5,845,645 A | 12/1998 | Bonutti | |
| 5,846,254 A | 12/1998 | Schulze et al. | |
| 5,861,002 A | 1/1999 | Desai | |
| 5,868,762 A | 2/1999 | Cragg et al. | |
| 5,873,891 A | 2/1999 | Sohn | |
| 5,879,357 A | 3/1999 | Heaton et al. | |
| 5,897,574 A | 4/1999 | Bonutti | |
| 5,899,911 A | 5/1999 | Carter | |
| 5,899,921 A | 5/1999 | Caspari et al. | |
| 5,904,679 A | 5/1999 | Clayman | |
| 5,904,696 A | 5/1999 | Rosenman | |
| 5,908,428 A | 6/1999 | Scirica et al. | |
| 5,919,198 A | 7/1999 | Graves, Jr. et al. | |
| 5,919,202 A | 7/1999 | Yoon | |
| 5,921,986 A | 7/1999 | Bonutti | |
| 5,928,252 A | 7/1999 | Steadman et al. | |
| 5,931,844 A | 8/1999 | Thompson et al. | |
| 5,944,739 A | 8/1999 | Zlock et al. | |
| 5,948,001 A | 9/1999 | Larsen | |
| 5,948,002 A | 9/1999 | Bonutti | |
| 5,954,057 A | 9/1999 | Li | |
| 5,954,747 A | 9/1999 | Clark | |
| 5,964,732 A | 10/1999 | Willard | |
| 5,971,447 A | 10/1999 | Steck, III | |
| 6,010,514 A | 1/2000 | Burney et al. | |
| 6,011,525 A | 1/2000 | Piole | |
| 6,030,393 A | 2/2000 | Corlew | |
| 6,033,430 A | 3/2000 | Bonutti | |
| 6,036,701 A | 3/2000 | Rosenman | |
| 6,048,351 A | 4/2000 | Gordon et al. | |
| 6,053,908 A | 4/2000 | Crainich et al. | |
| 6,056,722 A | 5/2000 | Jayaraman | |
| 6,056,772 A | 5/2000 | Bonutti | |
| 6,068,648 A | 5/2000 | Cole et al. | |
| 6,080,167 A | 6/2000 | Lyell | |
| 6,086,608 A | 7/2000 | Ek et al. | |
| 6,110,183 A | 8/2000 | Cope | |
| 6,117,160 A | 9/2000 | Bonutti | |
| 6,117,161 A | 9/2000 | Li et al. | |

| | | | | | | |
|---|---|---|---|---|---|---|
| 6,120,539 | A | 9/2000 | Eldridge et al. | 6,991,647 B2 | 1/2006 | Jadhav |
| 6,139,555 | A | 10/2000 | Hart et al. | 6,997,940 B2 | 2/2006 | Bonutti |
| RE36,974 | E | 11/2000 | Bonutti | 7,001,327 B2 | 2/2006 | Whalen et al. |
| 6,143,006 | A | 11/2000 | Chan | 7,011,688 B2 | 3/2006 | Gryska et al. |
| 6,152,935 | A | 11/2000 | Kammerer et al. | 7,015,253 B2 | 3/2006 | Escandon et al. |
| 6,159,234 | A | 12/2000 | Bonutti et al. | 7,048,698 B2 | 5/2006 | Whalen et al. |
| 6,200,329 | B1 | 3/2001 | Fung et al. | 7,048,747 B2 | 5/2006 | Arcia et al. |
| 6,206,895 | B1 | 3/2001 | Levinson | 7,060,077 B2 | 6/2006 | Gordon et al. |
| 6,228,096 | B1 | 5/2001 | Marchand | 7,081,126 B2 | 7/2006 | McDevitt et al. |
| 6,258,124 | B1 | 7/2001 | Darois et al. | 7,083,638 B2 | 8/2006 | Foerster |
| 6,261,302 | B1 | 7/2001 | Voegele et al. | 7,087,073 B2 | 8/2006 | Bonutti |
| 6,270,530 | B1 | 8/2001 | Eldridge et al. | 7,089,064 B2 | 8/2006 | Manker et al. |
| 6,280,460 | B1 | 8/2001 | Bolduc et al. | 7,090,690 B2 | 8/2006 | Foerster et al. |
| 6,290,711 | B1 | 9/2001 | Caspari et al. | 7,093,601 B2 | 8/2006 | Manker et al. |
| 6,312,448 | B1 | 11/2001 | Bonutti | 7,105,004 B2 | 9/2006 | Dicesare et al. |
| 6,319,263 | B1 | 11/2001 | Levinson | 7,108,655 B2 | 9/2006 | Whalen et al. |
| 6,322,112 | B1 | 11/2001 | Duncan | 7,141,038 B2 | 11/2006 | Whalen et al. |
| 6,332,889 | B1 | 12/2001 | Sancoff et al. | 7,153,314 B2 | 12/2006 | Laufer et al. |
| 6,398,795 | B1 | 6/2002 | McAlister et al. | 7,179,225 B2 | 2/2007 | Shluzas |
| 6,425,900 | B1 | 7/2002 | Knodel et al. | 7,226,558 B2 | 6/2007 | Nieman et al. |
| 6,428,562 | B2 | 8/2002 | Bonutti | 7,232,448 B2 | 6/2007 | Battles et al. |
| 6,436,107 | B1 | 8/2002 | Wang et al. | 7,288,063 B2 | 10/2007 | Petros et al. |
| 6,461,355 | B2 | 10/2002 | Svejkovsky et al. | 7,303,108 B2 | 12/2007 | Shelton, IV |
| 6,482,235 | B1 | 11/2002 | Lambrecht et al. | 7,320,701 B2 | 1/2008 | Haut et al. |
| 6,488,691 | B1 | 12/2002 | Carroll et al. | 7,322,974 B2 | 1/2008 | Swoyer et al. |
| 6,491,707 | B2 | 12/2002 | Makower et al. | 7,326,221 B2 | 2/2008 | Sakamoto et al. |
| 6,494,888 | B1 | 12/2002 | Laufer et al. | 7,334,822 B1 | 2/2008 | Hines, Jr. |
| 6,500,195 | B2 | 12/2002 | Bonutti | 7,340,300 B2 | 3/2008 | Christopherson et al. |
| 6,506,190 | B1 | 1/2003 | Walshe | 7,399,304 B2 | 7/2008 | Gambale et al. |
| 6,506,196 | B1 | 1/2003 | Laufer | 7,402,166 B2 | 7/2008 | Feigl |
| 6,517,569 | B2 | 2/2003 | Mikus et al. | 7,416,554 B2 | 8/2008 | Lam et al. |
| 6,527,702 | B2 | 3/2003 | Whalen et al. | 7,417,175 B2 | 8/2008 | Oda et al. |
| 6,527,794 | B1 | 3/2003 | McDevitt et al. | 7,481,771 B2 | 1/2009 | Fonseca et al. |
| 6,530,932 | B1 | 3/2003 | Swayze et al. | 7,553,317 B2 | 6/2009 | Weisenburgh, II et al. |
| 6,533,796 | B1 | 3/2003 | Sauer et al. | 7,608,108 B2 | 10/2009 | Bhatnagar et al. |
| 6,547,725 | B1 | 4/2003 | Paolitto et al. | 7,658,311 B2 | 2/2010 | Boudreaux |
| 6,551,328 | B2 | 4/2003 | Kortenbach | 7,674,275 B2 | 3/2010 | Martin et al. |
| 6,551,333 | B2 | 4/2003 | Kuhns et al. | 7,727,248 B2 | 6/2010 | Smith et al. |
| 6,565,578 | B1 | 5/2003 | Peifer et al. | 2001/0044639 A1 | 11/2001 | Levinson |
| 6,569,187 | B1 | 5/2003 | Bonutti et al. | 2002/0095154 A1 | 7/2002 | Atkinson et al. |
| 6,572,626 | B1 | 6/2003 | Knodel et al. | 2002/0128684 A1 | 9/2002 | Foerster |
| 6,572,635 | B1 | 6/2003 | Bonutti | 2002/0161382 A1 | 10/2002 | Neisz et al. |
| 6,572,653 | B1 | 6/2003 | Simonson | 2002/0193809 A1 | 12/2002 | Meade |
| 6,592,609 | B1 | 7/2003 | Bonutti | 2003/0109769 A1 | 6/2003 | Lowery et al. |
| 6,596,013 | B2 | 7/2003 | Yang et al. | 2003/0191497 A1 | 10/2003 | Cope |
| 6,626,913 | B1 | 9/2003 | McKinnon et al. | 2003/0204195 A1 | 10/2003 | Keane et al. |
| 6,626,916 | B1 | 9/2003 | Yeung et al. | 2003/0236535 A1 | 12/2003 | Onuki et al. |
| 6,626,919 | B1 | 9/2003 | Swanstrom | 2004/0030217 A1 | 2/2004 | Yeung et al. |
| 6,629,534 | B1 | 10/2003 | St. Goar et al. | 2004/0043052 A1 | 3/2004 | Hunter et al. |
| 6,641,592 | B1 | 11/2003 | Sauer et al. | 2004/0078046 A1 | 4/2004 | Barzell et al. |
| 6,656,182 | B1 | 12/2003 | Hayhurst | 2004/0193191 A1 | 9/2004 | Starksen et al. |
| 6,660,023 | B2 | 12/2003 | McDevitt et al. | 2004/0193194 A1 | 9/2004 | Laufer et al. |
| 6,663,589 | B1 | 12/2003 | Halevy | 2004/0194790 A1 | 10/2004 | Laufer et al. |
| 6,663,639 | B1 | 12/2003 | Laufer et al. | 2004/0243178 A1 | 12/2004 | Haut et al. |
| 6,699,263 | B2 | 3/2004 | Cope | 2004/0243179 A1 | 12/2004 | Foerster |
| 6,706,047 | B2 | 3/2004 | Trout et al. | 2004/0243180 A1 | 12/2004 | Donnelly |
| 6,709,493 | B2 | 3/2004 | DeGuiseppi et al. | 2004/0243227 A1 | 12/2004 | Starksen et al. |
| 6,715,804 | B2 | 4/2004 | Beers | 2004/0260345 A1 | 12/2004 | Foerster |
| 6,719,709 | B2 | 4/2004 | Whalen et al. | 2005/0055087 A1 | 3/2005 | Starksen |
| 6,730,112 | B2 | 5/2004 | Levinson | 2005/0065550 A1 | 3/2005 | Starksen et al. |
| 6,736,823 | B2 | 5/2004 | Darois et al. | 2005/0107811 A1 | 5/2005 | Starksen et al. |
| 6,736,854 | B2 | 5/2004 | Vadurro et al. | 2005/0107812 A1 | 5/2005 | Starksen et al. |
| 6,740,098 | B2 | 5/2004 | Abrams et al. | 2005/0154401 A1 | 7/2005 | Weldon et al. |
| 6,767,037 | B2 | 7/2004 | Wenstrom, Jr. | 2005/0165272 A1 | 7/2005 | Okada et al. |
| 6,770,076 | B2 | 8/2004 | Foerster | 2005/0177181 A1 | 8/2005 | Kagan et al. |
| 6,773,438 | B1 | 8/2004 | Knodel et al. | 2005/0203344 A1 | 9/2005 | Orban, III et al. |
| 6,773,441 | B1 | 8/2004 | Laufer et al. | 2005/0203550 A1 | 9/2005 | Laufer et al. |
| 6,790,213 | B2 | 9/2004 | Cherok et al. | 2005/0216078 A1 | 9/2005 | Starksen et al. |
| 6,802,846 | B2 | 10/2004 | Hauschild et al. | 2005/0267405 A1 | 12/2005 | Shah |
| 6,821,282 | B2 | 11/2004 | Perry et al. | 2005/0273138 A1 | 12/2005 | Starksen et al. |
| 6,821,285 | B2 | 11/2004 | Laufer et al. | 2006/0025750 A1 | 2/2006 | Starksen et al. |
| 6,821,291 | B2 | 11/2004 | Bolea et al. | 2006/0025784 A1 | 2/2006 | Starksen et al. |
| 6,835,200 | B2 | 12/2004 | Laufer et al. | 2006/0025789 A1 | 2/2006 | Laufer et al. |
| 6,905,475 | B2 | 6/2005 | Hauschild et al. | 2006/0025819 A1 | 2/2006 | Nobis et al. |
| 6,908,473 | B2 | 6/2005 | Skiba et al. | 2006/0030884 A1 | 2/2006 | Yeung et al. |
| 6,926,732 | B2 | 8/2005 | Derus et al. | 2006/0058817 A1 | 3/2006 | Starksen et al. |
| 6,951,565 | B2 | 10/2005 | Keane et al. | 2006/0089646 A1 | 4/2006 | Bonutti |
| 6,986,775 | B2 | 1/2006 | Morales et al. | 2006/0167477 A1 | 7/2006 | Arcia et al. |
| 6,991,596 | B2 | 1/2006 | Whalen et al. | 2006/0265042 A1 | 11/2006 | Catanese, III et al. |

| | | | |
|---|---|---|---|
| 2006/0282081 A1 | 12/2006 | Fanton et al. | |
| 2007/0049929 A1 | 3/2007 | Catanese, III | |
| 2007/0049970 A1 | 3/2007 | Belef et al. | |
| 2007/0060931 A1 | 3/2007 | Hamilton et al. | |
| 2007/0088362 A1 | 4/2007 | Bonutti | |
| 2007/0112385 A1 | 5/2007 | Conlon | |
| 2007/0142846 A1 | 6/2007 | Catanese, III et al. | |
| 2007/0173888 A1 | 7/2007 | Gertner et al. | |
| 2007/0260259 A1 | 11/2007 | Fanton et al. | |
| 2008/0009888 A1 | 1/2008 | Ewers et al. | |
| 2008/0021445 A1 | 1/2008 | Elmouelhi et al. | |
| 2008/0033488 A1 | 2/2008 | Catanese, III et al. | |
| 2008/0039894 A1 | 2/2008 | Catanese, III et al. | |
| 2008/0045978 A1 | 2/2008 | Kuhns et al. | |
| 2008/0058710 A1 | 3/2008 | Wilk | |
| 2008/0065120 A1 | 3/2008 | Zannis et al. | |
| 2008/0082113 A1 | 4/2008 | Bishop et al. | |
| 2008/0086172 A1 | 4/2008 | Martin et al. | |
| 2008/0091220 A1 | 4/2008 | Chu | |
| 2008/0091237 A1 | 4/2008 | Schwartz et al. | |
| 2008/0119874 A1 | 5/2008 | Merves | |
| 2008/0154378 A1 | 6/2008 | Pelo | |
| 2008/0195145 A1 | 8/2008 | Bonutti et al. | |
| 2008/0208220 A1 | 8/2008 | Shiono et al. | |
| 2010/0010631 A1 | 1/2010 | Otte et al. | |
| 2010/0114162 A1 | 5/2010 | Bojarski et al. | |
| 2010/0286106 A1 | 11/2010 | Gat et al. | |
| 2010/0286679 A1 | 11/2010 | Hoey et al. | |

FOREIGN PATENT DOCUMENTS

| | | |
|---|---|---|
| EP | 0246836 | 12/1991 |
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 0464480 | 1/2008 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO 92/10142 | 6/1992 |
| WO | WO 93/04727 | 3/1993 |
| WO | WO 93/15664 | 8/1993 |
| WO | WO 0230335 | 4/2002 |
| WO | WO 03/039334 | 5/2003 |
| WO | WO03/077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008443917 | 4/2008 |
| WO | WO2009009617 | 1/2009 |
| WO | WO2010011832 | 1/2010 |

OTHER PUBLICATIONS

Rudolf Hartung, et al., "Instrumentelle Therapie der benignen Prostatahyperplasie", Medizin, Deutsches Arzteblatt 97, Heft 15, Apr. 14, 2000, cited by other.

Klaus Hofner, et al., "Operative Therapie des benignen Prostatasyndroms", Medizin, Dtsch Arztebl 2007; 104(36):A 2424-9, cited by other.

R. Hubmann, "Geschichte der transurethralen Prostataeingriffe", Geschichte der Medizin, Urologe [B] 2000 40:152-160, cited by other.

U. Jonas, et al., "Benigne Prostatahyperplasie", Der Urologe 2006—[Sonderheft] 45:134-144, cited by other.

O.A. Bacharova, et al., "The Effect of Rhodiolae Rosea Extract on Incidence Rate of Superficial Bladder Carcinoma Relapses", Kozin 1995, cited by other.

S. Kruck, et al., "Aktuelle Therapiemoglichkeiten des Benignen Prostata-Syndroms", J Urol Urogynakol 2009; 16 (1): 19-22, cited by other.

Osamu Miyake, "Medical Examination and Treatment For BPH", Pharma Med vol. 22, No. 3, 2004, p. 97-103, cited by other.

Ohashi Teruhisa, "Urinary Dysfunction by Lower Urinary Tract Obstruction in Male", Pharma Medica vol. 8, No. 8, p. 35-39, cited by other, 1990.

O. Reich, et al. "Benignes Prostatasyndrom (BPS)", Der Urologe A Issue vol. 45, No. 6, Jun. 2006, p. 769-782, cited by other.

Daito Takashi, "Low-Invasive Treatment for BPH", Medico vol. 34, No. 10, p. 366-369, cited by other, 2003.

Trapeznikov et al., "New Technologies in the Treatment of Benign Prostatic Hyperplasia", Urologia Nefrol (Mosk) Jul.-Aug. 1996, (4):41-47, cited by other.

Koyanagi Tomohiko, et al., "Surgery View of 21st Century", Urological Surgery, vol. 84, No. 1, p. 47-53, cited by other, 2001.

Borzhievski, et al., "Tactics of the Surgical Treatment of Patients With Prostatic Adenoma and Acute Urinary Retention", Urologia Nefrol (Mosk), Jan.-Feb. 1987, (1):39-43, cited by other.

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997, cited by other.

P. Schauer et al., "New applications for endoscopy: the emerging field of endoluminal and transgastric bariatric surgery," Surgical Endoscopy, Received Apr. 24, 2006/Accepted Jun. 7, 2006, cited by other.

Yeung, Jeff, "Treating Urinary Stress Incontinence Without Incision With Endoscopic Suture Anchor and Approximating Device," Aleeva Medical, Inc., 2007.

* cited by examiner

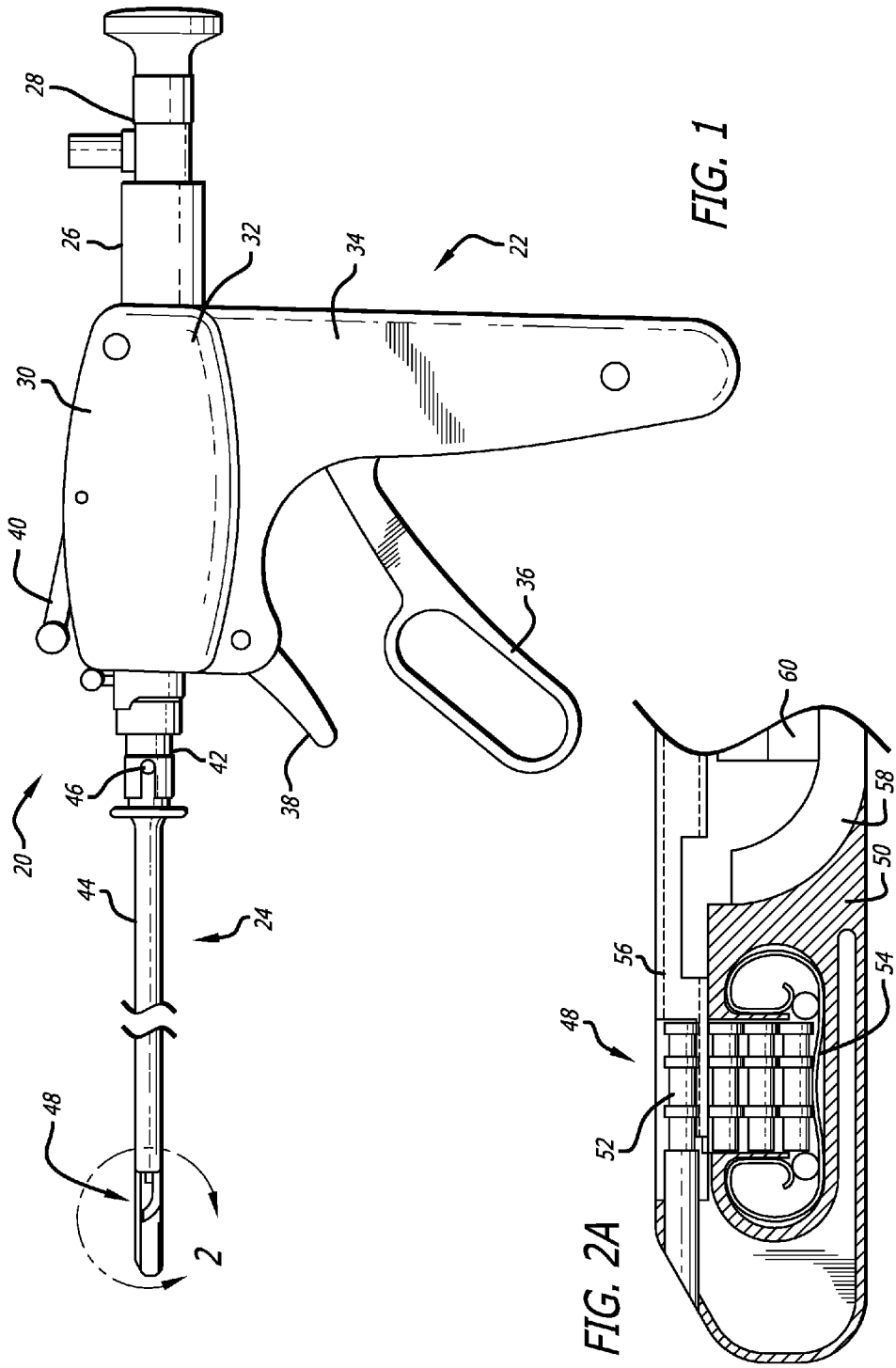

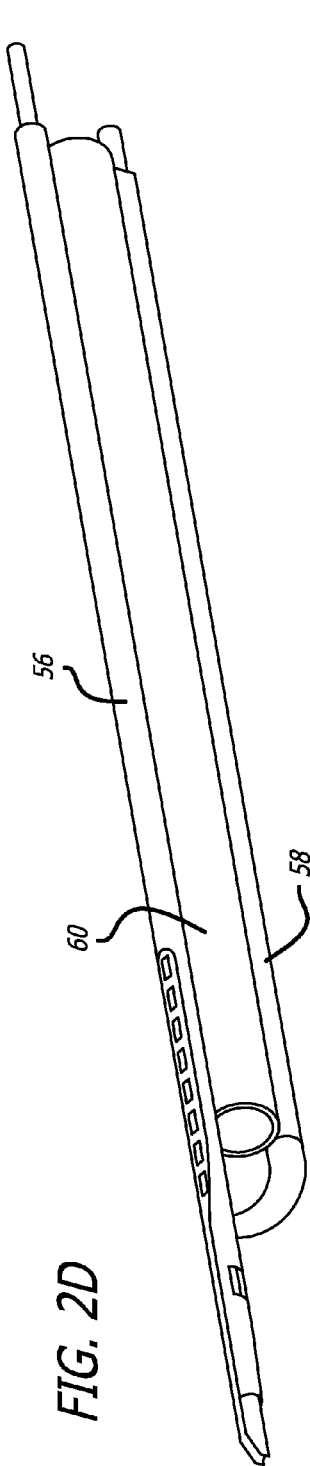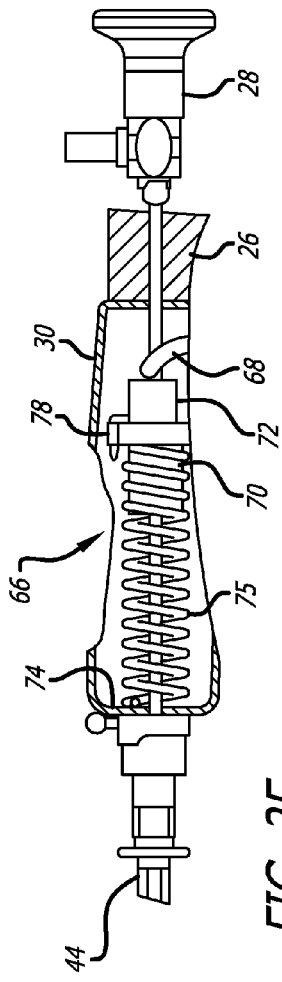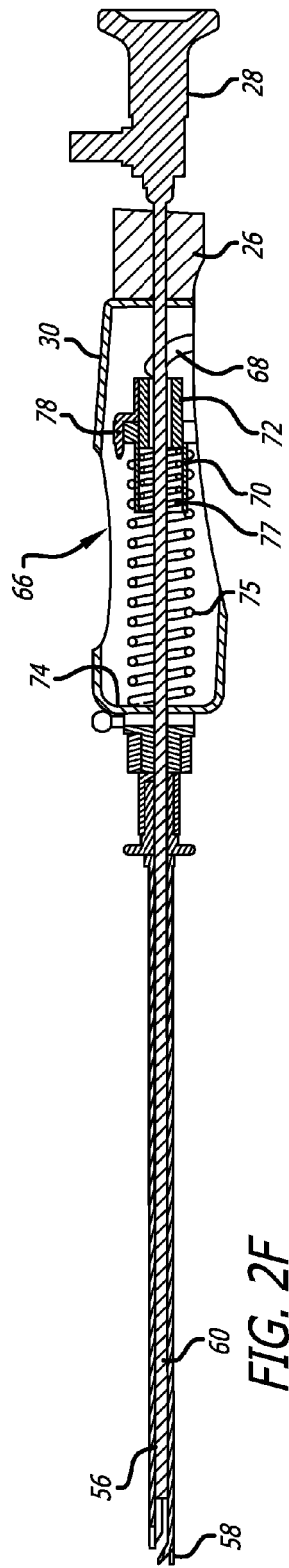
FIG. 2D
FIG. 2E
FIG. 2F

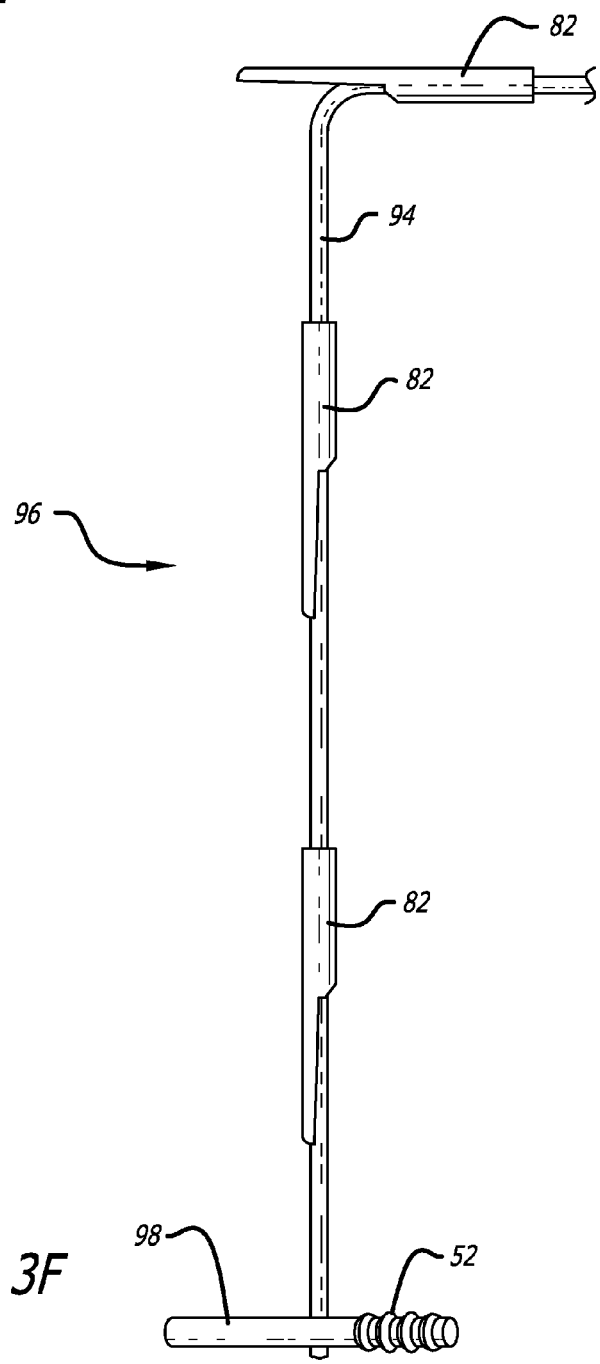

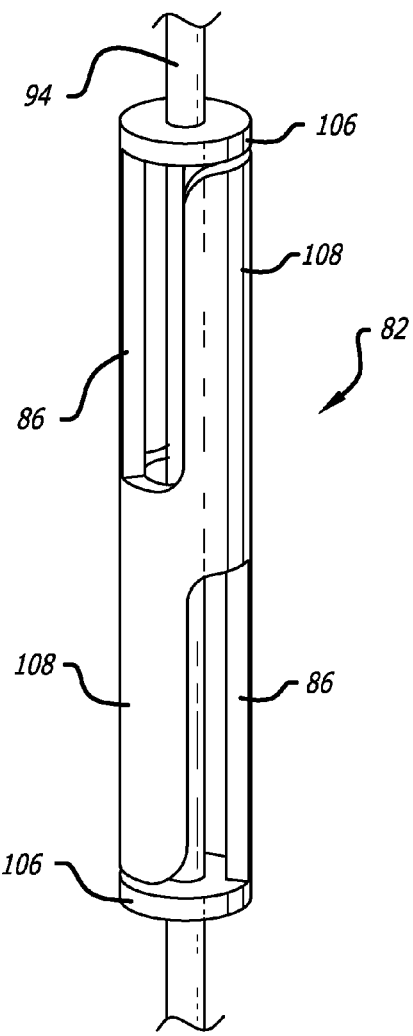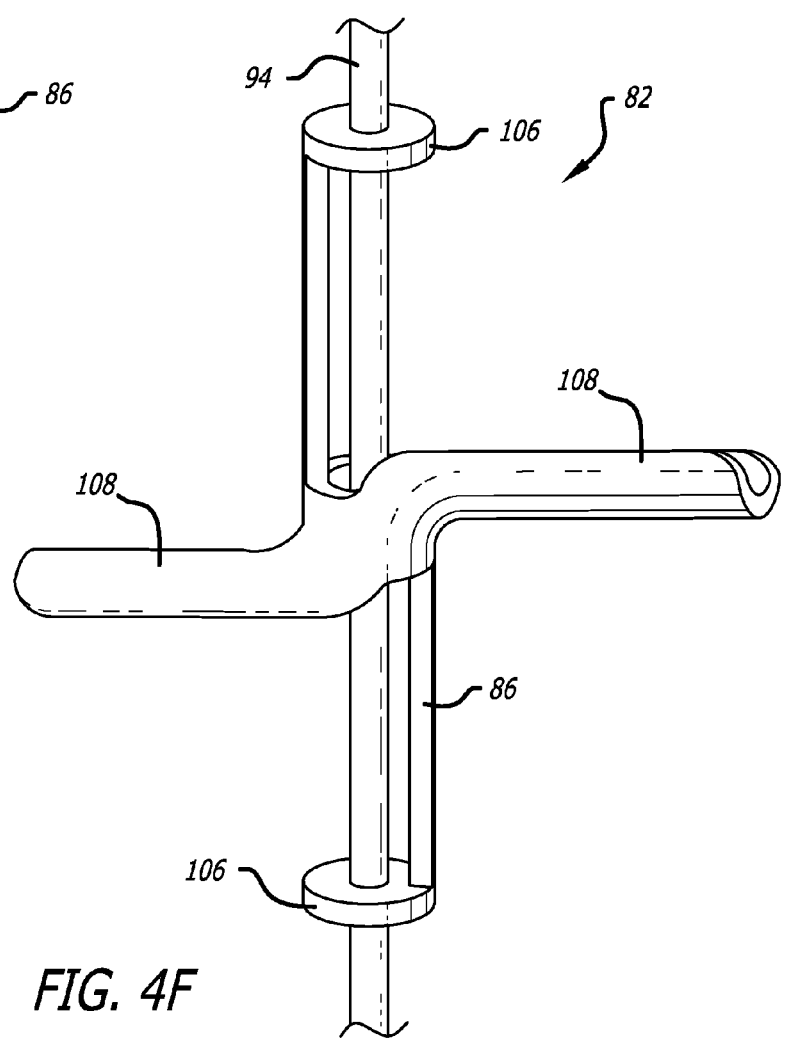
FIG. 4E
FIG. 4F

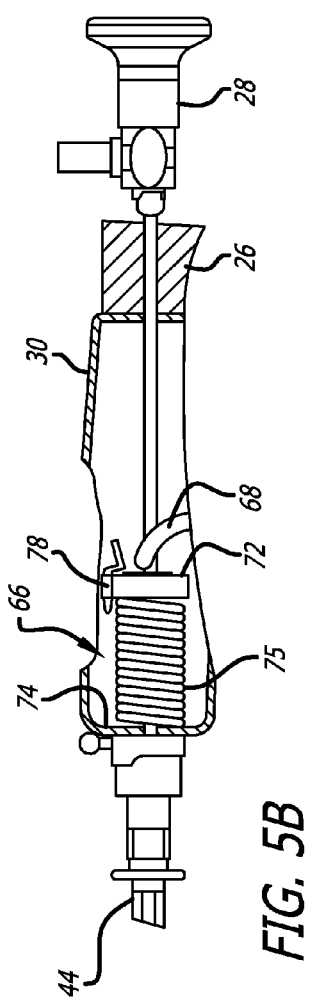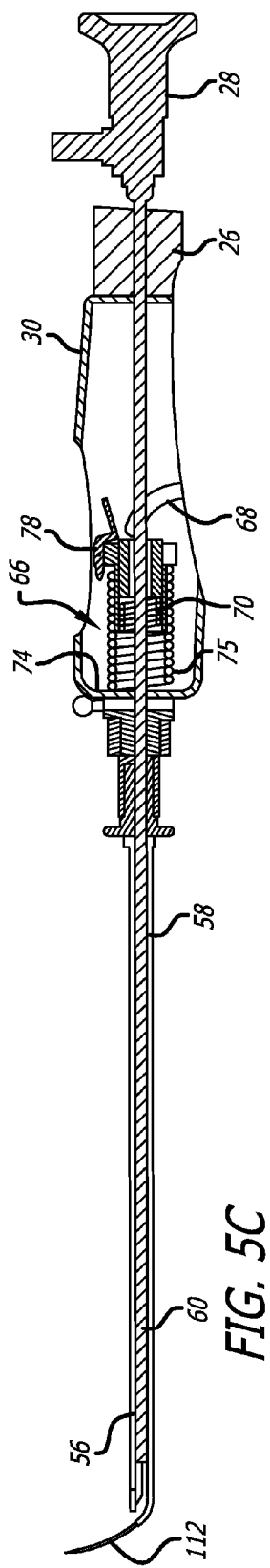
FIG. 5B
FIG. 5C

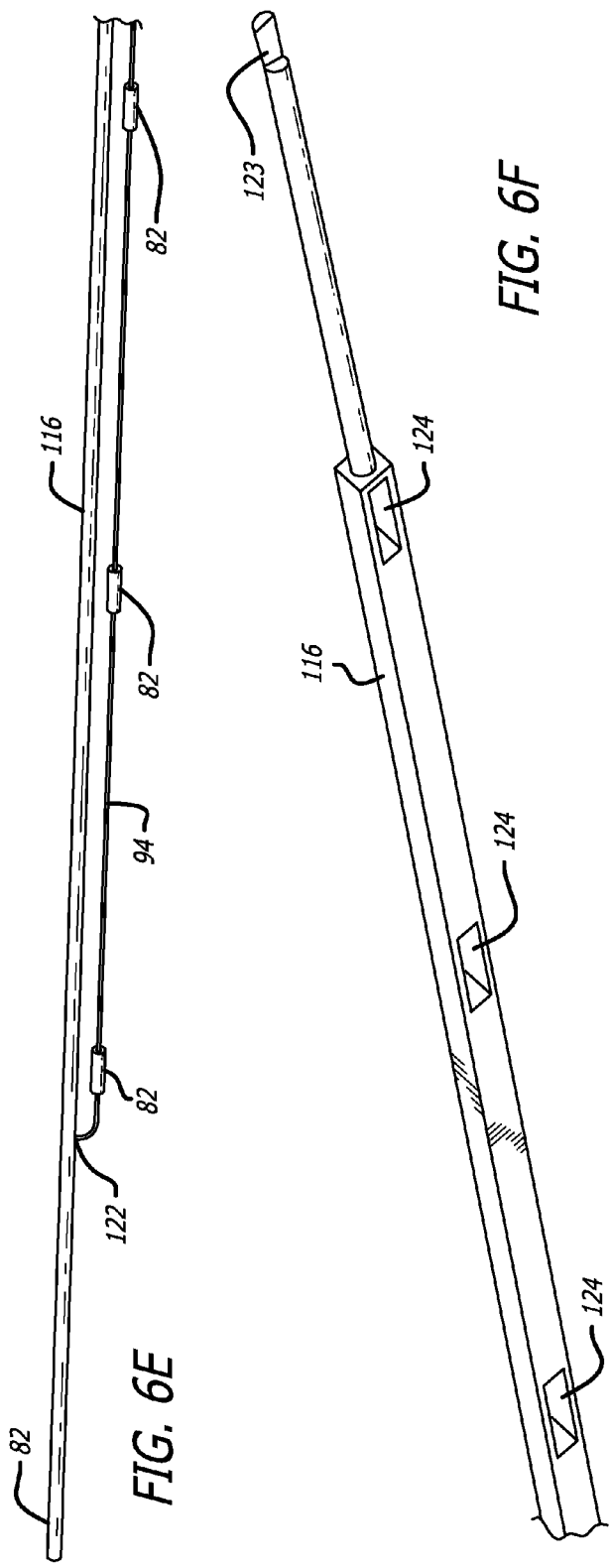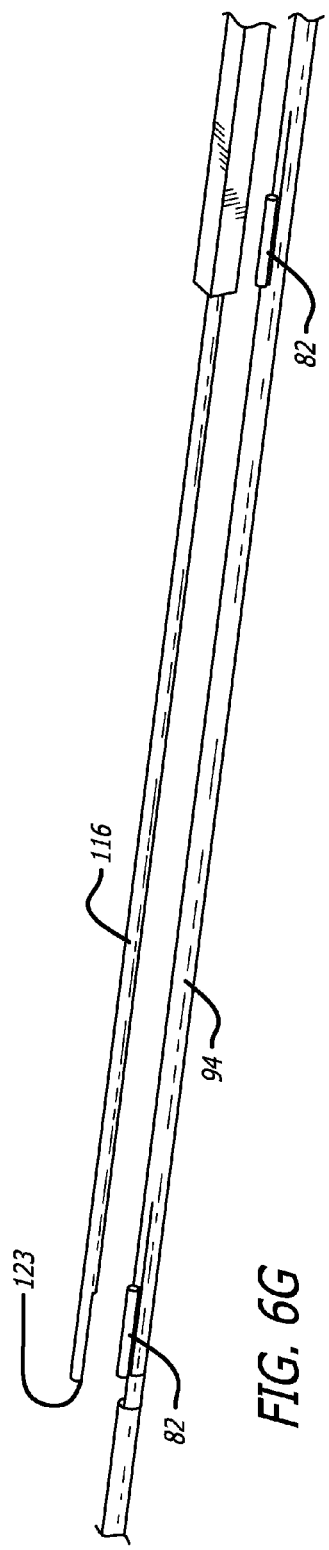

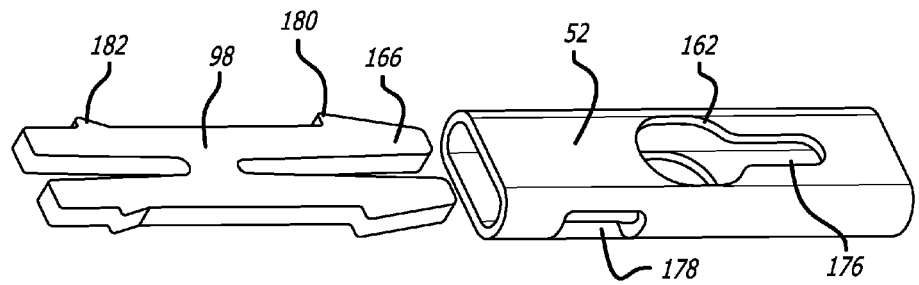
FIG. 9N
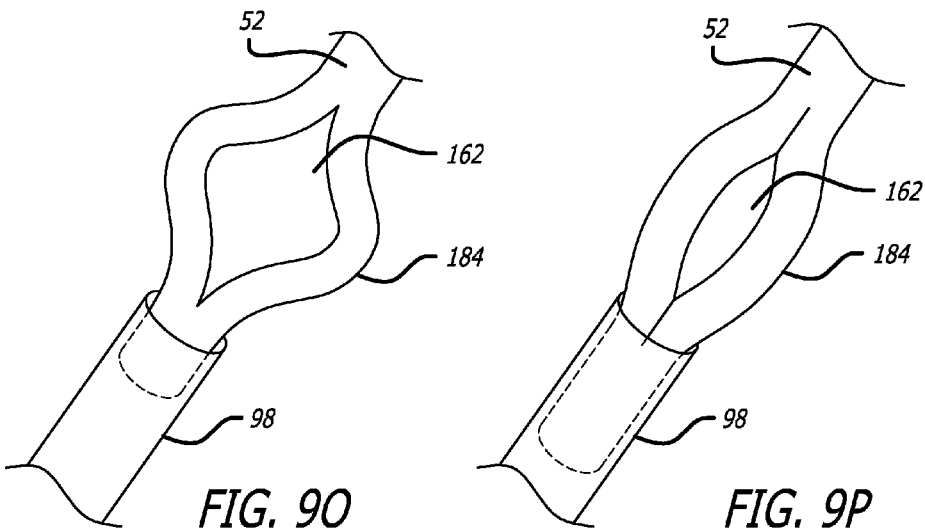
FIG. 9O
FIG. 9P
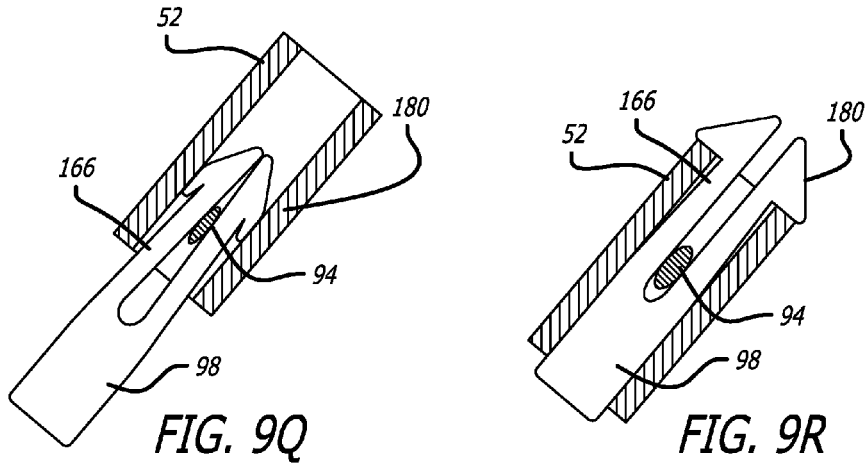
FIG. 9Q
FIG. 9R

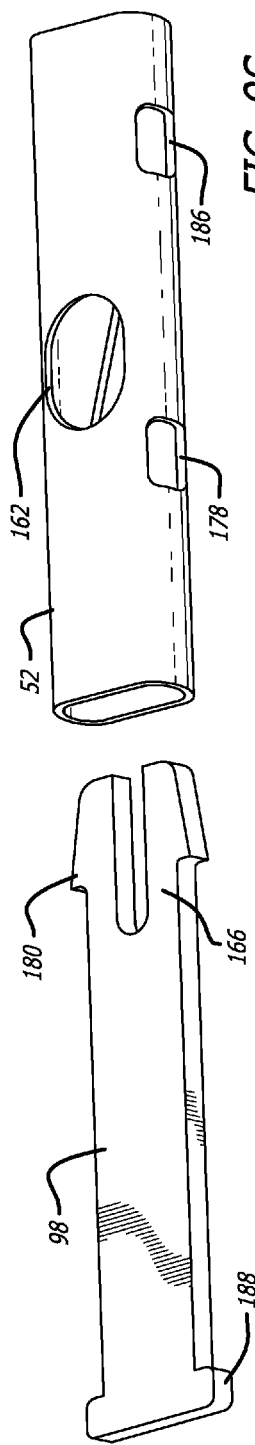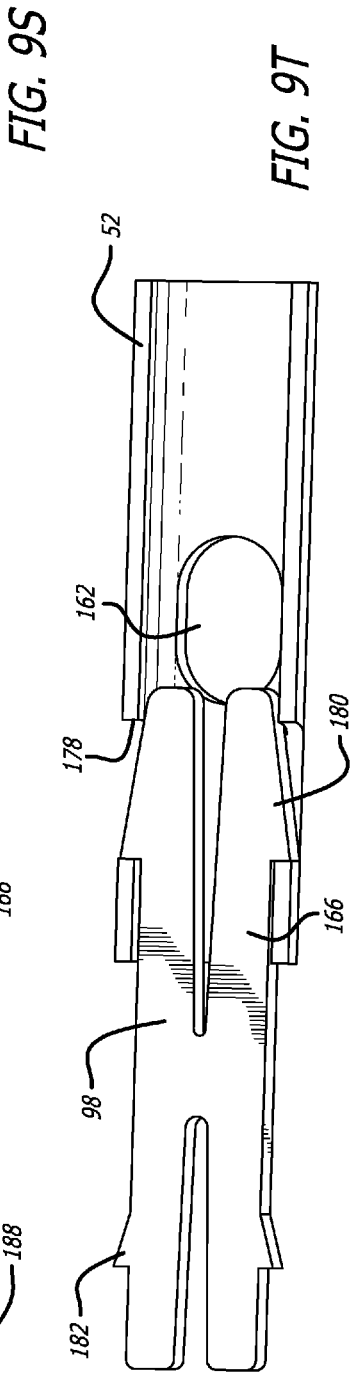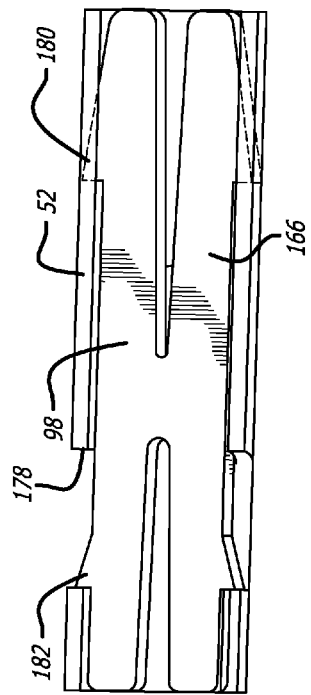

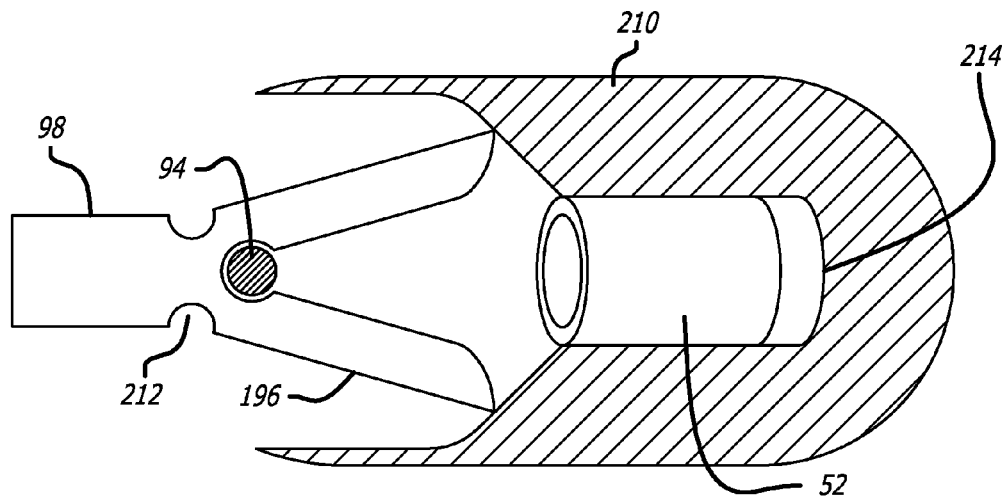
FIG. 9AJ
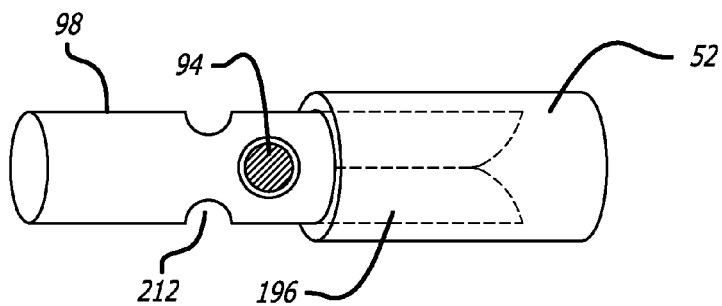
FIG. 9AK
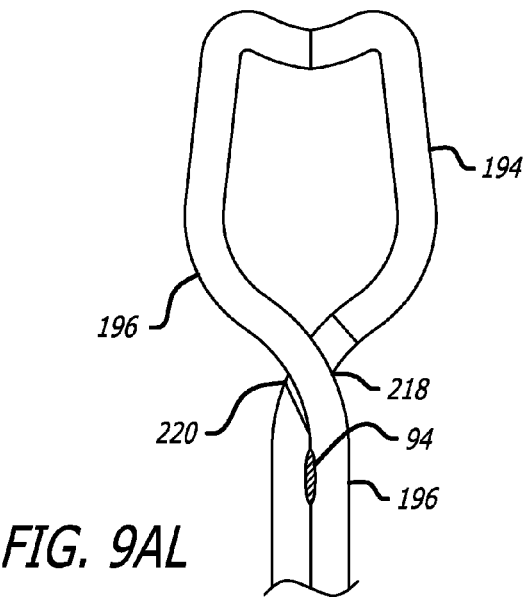 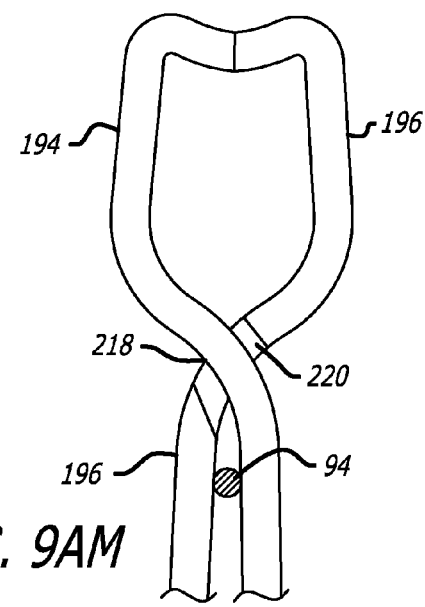
FIG. 9AL　　　　FIG. 9AM

APPARATUS AND METHOD FOR MANIPULATING OR RETRACTING TISSUE AND ANATOMICAL STRUCTURE

CROSS-REFERENCES TO RELATED APPLICATIONS

This application is a divisional of U.S. patent application Ser. No. 11/492,690, now U.S. Pat. No. 7,896,891, entitled Apparatus and Method for Manipulating or Retracting Tissue and Anatomical Structure, filed on Jul. 24, 2006, which is a continuation-in-part of U.S. patent application Ser. No. 11/318,246, now U.S. Pat. No. 7,645,286, entitled Devices, Systems and Methods for Retracting, Lifting, Compressing, Supporting or Repositioning Tissues or Anatomical Structures, filed on Dec. 22, 2005, which is a continuation-in-part of U.S. patent application Ser. No. 11/134,870, now U.S. Pat. No. 7,758,594, entitled Devices, Systems and Methods for Treating Benign Prostatic Hyperplasia and Other Conditions, filed on May 20, 2005, the entire disclosures of which are expressly incorporated herein by reference.

FIELD OF THE INVENTION

The present invention relates generally to medical devices and methods, and more particularly to integrated systems and associated methods for manipulating or retracting tissues and anatomical or other structures within the body of human or animal subjects for the purpose of treating diseases or disorders and/or for cosmetic or reconstructive or other purposes.

BACKGROUND OF THE INVENTION

There are a wide variety of situations in which it is desirable to lift, compress or otherwise reposition normal or aberrant tissues or anatomical structures (e.g., organs, ligaments, tendons, muscles, tumors, cysts, fat pads, etc.) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, etc.) and/or for cosmetic purposes (e.g., face lifts, breast lifts, brow lifts, etc.) and/or for research and development purposes (e.g., to create animal models that mimic various pathological conditions). In many of these procedures, surgical incisions are made in the body and laborious surgical dissection is performed to access and expose the affected tissues or anatomical structures. Thereafter, in some cases, the affected tissues or anatomical structures are removed or excised. In other cases, various natural or man made materials are used to lift, sling, reposition or compress the affected tissues.

Benign Prostatic Hyperplasia (BPH)

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Medications for treating BPH symptoms include phytotherapy and prescription medications. In phytotherapy, plant products such as Saw Palmetto, African Pygeum, *Serenoa Repens* (sago palm) and South African star grass are administered to the patient. Prescription medications are prescribed as first line therapy in patients with symptoms that are interfering with their daily activities. Two main classes of prescription medications are alpha-1a-adrenergic receptors blockers and 5-alpha-reductase inhibitors. Alpha-1a-adrenergic receptors blockers block that activity of alpha-1a-adrenergic receptors that are responsible for causing constriction of smooth muscle cells in the prostate. Thus, blocking the activity of alpha-1a-adrenergic receptors causes prostatic smooth muscle relaxation. This in turn reduces urethral resistance thereby reducing the severity of the symptoms. 5-alpha-reductase inhibitors block the conversion of testosterone to dihydrotestosterone. Dihydrotestosterone causes growth of epithelial cells in the prostate gland. Thus 5-alpha-reductase inhibitors cause regression of epithelial cells in the prostate gland and hence reduce the volume of the prostate gland which in turn reduces the severity of the symptoms.

Surgical procedures for treating BPH symptoms include Transurethral Resection of Prostate (TURP), Transurethral Electrovaporization of Prostate (TVP), Transurethral Incision of the Prostate (TUIP), Laser Prostatectomy and Open Prostatectomy.

Transurethral Resection of Prostate (TURP) is the most commonly practiced surgical procedure implemented for the treatment of BPH. In this procedure, prostatic urethral obstruction is reduced by removing most of the prostatic urethra and a sizeable volume of the surrounding prostate gland. This is carried out under general or spinal anesthesia. In this procedure, a urologist visualizes the urethra by inserting a resectoscope, that houses an optical lens in communication with a video camera, into the urethra such that the distal region of the resectoscope is in the region of the urethra surrounded by the prostate gland. The distal region of the resectoscope consists of an electric cutting loop that can cut prostatic tissue when an electric current is applied to the device. An electric return pad is placed on the patient to close the cutting circuit. The electric cutting loop is used to scrape away tissue from the inside of the prostate gland. The tissue that is scraped away is flushed out of the urinary system using an irrigation fluid. Using a coagulation energy setting, the loop is also used to cauterize transected vessels during the operation.

Another example of a surgical procedure for treating BPH symptoms is Transurethral Electrovaporization of the Prostate (TVP). In this procedure, a part of prostatic tissue squeezing the urethra is desiccated or vaporized. This is carried out under general or spinal anesthesia. In this procedure, a resectoscope is inserted transurethrally such that the distal region of the resectoscope is in the region of the urethra surrounded by the prostate gland. The distal region of the resectoscope consists of a rollerball or a grooved roller electrode. A controlled amount of electric current is passed through the electrode. The surrounding tissue is rapidly heated up and vaporized to create a vaporized space. Thus the region of urethra that is blocked by the surrounding prostate gland is opened up.

Another example of a surgical procedure for treating BPH symptoms is Transurethral Incision of the Prostate (TUIP). In this procedure, the resistance to urine flow is reduced by making one or more incisions in the prostate gland in the region where the urethra meets the urinary bladder. This procedure is performed under general or spinal anesthesia. In this procedure, one or more incisions are made in the muscle of the bladder neck, which is the region where the urethra meets the urinary bladder. The incisions are in most cases are deep enough to cut the surrounding prostate gland tissue including the prostatic capsule. This releases any compression on the bladder neck and causes the bladder neck to spring apart. The incisions can be made using a resectoscope, laser beam etc.

Another example of a surgical procedure for treating BPH symptoms is Laser Prostatectomy. Two common techniques used for Laser Prostatectomy are Visual Laser Ablation of the Prostate (VLAP) and the Holmium Laser Resection/Enucleation of the Prostate (HoLEP). In VLAP, a neodymium:yttrium-aluminum-garnet (Nd:YAG) laser is used to ablate tissue by causing coagulation necrosis. The procedure is performed under visual guidance. In HoLEP, a holmium:Yttrium-aluminum-garnet laser is used for direct contact ablation of tissue. Both these techniques are used to remove tissue obstructing the urethral passage to reduce the severity of BPH symptoms.

Another example of a surgical procedure for treating BPH symptoms is Photoselective Vaporization of the Prostate (PVP). In this procedure, laser energy is used to vaporize prostatic tissue to relieve obstruction to urine flow in the urethra. The type of laser used is the Potassium-Titanyl-Phosphate (KTP) laser. The wavelength of this laser is highly absorbed by oxyhemoglobin. This laser vaporizes cellular water and hence is used to remove tissue that is obstructing the urethra.

Another example of a surgical procedure for treating BPH symptoms is Open Prostatectomy. In this procedure, the prostate gland is surgically removed by an open surgery. This is done under general anesthesia. The prostate gland is removed through an incision in the lower abdomen or the perineum. The procedure is used mostly in patients that have a large (greater than approximately 100 grams) prostate gland.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

In Transurethral Microwave Thermotherapy (TUMT), microwave energy is used to generate heat that destroys hyperplastic prostate tissue. This procedure is performed under local anesthesia. In this procedure, a microwave antenna is inserted in the urethra. A rectal thermosensing unit is inserted into the rectum to measure rectal temperature. Rectal temperature measurements are used to prevent overheating of the anatomical region. The microwave antenna is then used to deliver microwaves to lateral lobes of the prostate gland. The microwaves are absorbed as they pass through prostate tissue. This generates heat which in turn destroys the prostate tissue. The destruction of prostate tissue reduces the degree of squeezing of the urethra by the prostate gland thus reducing the severity of BPH symptoms.

Another example of a minimally invasive procedure for treating BPH symptoms is Transurethral Needle Ablation (TUNA). In this procedure, heat induced coagulation necrosis of prostate tissue regions causes the prostate gland to shrink. It is performed using local anesthetic and intravenous or oral sedation. In this procedure, a delivery catheter is inserted into the urethra. The delivery catheter comprises two radiofrequency needles that emerge at an angle of 90 degrees from the delivery catheter. The two radiofrequency needles are aligned at an angle of 40 degrees to each other so that they penetrate the lateral lobes of the prostate. A radiofrequency current is delivered through the radiofrequency needles to heat the tissue of the lateral lobes to 70-100 degree Celsius at a radiofrequency power of approximately 456 KHz for approximately 4 minutes per lesion. This creates coagulation defects in the lateral lobes. The coagulation defects cause shrinkage of prostatic tissue which in turn reduces the degree of squeezing of the urethra by the prostate gland thus reducing the severity of BPH symptoms.

Another example of a minimally invasive procedure for treating BPH symptoms is Interstitial Laser Coagulation (ILC). In this procedure, laser induced necrosis of prostate tissue regions causes the prostate gland to shrink. It is performed using regional anesthesia, spinal or epidural anesthesia or local anesthesia (periprostatic block). In this procedure, a cystoscope sheath is inserted into the urethra and the region of the urethra surrounded by the prostate gland is inspected. A laser fiber is inserted into the urethra. The laser fiber has a sharp distal tip to facilitate the penetration of the laser scope into prostatic tissue. The distal tip of the laser fiber has a distal-diffusing region that distributes laser energy 360° along the terminal 3 mm of the laser fiber. The distal tip is inserted into the middle lobe of the prostate gland and laser energy is delivered through the distal tip for a desired time. This heats the middle lobe and causes laser induced necrosis of the tissue around the distal tip. Thereafter, the distal tip is withdrawn from the middle lobe. The same procedure of inserting the distal tip into a lobe and delivering laser energy is repeated with the lateral lobes. This causes tissue necrosis in several regions of the prostate gland which in turn causes the prostate gland to shrink. Shrinkage of the prostate gland reduces the degree of squeezing of the urethra by the prostate thus reducing the severity of BPH symptoms.

Another example of a minimally invasive procedure for treating BPH symptoms is implanting Prostatic Stents. In this procedure, the region of urethra surrounded by the prostate is mechanically supported to reduce the constriction caused by an enlarged prostate. Prostatic stents are flexible devices that are expanded after their insertion in the urethra. They mechanically support the urethra by pushing the obstructing prostatic tissue away from the urethra. This reduces the constriction of the urethra and improves urine flow past the prostate gland thereby reducing the severity of BPH symptoms.

Although existing treatments provide some relief to the patient from symptoms of BPH, they have disadvantages. Alpha-1a-adrenergic receptors blockers have side effects such as dizziness, postural hypotension, lightheadedness, asthenia and nasal stuffiness. Retrograde ejaculation can also occur. 5-alpha-reductase inhibitors have minimal side effects, but only a modest effect on BPH symptoms and the flow rate of urine. In addition, anti-androgens, such as 5-alpha-reductase, require months of therapy before LUTS improvements are observed. Surgical treatments of BPH carry a risk of complications including erectile dysfunction; retrograde ejaculation; urinary incontinence; complications related to anesthesia; damage to the penis or urethra, need for a repeat surgery etc. Even TURP, which is the gold standard in treatment of BPH, carries a high risk of complications. Adverse events associated with this procedure are reported to include retrograde ejaculation (65% of patients), post-operative irritation (15%), erectile dysfunction (10%), need for transfusion (8%), bladder neck constriction (7%), infection (6%), significant hematuria (6%), acute urinary retention (5%), need for secondary procedure (5%), and incontinence (3%) Typical recovery from TURP involves several days of inpatient hospital treatment with an indwelling urethral catheter, followed by several weeks in which obstructive symptoms are relieved but there is pain or discomfort during micturition.

The reduction in the symptom score after minimally invasive procedures is not as large as the reduction in symptom score after TURP. Up to 25% of patients who receive these minimally invasive procedures ultimately undergo a TURP within 2 years. The improvement in the symptom score generally does not occur immediately after the procedure. For example, it takes an average of one month for a patient to notice improvement in symptoms after TUMT and 1.5 months to notice improvement after ILC. In fact, symptoms are typically worse for these therapies that heat or cook tissue, because of the swelling and necrosis that occurs in the initial weeks following the procedures. Prostatic stents often offer more immediate relief from obstruction but are now rarely used because of high adverse effect rates. Stents have the risk of migration from the original implant site (up to 12.5% of patients), encrustation (up to 27.5%), incontinence (up to 3%), and recurrent pain and discomfort. In published studies, these adverse effects necessitated 8% to 47% of stents to be explanted. Overgrowth of tissue through the stent and complex stent geometries have made their removal quite difficult and invasive.

Thus the most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Urinary Incontinence (UI)

Many women experience loss of bladder control following childbirth or in old age. This condition is broadly referred to as urinary incontinence (UI). The severity of UI varies and, in severe cases, the disorder can be totally debilitating, keeping the patient largely homebound. It is usually associated with a cystocele, which results from sagging of the neck of the urinary bladder into or even outside the vagina The treatments for UI include behavioral therapy, muscle strengthening exercises (e.g., Kegel exercises), drug therapy, electrical stimulation of the pelvic nerves, use of intravaginal devices and surgery.

In severe cases of UI, surgery is generally the best treatment option. In general, the surgical procedures used to treat UI attempt to lift and support the bladder so that the bladder and urethra are returned to their normal positions within the pelvic cavity. The two most common ways of performing these surgeries is through incisions formed in the abdominal wall or though the wall of the vagina.

A number of different surgical procedures have been used to treat UI. The names for these procedures include the Birch Procedure, Marshall-Marchetti Operation, MMK, Pubo-Vaginal Sling, Trans-Vaginal Tape Procedure, Urethral Suspension, Vesicourethral Suspension. These procedures generally fall into two categories, namely a) retropubic suspension procedures and b) sling procedures.

In retropubic suspension procedures, an incision is typically made in the abdominal wall a few inches below the navel and a network of sutures are placed to support the bladder neck. The sutures are anchored to the pubic bone and to other structures within the pelvis, essentially forming a cradle which supports the urinary bladder.

In sling procedures, an incision is typically made in the wall of the vagina and a sling is crafted of either natural tissue or synthetic (man-made) material to support the bladder neck. Both ends of the sling may be attached to the pubic bone or tied in front of the abdomen just above the pubic bone. In some sling procedures a synthetic tape is used to form the sling and the ends of the synthetic tape are not tied but rather pulled up above the pubic bone.

The surgeries used to treat UI are generally associated with significant discomfort as the incisions heal and may require a Foley or supra-pubic urinary catheter to remain in place for at least several days following the surgery. Thus, there exists a need in the art for the development of minimally invasive (e.g., non-incisional) procedures for the treatment of UI with less postoperative discomfort and less requirement for post-surgical urinary catheterization.

Cosmetic or Reconstructive Tissue Lifting and Repositioning

Many cosmetic or reconstructive surgical procedures involve lifting, compressing or repositioning of natural tissue, natural tissue or artificial grafts or aberrant tissue. For example, surgical procedures such as face lifts, brow lifts, neck lifts, tummy tucks, etc. have become commonplace. In many cases, these procedures are performed by creating incisions through the skin, dissecting to a plane beneath muscles and fascia, freeing the muscles, fascia and overlying skin from underlying structures (e.g., bone or other muscles), lifting or repositioning the freed muscles, fascia and overlying skin and then attaching the repositioned tissues to underlying or nearby structures (e.g., bone, periostium, other muscles) to hold the repositioned tissues in their new (e.g., lifted) position. In some cases excess skin may also be removed during the procedure.

There have been attempts to develop minimally invasive devices and methods for cosmetic lifting and repositioning of tissues. For example, suture suspension lifts have been developed where one end of a standard or modified suture thread is attached to muscle and the other end is anchored to bone, periostium or another structure to lift and reposition the tissues as desired. Some of these suture suspension techniques have been performed through cannulas or needles inserted though relatively small incisions of puncture wounds.

For example, barbed threads known as Aptos threads may be inserted through a hollow trocar and used to lift tissues of the face in a procedure that is performed commercially under the name Featherlift™ (KMI, Inc. 2550 West Rowland Anaheim, Calif. 92804).

Another barbed thread that is useable for minimally invasive cosmetic lifting procedures is marketed under the name Contour Threads™ (Surgical Specialties Corporation, 100 Dennis Drive Reading, Pa. 19606).

There remains a need for the development of new devices and methods that may be used for various procedures where it is desired to lift, compress, support or reposition tissues or organs within the body with less intraoperative trauma, less post-operative discomfort and/or shorter recovery times. Moreover, there is an opportunity to take advantage of aspects of anatomy and to employ structures configured to cooperate with such anatomy. In this way, an interventional site within a patient's body can be more easily accessed as well as heal more easily and completely and the body can more readily return to normal operation.

The present invention addresses these and other needs.

SUMMARY OF THE INVENTION

Briefly and in general terms, the present invention is directed towards an apparatus and method for deploying an anchoring assembly within a patient's body. The anchoring assembly can be configured to accomplish retracting, lifting, compressing, supporting or repositioning tissue within the body of a human or animal subject. Moreover, the apparatus configured to deploy the anchoring assembly as well as the anchoring assembly itself are configured to complement and cooperate with body anatomy. Further, the anchoring assembly may be coated or imbedded with therapeutic or diagnostic substances or such substances can be introduced into or near an interventional site by the anchor deployment device or other structure.

In a particular aspect, the present invention includes an integrated anchor delivery device that is capable of deploying at an interventional site an anchoring assembly including a first anchoring member attached by a connector to a second anchoring member. The anchor delivery device further includes an extendable and retractable needle assembly as well as structure to accomplish the deployment of the first anchoring member longitudinally through the needle assembly. The anchor delivery device additionally includes structure to attach the second anchoring member to the connector as well as cut the connector to a desired length.

In another aspect, structure of the anchoring assembly is designed to invaginate within or complement tissue anatomy to thereby facilitate healing and minimize infection risk. Moreover, the anchor delivery device includes structure to form desired angles between an extended position of the needle assembly relative to the device. Additionally, it is contemplated that a distal end portion of the anchor delivery device be configured to facilitate the testing of the effectiveness of positioning of an anchoring assembly. In this regard, the distal end portion is configured in a manner to mimic the effect a second anchoring member will have prior to its implantation.

In one embodiment, the anchor delivery device includes a handle assembly with a plurality of actuators or triggers attached thereto. A first actuator is associated with a body of the handle assembly and is operatively attached to the needle assembly and structure that advances the first anchoring member. A second actuator attached to the handle assembly is operatively associated with structure that accomplishes assembling first and second parts of the second anchoring member to each other and to the connector member. Also, the handle assembly is equipped with a third actuator that is configured in one contemplated embodiment, to effect the cutting of the anchoring assembly to a desired length and deployment of the structure at an interventional site.

In a specific embodiment, the anchor delivery device includes a generally elongate tubular housing assembly member extending distally from a handle assembly including a plurality of actuators. The proximal end of the handle assembly is equipped with mounting structure configured to receive a telescope or other endoscopic viewing instrument. A bore sized to receive the telescope extends distally through a body of the handle assembly and continues through an outer tubular cover member forming the generally elongate member. Housed within the tubular housing assembly are a telescope tube having an interior defining a distal section of the bore sized to receive the telescope, an upper tubular member assembly sized to receive a plurality of first components of the second anchor member and a needle housing configured to receive the needle assembly. Moreover, the generally elongate tubular housing includes a terminal end portion defined by a nose assembly which retains a plurality of second components of the second anchoring members.

Moreover, in a preferred embodiment the first anchor member includes a body having a generally tubular portion from which a first partial cylinder portion extends proximally. Attached to a midpoint of the body is a spring in the form of a second partial cylinder portion that is complementary to the first partial cylinder portion. Extending from the opposite end of the spring is a generally tubular collar. In a compressed configuration, the first anchor member defines a generally straight member and when unconstrained, the first anchor member forms a T-structure with the body defining the cross-member of the T-structure.

Further, in the preferred embodiment, the first part of the second anchoring member is embodied in a pin having a first distal end equipped with a pair of spaced arms and a second proximal end including grooves facilitating pushability. The arms of the first distal end are designed to receive the connector structure and to be placed into locking engagement with the second part of the second anchoring member. The second part has a generally tubular configuration and an internal bore sized to receive the first component.

The present invention also contemplates a number of alternative designs for the first and second anchoring members and connectors as well as structures for advancing and deploying the anchoring members and cutting the connector.

Additionally, it is contemplated that various embodiments can incorporate one or more sensors into the deployment device to facilitate proper positioning of the device and anchor deployment.

Moreover, various alternative methods of use are also contemplated. That is, in some applications of the invention, the invention may be used to facilitate volitional or non-volitional flow of a body fluid through a body lumen, modify the size or shape of a body lumen or cavity, treat prostate enlargement, treat urinary incontinence, support or maintain positioning of a tissue, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has a myriad of other potential surgical, therapeutic, cosmetic or reconstructive applications, such as where a tissue, organ, graft or other material requires retracting, lifting, repositioning, compression or support.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is an elevation view, depicting an integrated anchor deployment device;

FIG. 2A is a cross-sectional view, depicting a distal end portion of the device of FIG. 1;

FIG. 2D is a partial perspective view, depicting an elongate tube assembly of the device of FIG. 1 without the outer sheath and detached from the nose assembly and handle assembly;

FIG. 2E is a cross-sectional view, depicting a portion of a handle assembly of the device of FIG. 1;

FIG. 2F is a cross-sectional view, depicting further details of the device of FIG. 2C in addition to a cross-sectional view of a portion of the tubular housing assembly;

FIG. 3E is a perspective view, depicting a connector component with a plurality of first anchoring members of the anchoring assembly disposed thereon;

FIG. 3F is a perspective view, depicting an assembled anchoring assembly;

FIG. 4E is a perspective view, depicting yet another alternate embodiment of a distal component of an anchoring assembly;

FIG. 4F is a perspective view, depicting the distal component of FIG. 4E in a flipped configuration;

FIG. 5B is a cross-sectional view, depicting a portion of the anchor deployment device of FIG. 1 with the first actuator pivoted toward the handle assembly;

FIG. 5C is a cross-sectional view, depicting further internal mechanisms of the handle for accomplishing the advancement of the needle assembly;

FIG. 6E is a perspective view, depicting a needle and pusher assembly configured for side loading of an anchor component;

FIG. 6F is a perspective view, depicting an alternate embodiment of a pusher assembly;

FIG. 6G is a perspective view, depicting the pusher assembly of FIG. 6F and a complementary needle assembly;

FIG. 9N is a perspective view, depicting another embodiment of the second anchoring member;

FIG. 9O is a perspective view, depicting another embodiment of the second anchoring member;

FIG. 9P is a perspective view, depicting the embodiment of FIG. 9O in an assembled form;

FIG. 9Q is a perspective view, depicting another embodiment of the second anchoring member;

FIG. 9R is a perspective view, depicting the embodiment of FIG. 9Q in an assembled form;

FIG. 9S is a perspective view, depicting another embodiment of the second anchoring member;

FIG. 9T is a perspective view, depicting another embodiment of the second anchoring member;

FIG. 9U is a perspective view, depicting the embodiment of FIG. 9T in an assembled form;

FIG. 9AA is a perspective view, depicting another embodiment of the second anchoring member;

FIG. 9AB is a perspective view, depicting another embodiment of the second anchoring member;

FIG. 9AC is a perspective view, depicting the embodiment of FIG. 9AC in a compressed form;

FIG. 9AD is a perspective view, depicting another embodiment of the second anchoring member;

FIG. 9AE is a perspective view, depicting the embodiment of FIG. 9AD in a compressed form;

FIG. 9AF is a perspective view, depicting another embodiment of the second anchoring member;

FIG. 9AG is a perspective view, depicting another embodiment of the second anchoring member;

FIG. 9AH is a perspective view, depicting the embodiment of FIG. 9AG in an open configuration;

FIG. 9AI is a perspective view, depicting another embodiment of the second anchoring member in combination with a forming anvil;

FIG. 9AJ is a perspective view, depicting another embodiment of the second anchoring member in combination with a forming anvil;

FIG. 9AK is a perspective view, depicting another embodiment of the second anchoring member;

FIG. 9AL is a perspective view, depicting another embodiment of the second anchoring member;

FIG. 9AM is a perspective view, depicting the embodiment of FIG. 9AL in an open configuration;

FIG. 9AN is a perspective view, depicting another embodiment of the second anchoring member shown in its flattened configuration;

FIG. 9AO is a perspective view, depicting another embodiment of the second anchoring member shown in its flattened configuration;

DETAILED DESCRIPTION OF THE PREFERRED EMBODIMENTS

Figure 2B:
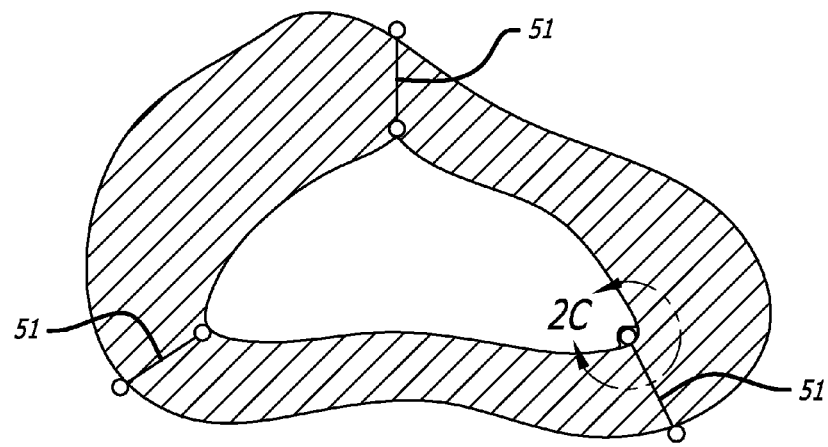
FIG. 2B is a cross-sectional view, depicting the implantation of anchoring assemblies at an interventional site.

Turning now to the figures, which are provided by way of example and not limitation, the present invention is embodied in a device configured to deliver anchor assemblies within a patient's body. As stated, the present invention can be employed for various medical purposes including but not limited to retracting, lifting, compressing, supporting or repositioning tissues, organs, anatomical structures, grafts or other material found within a patient's body. Such tissue manipulation is intended to facilitate the treatment of diseases or disorders. Moreover, the disclosed invention has applications in cosmetic or reconstruction purposes or in areas relating the development or research of medical treatments.

In such applications, one portion of an anchor assembly is positioned and implanted against a first section of anatomy. A second portion of the anchor assembly is then positioned and implanted adjacent a second section of anatomy for the purpose of retracting, lifting, compressing, supporting or repositioning the second section of anatomy with respect to the first section of anatomy. It is also to be recognized that both a first and second portion of the anchor assembly can be configured to accomplish the desired retracting, lifting, compressing, supporting or repositioning of anatomy due to tension supplied thereto via a connector assembly affixed to the first and second portions of the anchor assembly.

Referring now to FIG. 1, there is shown one embodiment of an integrated anchor delivery device 20. This device is configured to include structure that is capable of both gaining access to an interventional site as well as assembling and implanting an anchoring device within a patient's body. The device further includes structure configured to receive a conventional remote viewing device so that the steps being performed at the interventional site can be observed.

The integrated anchor delivery device 20 includes a handle assembly 22 and a tubular housing assembly 24 extending from the handle assembly 22. The handle assembly 22 is sized and shaped to fit comfortably within an operator's hand and can be formed from conventional materials.

The proximal end of the delivery device 20 includes a mount 26 for receiving an endoscope or telescope 28 or other imaging device. The mount 26 includes an internal bore (not shown) sized and shaped to receive the telescope 28. As indicated, the telescope 28 is intended to provide the operator with the ability to view the operation of the delivery device 20 at an interventional site.

The handle assembly 22 of the delivery device 20 also includes a plurality of activators or triggers associated with the handle assembly 22. The body 30 includes a first or upper portion 32 extending generally perpendicularly with respect to a second or lower portion 34. The second portion is intended to be sized and shaped to fit within the palm of an operator's hand. Pivotably affixed to the second portion 34 is a first actuator 36. Although it can come in a myriad of forms, the first actuator 36 includes a hooped portion sized and shaped to receive one or more fingers of the operator's hand. The hooped portion extends from an arm which is pivotably connected to the handle 22, the arm and hooped portion defining an acute angle with respect to the second portion 34 of the handle assembly 22 when inactivated. As will be described in more detail below, the first actuator 36 is operatively associated with a needle assembly and structure configured to advance and place a first component of an anchoring assembly at an interventional site.

A second trigger or actuator 38 is pivotably connected adjacent the first body portion 32. Although it can come in a myriad of forms, the second actuator 38 defines a generally finger-like projection and is positioned longitudinally distally from the body 30 with respect to the first actuator 36. The second actuator 38 also defines an acute angle respecting the second portion 34 of the handle assembly 22 and is sized and shaped to comfortably receive one or more fingers of the operator. Upon actuation, the second actuator 38 is configured to accomplish the assembly of an anchoring device by attaching a second anchor component to a connector affixed to the first anchor component.

A third trigger or actuator 40 is connected and configured to pivotably rotate with respect to a top side of upper body portion 30. Although it can come in a myriad of forms, in one embodiment, the third actuator 40 defines a relatively straight member with a rounded substructure formed at its free terminal end. In this way, the third actuator 40 is easily manipulated by a free digit of the operator's hand. The third actuator 40 rotates from a forward position where it forms an acute angle with the tubular housing assembly 24 to a rearward position where the member defines an obtuse angle with respect to the tubular housing assembly 24. In one embodiment, the third actuator 40 is intended to retract portions of the tubular housing assembly 24 as well as accomplish cutting the connector of the anchoring assembly and deploying the anchoring assembly at an interventional site.

As stated, the tubular housing assembly 24 extends from the handle assembly 22. In one aspect, the tubular housing assembly 24 is mounted to a front face of the upper portion 32 of the handle assembly 22 and extends parallel to a longitudinal axis of the upper portion 32. At its proximal end, the tubular housing assembly 24 includes a mount 42 from which an outer sheath 44 extends in a distal direction. The mount 42 includes one or more conventional stop cock assemblies 46 which provide fluid communication with an interior of the tubular housing assembly. One stop cock assembly 46 is intended to provide the anchor delivery device 20 with a continuous flow irrigation. Another stop cock 46 is contemplated to be used to accomplish a suction function through the device. Either of these assemblies can further be employed to deliver therapeutic or diagnostic substances to the interventional site. For example, in a procedure to treat a prostate gland, substances that cause the prostate to decrease in size such as 5-alpha-reductase inhibitors can be introduced at the treatment site. Other substances but not limited thereto, which may be introduced at the site include various phytochemicals, alpha-1a-adrenergic receptor blocking agents, smooth muscle relaxants and other agents that inhibit the conversion of testosterone to dihydrotestosterone.

A terminal end portion 48 of the tubular housing assembly 24 of the anchor deployment device 20 includes a nose assembly 50 shaped to provide an atraumatic surface as well as one which facilitates desired positioning of components of an anchoring assembly (See FIG. 2A). That is, by including structure that can mimic the ultimate position of a proximally oriented component of an anchoring assembly, an operator can test the effect of the anchoring assembly prior to implantation. Once the operator confirms that the subject anchoring component will be positioned as desired, the implantation of the anchor is then undertaken and accomplished.

Figure 2C:
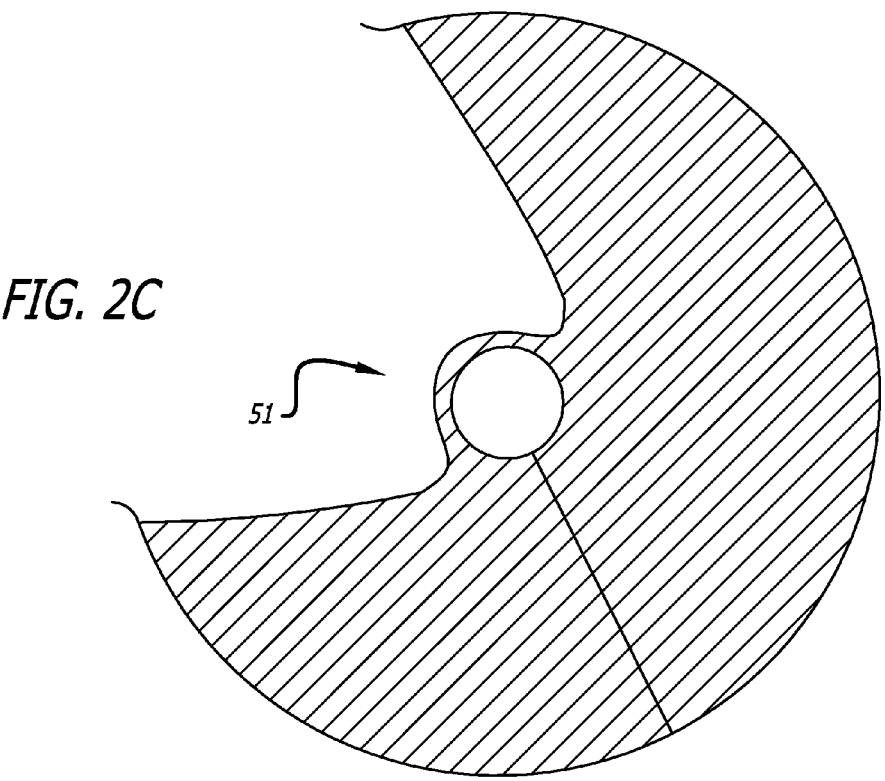
FIG. 2C is an enlarged view, depicting one anchoring component of the assemblies shown in FIG. 2B.

Once implanted, the anchoring assembly 51 (See FIGS. 2B and C) of the present invention accomplishes desired tissue manipulation or retraction as well as cooperates with the target anatomy to provide an atraumatic support structure. In particular, as shown in FIG. 2C, the shape and contour of the anchoring assembly 51 can be configured so that the assembly invaginates within target tissue, such as within natural folds formed in the urethra by the opening of the urethra lumen by the anchoring assembly. In fact, in situations where the anchor assembly is properly placed, wispy or pillowy tissue in the area collapses around the anchor structure. Eventually, the natural tissue can grow over the anchor assembly 51 and new cell growth occurs over time in the areas shown in FIG. 2C. Such cooperation with target tissue facilitates healing and avoids unwanted side effects such as calcification at the interventional site.

Furthermore, in addition to an intention to cooperate with natural tissue anatomy, the present invention also contemplates approaches to accelerate healing or induce scarring. Manners in which healing can be promoted can include employing abrasive materials, textured sutures, biologics and drugs.

It has been observed that placing the anchors at various desired positions within anatomy can extract the best results. For example, when treating a prostate, one portion of an anchor can be placed within an urethra. It has been found that configuring such anchors so that ten o'clock and two o'clock positions are supported or retained effectively holds the anatomy open and also can facilitate invagination of the anchor portion within natural tissue. This is particularly true in the regions of anatomy near the bladder and the juncture at which the ejaculatory duct connects to the urethra.

Additionally, the terminal end portion 48 (FIG. 2A) includes a plurality of spring biased, vertically stacked ring anchor components 52 strategically positioned with respect to telescoping structure of the tubular housing assembly for the purpose of assembling an anchoring device. As will be apparent from further description below, the stacked anchor component 52 is one of two parts which form a second anchor component. To accomplish the biasing of the anchor components 52, a leaf spring 54 is placed in apposition with the anchor component 52 that is at the bottom of the stack of components. Internal molded walls and bosses of the nose assembly 48 form a space to both receive the stacked anchor components 52 as well as provide an area to retain the leaf spring 54 and provide a base structure against which force supplied by the leaf spring can be generated and transmitted to the anchor components 52.

As can be seen from FIG. 2A, terminal end portions of an upper tubular member 56, a needle housing 58 and a telescope housing 60 are positioned within the nose assembly. Referring now to FIG. 2D, one can better see the internal components forming the tubular housing assembly. For representation purposes, the outer sheath 44 is not depicted in FIG. 2A and the internal components of the tubular housing assembly are shown separate from the nose assembly and handle assembly. As shown, the upper tubular member 56, the needle housing 58 and telescope housing 60 extend longitudinally. The outer sheath (not shown in FIG. 2A) covers a substantial length of each of the upper tubular member 56, needle housing 58 and telescope housing 60. Each of these structures also include internal bores, the upper tubular member 56 sized to slideably receive a pusher assembly (described in more detail below) and the needle housing 58 sized to slideably receive a needle assembly 58 (also described in more detail below). Further, the telescope housing 60 is sized to receive a conventional telescope (not shown), which in one approach, fills the entire space provided by the internal bore of the housing 60. A cross-sectional view of a portion of the tubular housing assembly attached to the handle assembly 22 (with the nose assembly removed) is shown in FIG. 2F.

Turning now to FIGS. 2E and 2F, the internal components of the handle assembly will be described. In one preferred embodiment, the handle assembly 22 houses a needle assembly advancement and retraction subassembly 66 that interacts with the movement of the first actuator. The first actuator includes a projection 68 extending through the housing assembly 22 and is placed in operative association with the advancement and retraction subassembly 66.

The needle assembly advancement and retraction subassembly 66 includes an outer collar 70 configured about an inner collar 72. Configured between the outer collar 70 and an internal front surface 74 of the handle assembly 22 is a first compressor spring 75. Placed within the outer collar 68 and between the inner collar 72 and an internal front surface 76 is a second compression spring 77. Additionally, attached to the outer collar 70 is a lock assembly 78 which rotates between locked and unlocked positions.

While the first actuator is in an open position (See FIG. 1), the compression springs 75, 76 assume expanded configurations (See FIGS. 2E and F). Also, the lock assembly 78 is in a disengaged or unlocked configuration. It is at this stage that the needle assembly (described below) is in its retracted state and housed completely within the needle housing 58.

Figures 3A, 3B:
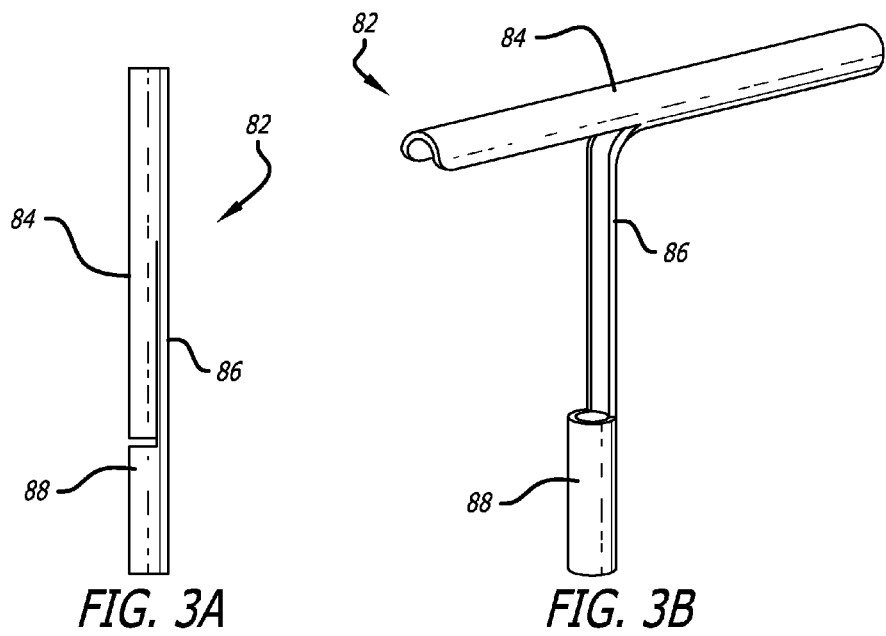
FIG. 3A is a perspective view, depicting a first anchoring member of an anchoring assembly of the present invention shown in a substantially straight configuration.
FIG. 3B is a perspective view, depicting the first member of FIG. 3A in a deployed or flipped configuration.

One preferred embodiment of a first or distal component 82 is shown in FIGS. 3A and 3B. In an unconstrained configuration, the first component forms a generally T-configuration (FIG. 3B). When constrained within an anchor delivery device, the first component defines a substantially straight member (FIG. 3A). While the component can be formed from a number of materials and manufactured using various conventional approaches, it is contemplated that the component 82 be cut from a nitinol tube using a laser. Using a superelastic material such as nitinol provides the component 82 with the resiliency to transform between a flipped T-configuration and a straight configuration.

As shown, the first component 82 includes a first portion 84 which at one end defines a cylindrical structure and at the other a partial cylindrical structure. When unconstrained, this first portion 84 forms a T-bar or top of the first component 82. A complementary partial cylindrical structure forms a midsection or second portion 86 of the first component 82 and operates as a spring to accomplish the flipping of the first portion 84 between constrained and unconstrained configurations. When the component is in its constrained, straight form, the second portion is positioned adjacent the first portion 84. A third portion 88 is also cylindrical in shape and extends from the second portion 86 away from the first portion 84 of the first anchor component 82. The third portion 88 slides freely with respect to a connector, the connector being attached to the first portion 84 and a second anchor component as will be described below.

Figures 3C, 3D:
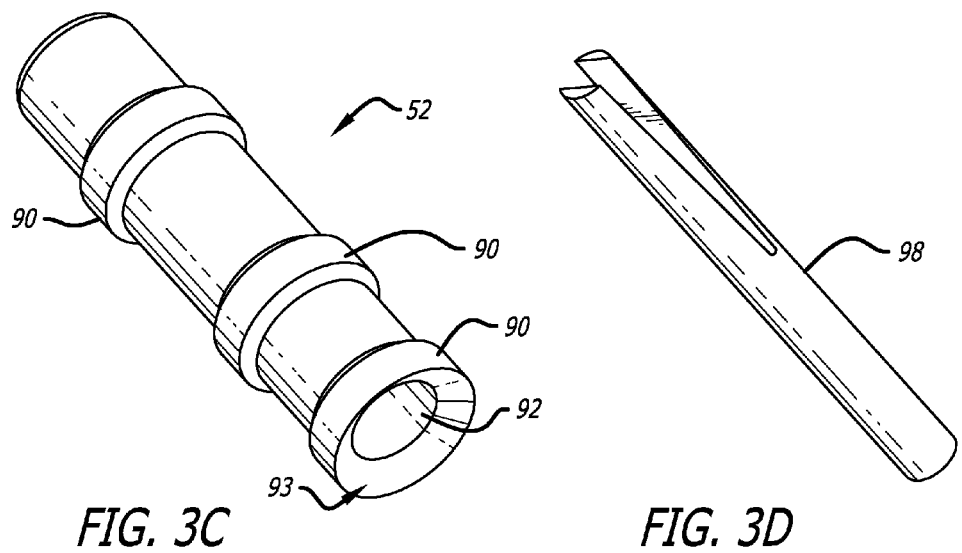
FIG. 3C is a perspective view, depicting a first component of a second anchoring member of an anchoring assembly of the present invention.
FIG. 3D is a perspective view, depicting a second component of a second anchoring member of an anchoring assembly of the present invention.

One part of the second anchoring component 52 is best seen in FIG. 3C (previously depicted as stacked anchor components in FIG. 2A). This component is generally cylindrical in form and includes integrally formed rings 90 spaced along an outer surface of the device, such spacing can be varied as necessary for a particular purpose. The device further includes a internal bore 92 which extends the entire length thereof. A proximal end 93 of this part of the second anchoring component 52 includes an opening to the internal bore 92. The opening to the bore 92 is surrounded by a first ring 90 and is sized to receive in a locking arrangement the connector which will attach the first anchor 82 to the second anchor component 52. Additional rings 90 are spaced longitudinally along an outside surface of the component.

As shown in FIG. 3D, a second part 98 of the second anchoring component 52 can be sized and shaped to both engage a connector and to lockingly engage the first part. Although various forms of the second part 98 are contemplated and described below, in one approach, the second part is generally cylindrical and includes a pair of spaced arms, the outer profile being sized to fit within the internal bore 92 of the first part.

The connector 94 (See FIG. 3E) can be formed from any material which provides the desired holding force between first and second components. In one preferred embodiment, the connector is formed from conventional suture material for example monofilament polyester. In a preferred embodiment, the connector 94 is monofilament polyethylene terephthalate (PET). The suture material embodies desirable flexibility as well as tensile strength. The monofilament PET size 2-0 is preferred because of high tensile strength when tensioned and high column strength to push the series of parts 82 through and out the needle. In addition, the monofilament helps reduce or eliminate the possibility of infection. As such, when used as a connector 94, such material can be flexed at sharp angles to access various anatomical structures and surfaces and can also be relied upon to transmit necessary forces between the first and second anchoring assemblies. One or more first anchor components 82 can be affixed along a length of the connector 94. Further, various approaches can be employed to attach a first anchor component 82 to the connector. For example, the components can be affixed by an adhesive or can include tabs or other structure which is deformed into a locking arrangement with the connector 94. Moreover, the anchor component 82 can simply be crimped directly to the connector 94 or the connector itself can include structure which is complementary to that of the component to accomplish affixation. It may be advantageous to employ an assembly capable of handling a connector equipped with a plurality of anchor components spaced along the connector since such a system has the ability to assemble and deliver multiple anchor assemblies without needing to reload.

One embodiment of a completely assembled anchoring assembly 92 is depicted in FIG. 3F. In the embodiment shown, the assembly includes a single first anchor component 82. In certain applications, however, it may be desirable to employ a device having a plurality of spaced first anchor components. Such spacing can be varied as desired for a particular application.

It is also contemplated that the completed anchor assembly is formed from components which are held together magnetically. For example, the first anchor component 82 and the second anchor component 52, 98 can be held in place through magnetism and without the need of a connector. In such an approach, either both or one of the anchor components can be a magnet.

Moreover, as can be seen from FIG. 3F, the second anchor component embodies the first part 52 which can be deployed from the stacked group of such members housed within the terminal end portion 48 of the tubular housing assembly 24 (See FIG. 2A), as well as the second part 98 which, by operation of the anchor delivery device 20 (described below), lockingly engages the first part 52.

As previously mentioned, a completed anchor assembly 96 can be employed to manipulate tissue and other structure found within a patient's body for various purposes. In order to do so, the first anchoring component 82 is initially positioned in an apposition with a first body structure, such as the outer surface of the prostate capsule, and the second anchoring component assembly (52, 98) is placed against a second body structure, such as the inner surface of the urethra, the connector 94 holding the desired spacing between the two body structures to accomplish the desired manipulation.

Additionally, it is contemplated that all components of the anchor assembly 96 or selected portions thereof (of any of the anchor assemblies described or contemplated), may be coated or embedded with therapeutic or diagnostic substances (e.g. drugs or therapeutic agents). Again, in the context of treating a prostate gland, the anchor assembly 96 can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector 95 can for example, be coated with a polymer matrix or gel coating which retains the therapeutic or diagnostic substance and facilitates accomplishing the timed release thereof. Additionally, it is contemplated that bacteriostatic coatings can be applied to various portions of the anchoring assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is contemplated. In one such approach, the deployment device includes a reservoir holding the gel substance and through which an anchoring device can be advance to pick up a desired quantity of therapeutic or diagnostic gel substance.

Figure 3G:
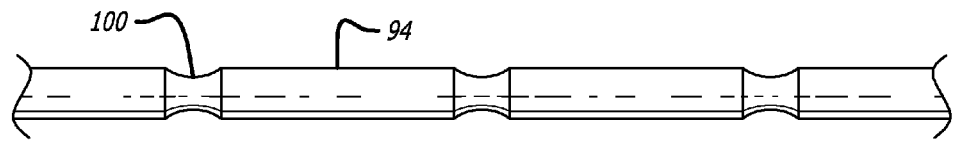
FIG. 3G is a perspective view, depicting a coined connector.
Figure 3H:
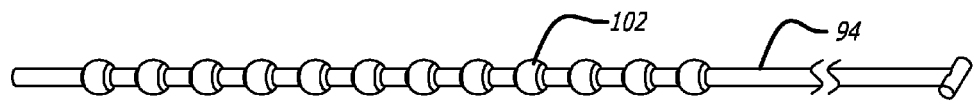
FIG. 3H is a perspective view, depicting a connector equipped with raised portions.

The connector 94 can have associated therewith various structures which facilitate the attachment of anchoring structures. Although intended for the first anchor component 82, such structure can also be used for the second anchor component 52, 98. In one approach (FIG. 3G), the connector 94 is coined 100 in a manner that provides structure to which an anchor member can form a locking engagement. As shown in FIG. 3H, structure facilitating a locking engagement with anchor structure also can also be in the form of a ball-chain 102. Furthermore, a connector 94 can be equipped with crimped metal or other structures 104 for this purpose.

Figures 4A, 4B:
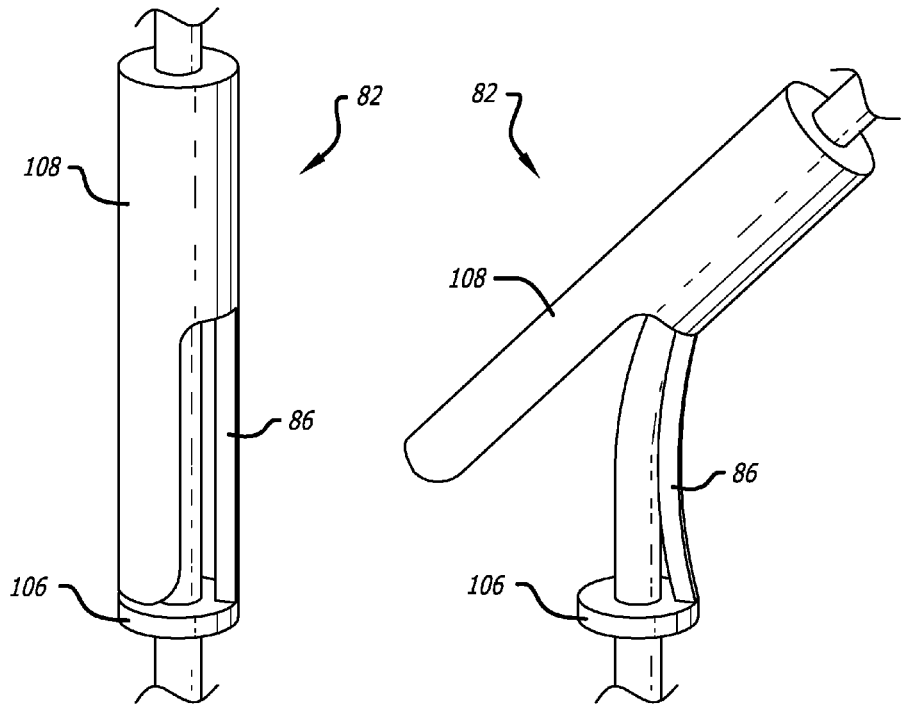
FIG. 4A is a perspective view, depicting an alternate embodiment of a distal component of an anchoring assembly.
FIG. 4B is a perspective view, depicting the distal component of FIG. 4A in a flipped configuration.
Figure 4C:
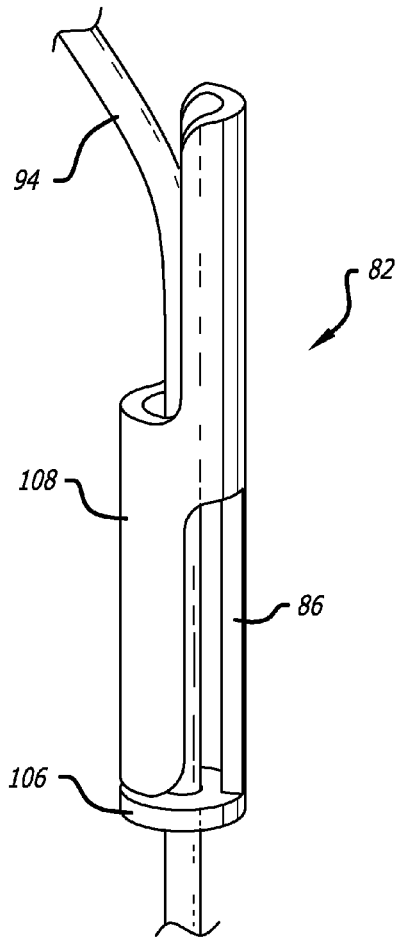
FIG. 4C is a perspective view, depicting another alternate embodiment of a distal component of an anchoring assembly.
Figure 4D:
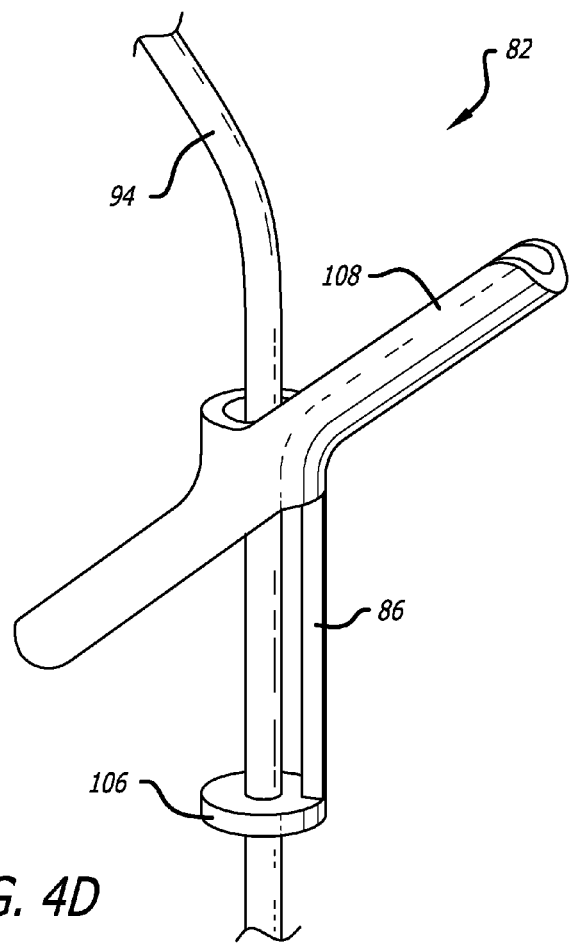
FIG. 4D is a perspective view, depicting the distal component of FIG. 4C in a flipped configuration.

Turning now to FIGS. 4A-4I, various alternatives of first anchor components 82 are presented. In particular, those depicted in FIGS. 4A-I each include a structure which flips to assume an angled or generally lateral configuration when the component is unconstrained. In a constrained configuration, these components define a generally cylindrical profile (as shown in FIG. 4A).

Moreover, each of the various alternative embodiments can be formed from conventional materials. In one aspect, the components can be formed by laser cutting a nitinol tube. However, it is to be recognized that other materials and manufacturing approaches are also contemplated for example EDM of stainless steel.

For example, the connector shown in FIG. 4A includes a proximally oriented collar 106 which is intended to be slid along a connector as the second portion flips or rotates. A spring member 86 defines a bar arm which forms a bridge between the collar 106 and a second portion 108 which flips or rotates with respect to the collar 106 when the device is unconstrained as shown in FIG. 4B. In another approach (FIGS. 4C and 4D), the spring member 86 forms a bridge between the collar 106 and a second portion 108 which includes a pair of members which in a constrained configuration extend in opposite directions along the connector 94 and when unconstrained, form a T-bar structure. In yet another approach (FIGS. 4E-F), the anchoring component 82 can include a pair of collars 106 configured between which are first and second springs 86. Attached to each spring 86 is a second portion 108, each of which assume angled or lateral positions to thereby form an overall cross-like structure when unconstrained. Like the other embodiments, the component defines a generally straight, cylindrical structure when constrained.

Figure 4G:
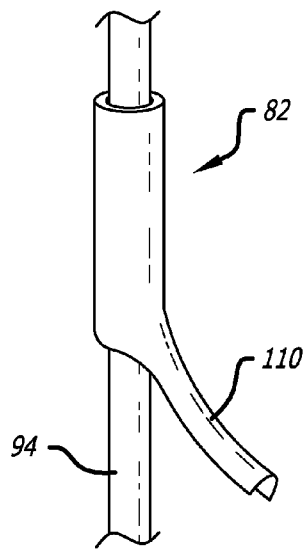
FIG. 4G is a perspective view, depicting a distal component of an anchoring assembly with a first embodiment of a tail section.
Figure 4H:
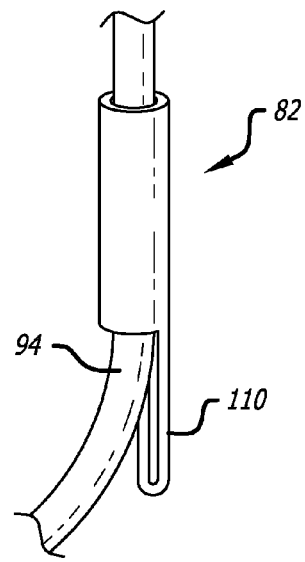
FIG. 4H is a perspective view, depicting a distal component of an anchoring assembly with a second embodiment of a tail section.
Figure 4I:
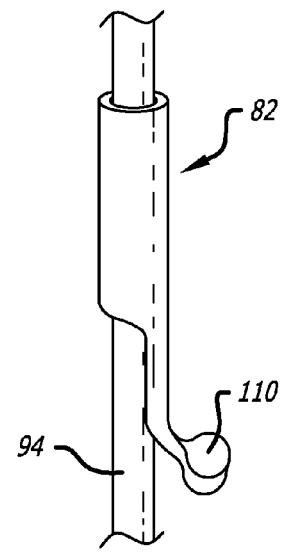
FIG. 4I is a perspective view, depicting a distal component of an anchoring assembly with a third embodiment of a tail section.

FIGS. 4G-I depict further embodiments of structures that can be employed as first anchoring components 82 or alternatively, can be used solely as structures for advancing the anchoring assembly sub-components within the anchor delivery device or a patient's body. Each of these depicted structures include various forms of tails 110 which can be employed to advance the anchor components 82 through direct engagement with a terminal end of a pusher assembly (not shown) or for registering within slots formed in a pusher assembly. These tails also help to flip, turn or angle the component 82 relative to connector 94. One embodiment of the tail (FIG. 4G) is a simple extension of a partial cylindrical member which is bent away from the connector 94. Another approach (FIG. 4H) involves a long tail 110 which is folded against the connector 94 and yet another approach (FIG. 4I) involves a tail 110 that rather than folded against the connector includes a narrowed section which is bent away from the connector and terminates to assume a beaver tail-like shape.

Figure 4J:
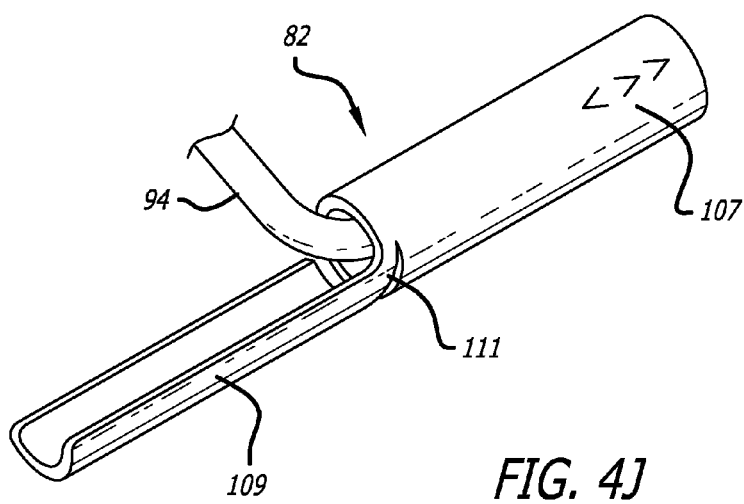
FIG. 4J is a perspective view, depicting yet another embodiment of a distal component.

With reference now to FIG. 4J, yet another embodiment of a first anchoring component 82 is presented. In this embodiment, the first anchoring component includes a full tube portion 107 connected to a half tube portion 109 by a coiled portion 111. The device can further include suture attachment points formed along the full tube portion 109. The coiled portion 111 provides flexibility in multiple planes and thus facilitates pushing the device through bends or angles formed in the deployment device employed to deliver the first anchoring component 82.

Figure 5A:
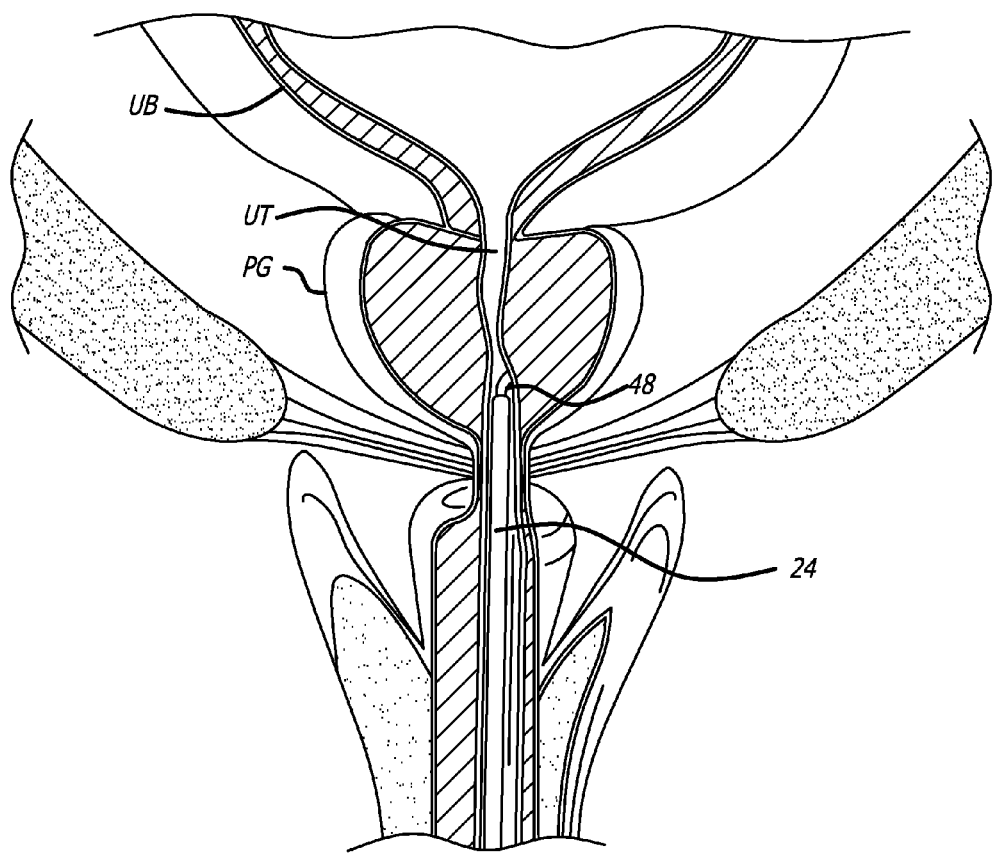
FIG. 5A is a cross-sectional view, depicting a first step of treating a prostate gland using the present invention.
Figure 5D:
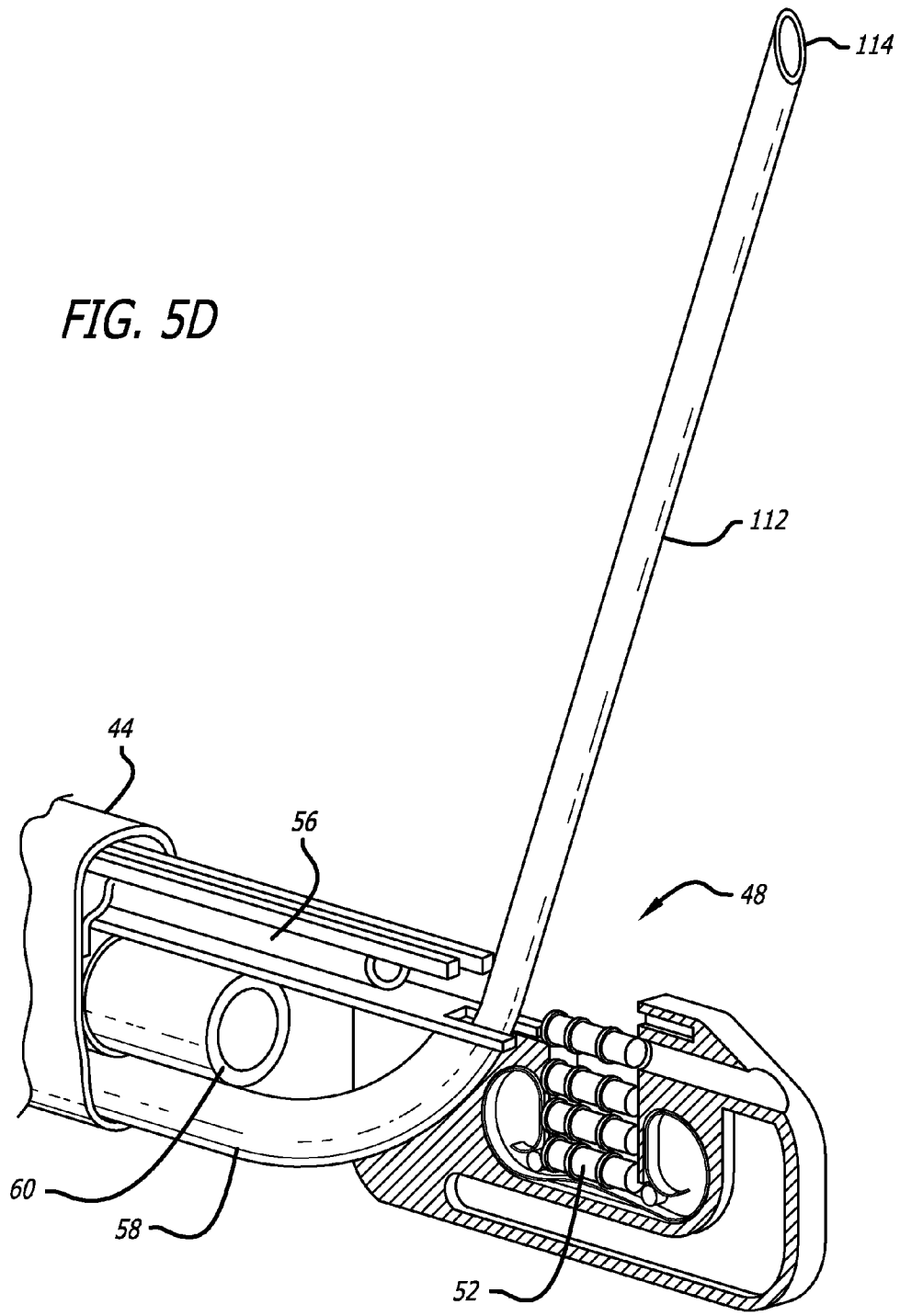
FIG. 5D is a perspective view, depicting the distal end portion of the anchor deployment device and the lateral advancement of a needle assembly.
Figure 5E:
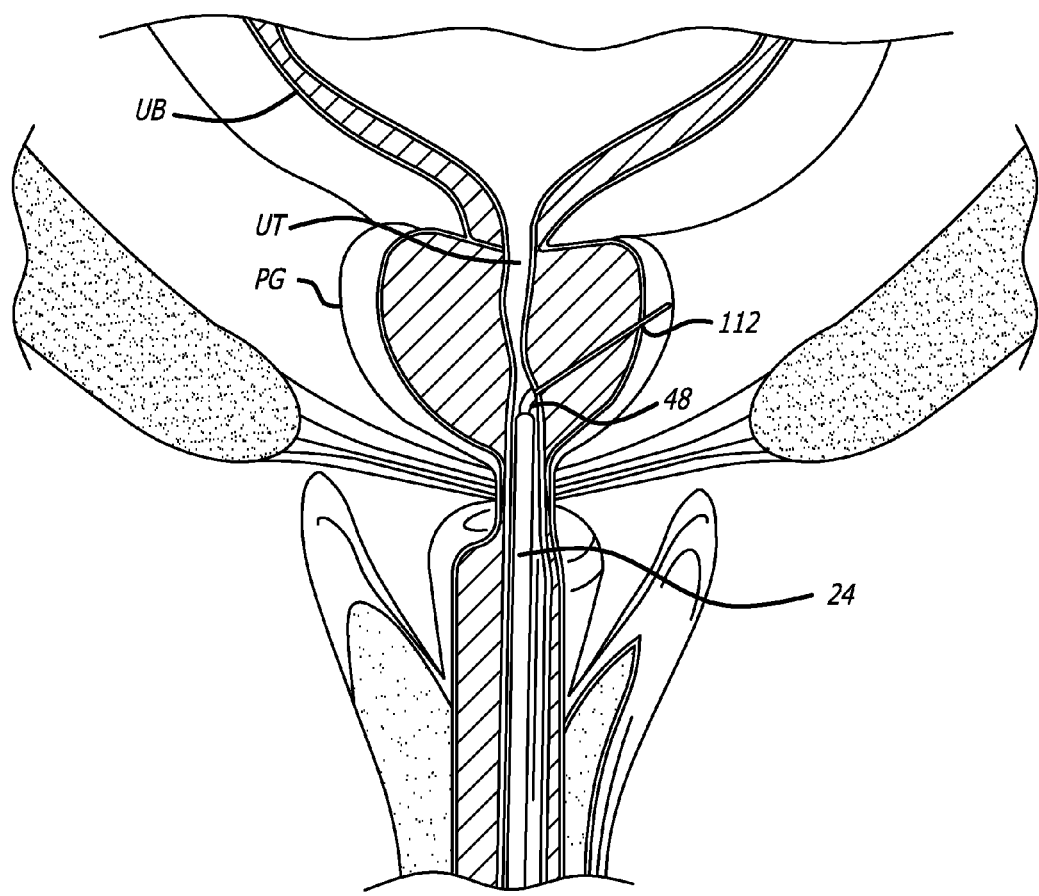
FIG. 5E is a cross-sectional view, depicting a second step of treating a prostate gland using the present invention.

In a first step to deliver and deploy an anchoring assembly for the purpose of manipulating tissue or other anatomical structures, the telescope device is employed to view the positioning of the device 20 at the interventional site, for example, the tubular housing assembly 24 of the device is inserted into the penis of a patient and advanced until the distal end 48 is adjacent an interventional site in the urethra (UT) adjacent the bladder (UB; See FIG. 5A). It has been found that a mechanical solution to the treatment of BPH such as that of the present invention, can be more compatible with patients recovering from prostate cancer compared to energy-based solutions. Furthermore, the present invention also contemplates steps for sizing the anatomy. As it relates to BPH treatment, the present invention also involves the placement of an ultrasonic or other device in the patient's body, such as in the rectum, to measure the necessary depth of insertion of the anchor deployment device within the patient's body. This information can be used to set or create a depth stop for the needle assembly so that the operator can readily determine whether desired sections of the patient's anatomy have been accessed. After so positioning the deployment device within the patient, the first actuator 36 of the delivery device 20 (See FIG. 1) is then caused to be pivoted towards the handle assembly 22. Doing so causes the needle assembly 112 to be advanced distally and then laterally through a terminal end of the needle housing 58. The lock assembly 78 retains the needle in the advanced configuration (See FIGS. 5C and D). It is to be noted that the lock assembly 78 can be configured to automatically unlock or to require manipulation to disengage from a locking position. In a procedure to treat the prostate gland (PG) the needle assembly 112 is advanced through the prostate gland to a first implant position (See FIG. 5E). Moreover, it is to be recognized that first forked member 113 is translatable longitudinally either by hand or through action of a trigger or activator. In FIG. 5D, the first forked member 113 is shown retracted to more easily represent other system components, but in use, at this stage of deployment, the member 113 is contemplated to be in an advanced position into engagement with slot 115. Further, it is to be understood that for ease of system representation, second forked member 119 is shown in a truncated form, in that at this stage of deployment the terminal end of the member 119 extends beyond the vertical stack of second anchor components 52, thereby holding the stack in a staged configuration. Finally, the present invention also contemplates a single member replacing the forked members 113, 119 depicted, such a part of member 56 which can have portions which provide the function accomplish by the terminal ends of the members 113, 119.

Notably, the needle assembly 112 has a generally tubular shape and terminates with a sharp point 114. A lumen extending the length of the needle assembly 112 is sized to receive both components of the anchoring assembly as well as structure for advancing the assembly through and out of the terminal end 114. Although various materials are contemplated, the needle assembly 112 is intended to be formed from resilient material such as nitinol or other materials or polymeric substances. Moreover, although various angles are contemplated, in one approach the needle housing 58 includes a distal section angled such that the needle projects at angles approaching or at 90 degrees with respect to a longitudinal axis of the tubular housing assembly 24.

Figure 5F:
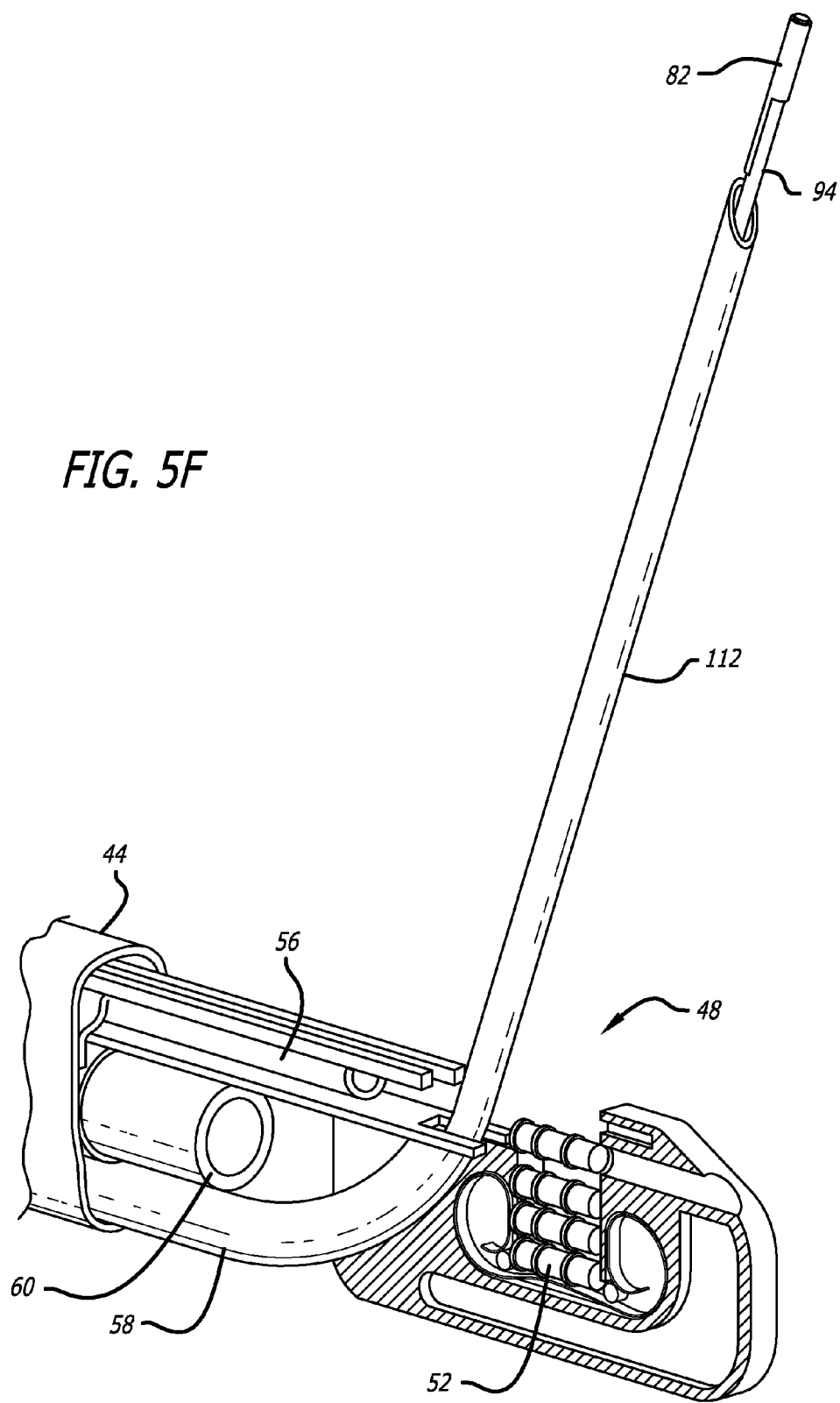
FIG. 5F is a perspective view, depicting the partial retraction of the needle assembly.
Figure 5G:
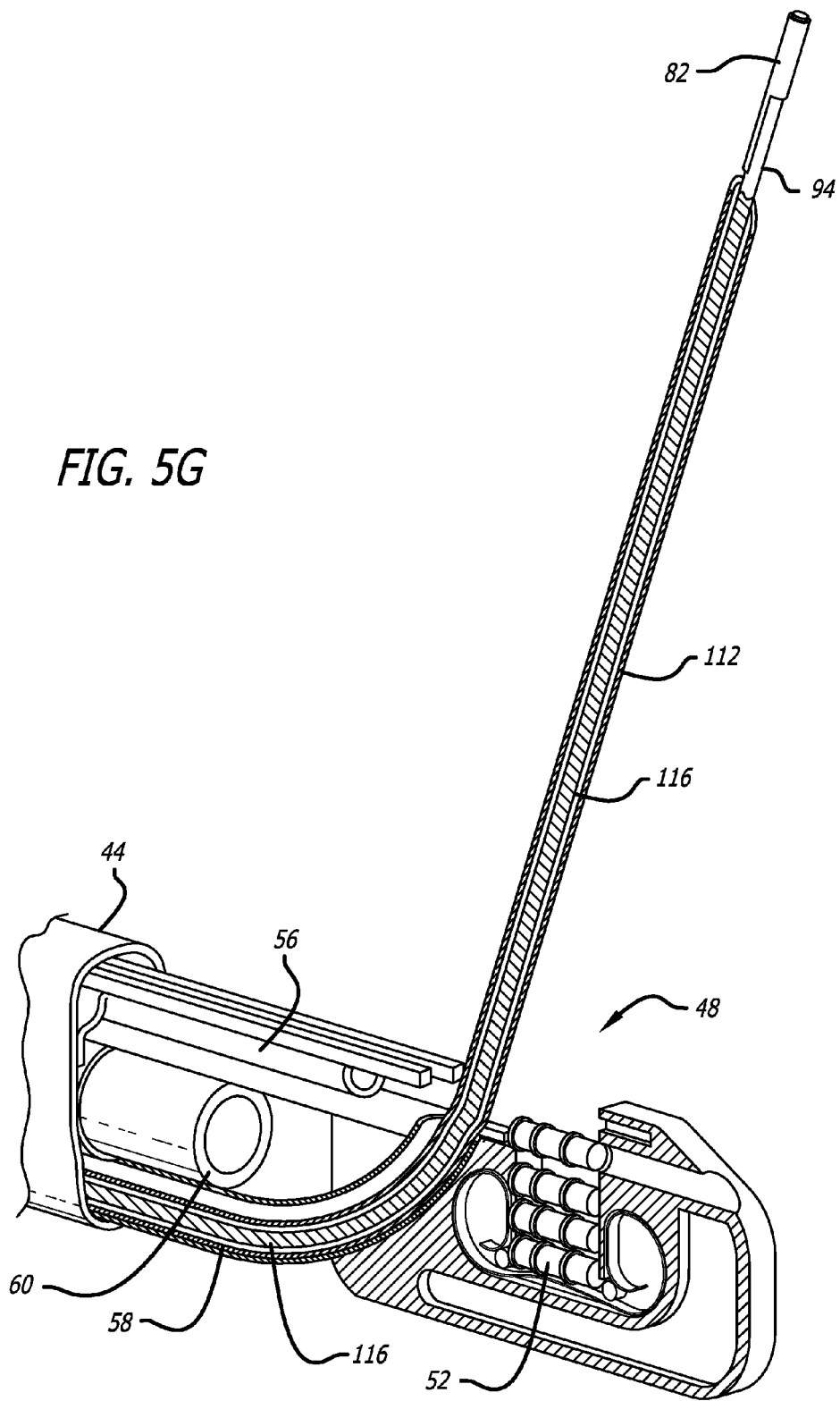
FIG. 5G is a cross-sectional view, depicting the assembly of FIG. 5D.

Once access is made at an interventional site to target tissue or anatomical structure and the first actuator is manipulated to advance the needle assembly 114 to a desired position, the actuator is further manipulated to release the lock assembly 78 as well as to cause the internal compression springs to retract the needle assembly. Note that the position of the first actuator 36 will return to the open position (See FIGS. 1, 2E and 2F). The result of this action is depicted in FIGS. 5F, G, H, I and J. (Again, note that member 113 and 119 are shown in retracted or truncated forms in FIGS. 5F, G and H for clarity of representation.) That is, as the needle assembly 112 is retracted, the first anchoring component 82 and connector 94 remain in an advanced configuration (FIGS. 5I and J). It is at this stage that the first anchoring component has been positioned as desired against a first anatomical body structure (See FIG. 5J).

Figure 3I:
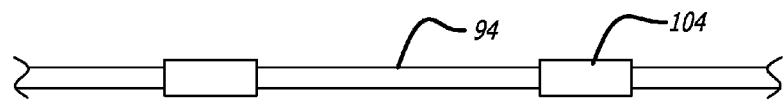
FIG. 3I is a perspective view, depicting a connector equipped with crimped components.

Contemporaneously with the retraction of the needle assembly 112, is the withdrawal of the structure used to advance the first anchoring component 82 and connector structure 94 within the needle housing 58. In one embodiment (See FIG. 5K), the advancing structure is in the form of a pusher assembly 116. The pusher 116 can assume a generally cylindrical tube formed form a metallic or polymeric material which is sized and shaped to directly engage the first anchoring component 82. Moreover, the pusher 116 could define a solid elongate member of polygonal or circular cross-section. Also, it can be configured to directly engage the connector 94 directly or other structure formed on the connector 94 (See FIGS. 3G-I). In another aspect, the pusher can be sized to surround the first anchor member 82 and to engage a tail (See FIGS. 4G-I) for example, of the anchor member once the pusher is pulled proximally with respect to the anchor member. When the pusher 116 initially surrounds the anchor member (or other structure formed directly on the connector 94), the tail is held in compression, only to be released to extend laterally from the connector when the pusher is moved proximally. In this way, the pusher assembly 116 can both be withdrawn when desired and advance the anchor member 82 and connector structure 94 when necessary. In another approach, the tail can be held in compression by the internal surface of the needle (not shown).

Figure 5H:
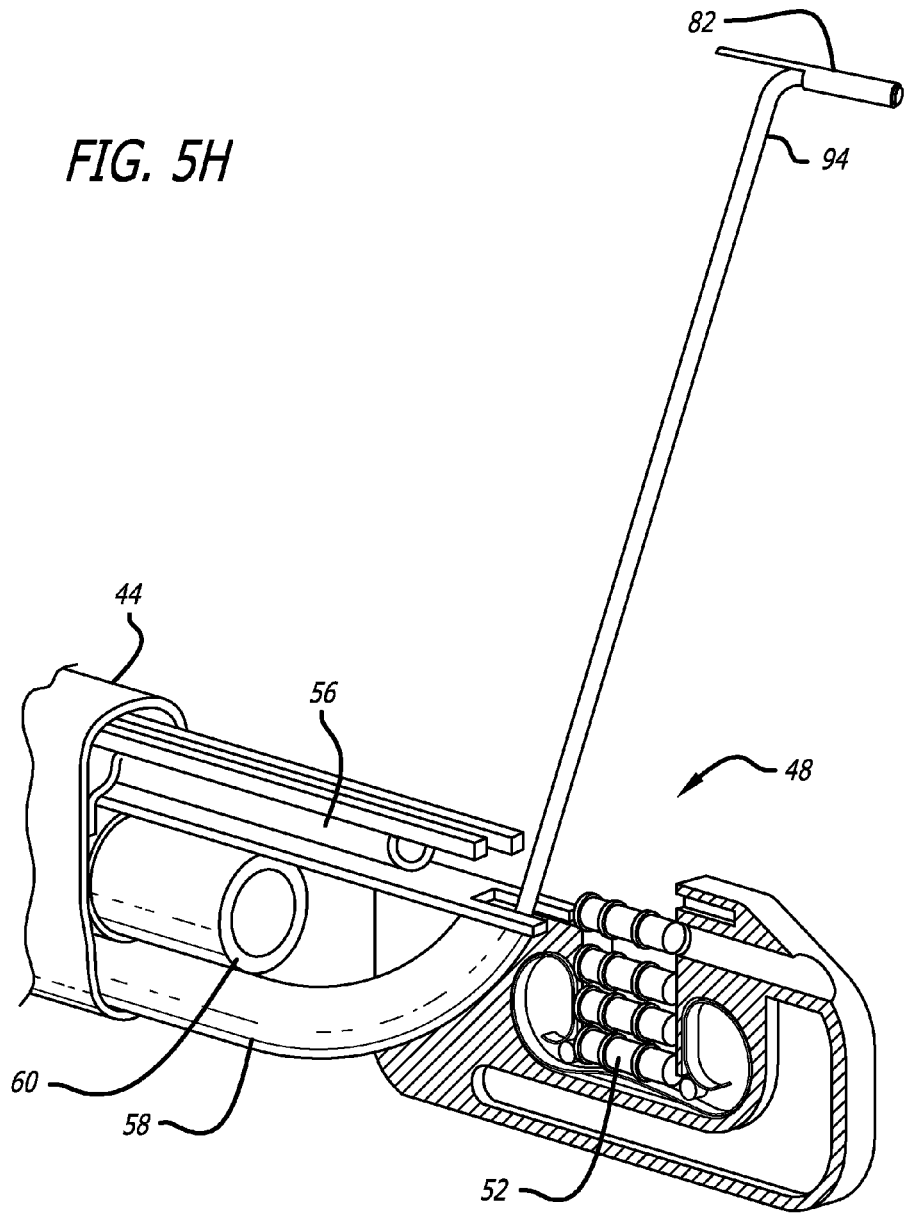
FIG. 5H is a perspective view, depicting the complete retraction of the needle assembly.
Figure 5I:
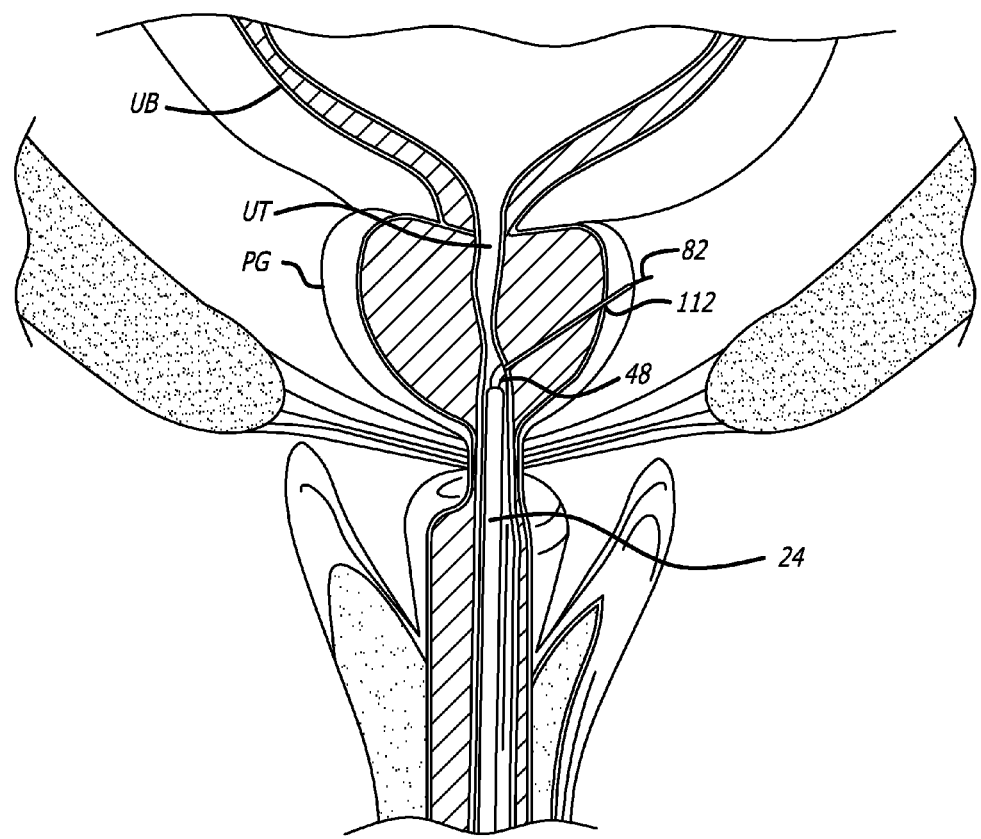
FIGS. 5I and 5J are cross-sectional views, depicting further steps of a method of treating a prostate gland using the present invention.
Figure 5J:
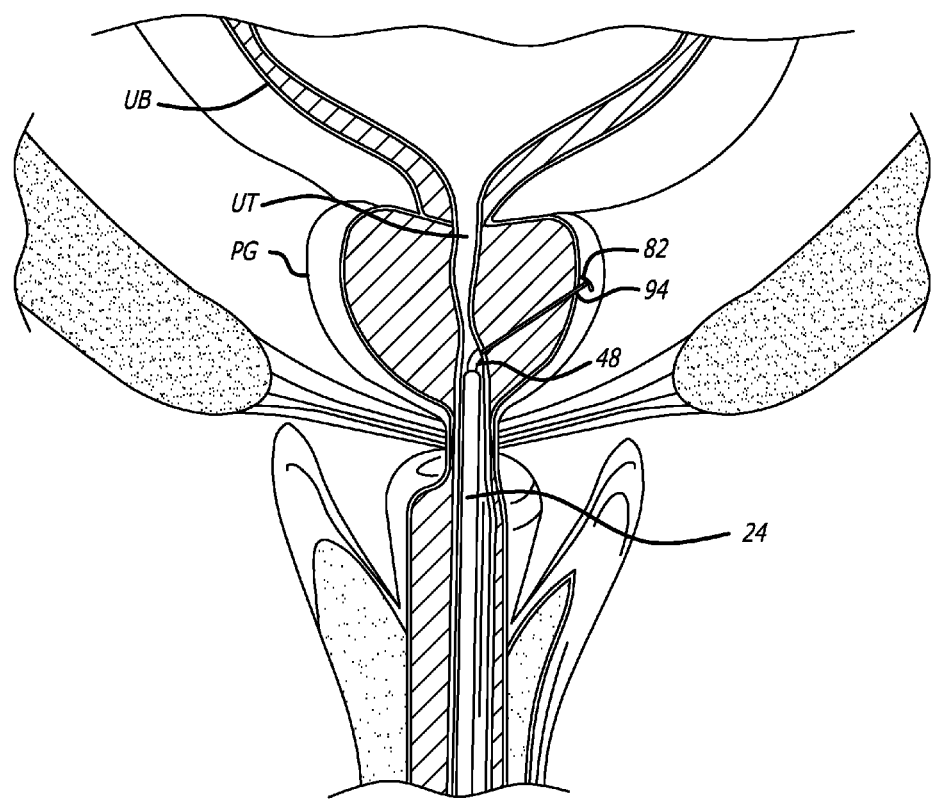
Figure 5K:
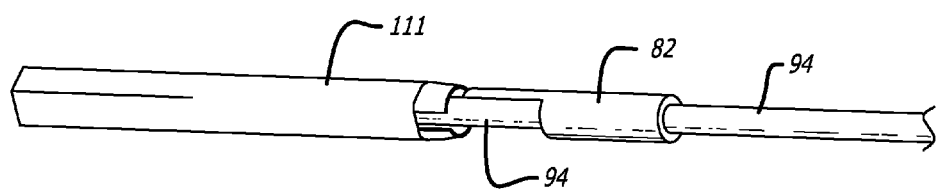
FIG. 5K is an enlarged perspective view, depicting one embodiment of a feeding mechanism for the distal component.

As shown in FIG. 5H, the complete withdrawal of the pusher 116 and needle assembly 112 exposes the full length of connector anchoring structure for use in ultimately manipulating anatomical structures. Such complete withdrawal involves both the pusher 116 and needle assembly to be housed completely within the needle housing 58.

Figure 6A:
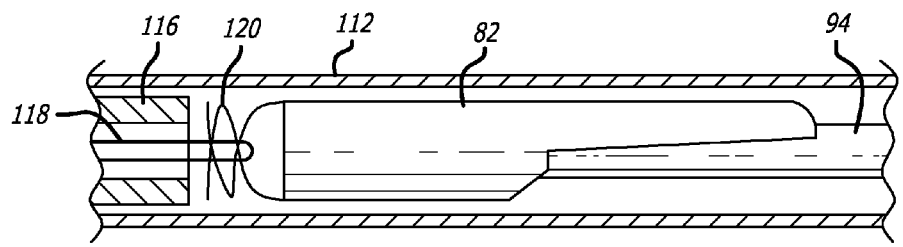
FIG. 6A is an elevation view, depicting one alternative approach for controlling the advancement and deployment of an anchor component.
Figure 6B:
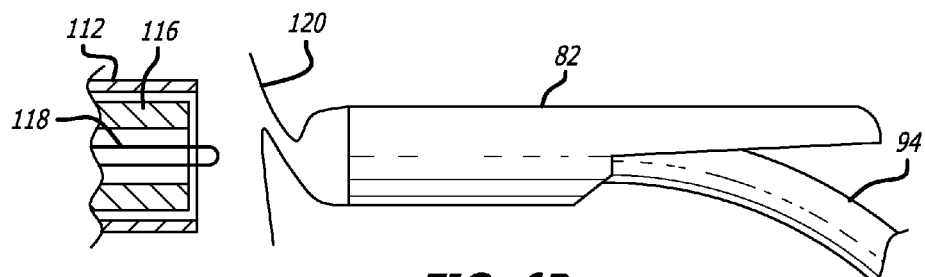
FIG. 6B is an elevation view, depicting a first configuration of the anchor of FIG. 6A after release from the advancement substructure.

Alternative approaches for advancing anchor components within the anchor delivery device 20 are contemplated. That is, rather than having a pusher assembly which surrounds an anchoring component and relies upon engagement with a tail structure of an anchoring component or other structure projecting from the connector member, other structure can be employed to provide the ability to push and pull an anchor component. In one such approach (See FIGS. 6A-C), the delivery device can be equipped with a pusher member 116 in combination with a pull wire 118. The pusher member 116 in this approach remains proximal an anchor member 82 to be advanced along the delivery device. Such anchor members 82 can be placed in a position distal the pusher, for example, by being released from a cartridge configured distal to the pusher position or the delivery device can be a single use apparatus.

Figure 6C:
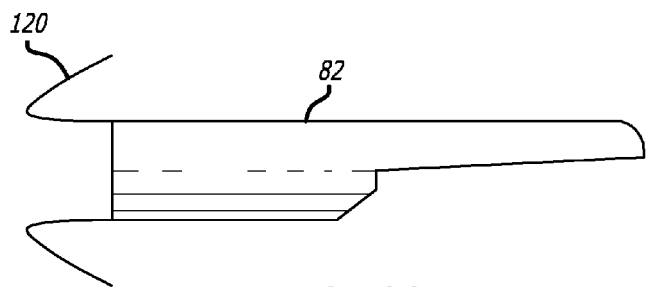
FIG. 6C is an elevation view, depicting a second configuration of the anchor of FIG. 6A after release from the advancement substructure.
Figure 6D:
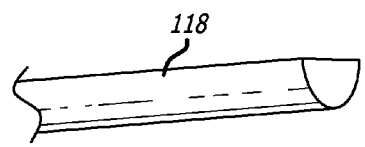
FIG. 6D is a perspective view, depicting an alternate embodiment of a pusher device.

The anchor member 82, in turn, can include a proximal portion characterized by a pair of elastically or plastically deformable arms 120 which in a first configuration are held to the pull wire 118 and in a second configuration, are released from the pull wire 118. Accordingly, the pusher member 116 is advanced with respect to the pull wires 118 to cause the arms 120 to become disengaged from the pull wire. In the embodiment shown in FIGS. 6A and B, the arms 120 are plastically deformable whereas the arms 120 of the anchor member 82 of FIG. 6C are elastically deformable. The elastically deformable arms 120 can be formed from resilient material such as nitinol. The plastically deformable arms 120 on the other hand can be made from less resilient material.

Further alternative embodiments of pusher members 116 are shown in FIGS. 6D-G. A pusher member 118 having a D-shaped cross-sectional profile is contemplated for certain uses. Such a profile enables the pusher member 116 to be placed along side the anchor component 82 and connector 94 assembly, a distal portion of the D-shaped configuration engaging complementary structure on the connector assembly.

Also contemplated is a pusher assembly 116 which includes a side opening 122 in communication with a lumen extending through the pusher 116 (See FIG. 6E). Threaded through the side opening 122 is a distal portion of the anchor component 82 and connector 94 assembly. In this arrangement, the distal-most anchor component 82 is placed against the terminal end of the pusher member 116 to accomplish advancement of the anchor component 82 and connector 116 assembly as the pusher 116 is extended distally.

In yet another approach, as shown in FIGS. 6F and G, the pusher member 116 includes a terminal end 123 configured with a D-shaped profile suited to engage and advance an anchor/connector assembly 94. A proximal section of the pusher 116 is equipped with a plurality of spaced detents or cavities 124 sized and shaped to receive anchor components 82 or other structure formed on the connector 94. In this approach also, the pusher member 116 is configured to reside longitudinally adjacent the anchor/connector assembly 82, 94. Advancement of the anchor/connector assembly 82, 94 is accomplished through an engagement between certain of the anchor/connector assemblies 82, 94 and the cavities 124.

Figure 7A:
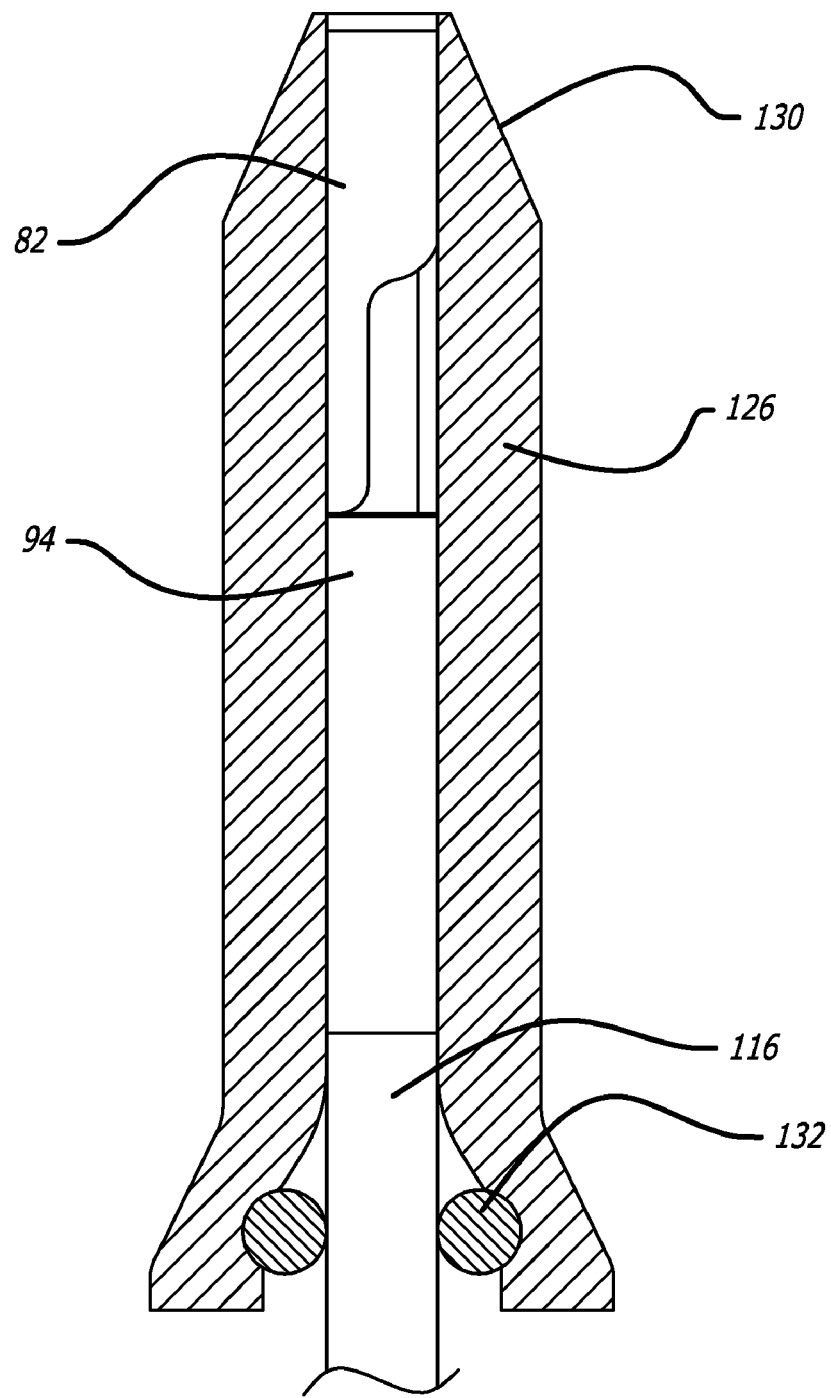
FIG. 7A is a cross-sectional view, depicting an anchor loaded in a protective cover.
Figures 7B, 7C:
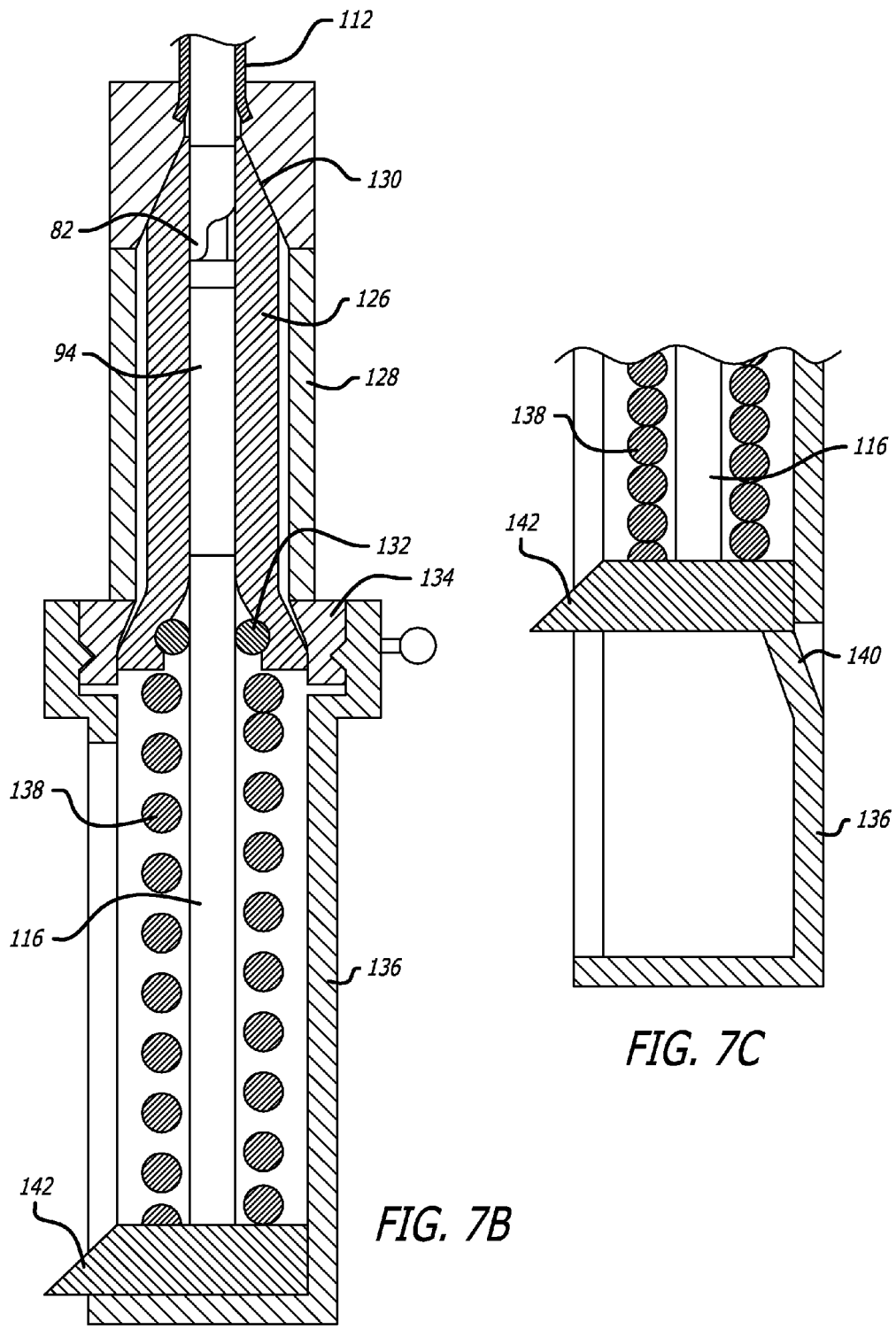
FIG. 7B is a cross-sectional view, depicting a pusher cartridge in a loaded position.
FIG. 7C is a cross-sectional view, depicting the cartridge of FIG. 7A in an anchor deployed position.

Various measures can be taken to ensure proper loading of a first anchor member 82 within an anchor delivery device. In a first step, the anchor member 82 is loaded within an anchor protection cover 126 (FIG. 7A). A pusher member 116 is configured proximal to the connector 94 of the first anchor member 82 to accomplish advancement of the first anchor member 82 into and through the needle assembly 112 (See FIGS. 7B and C). This subassembly is insertable within a delivery device bay 128. A distal portion 130 of an interior of the delivery device bay is equipped with a conical taper configured to receive a distal complementary portion of the anchor protection cover 126 thereby accomplishing the centering of anchor member within the delivery bay 128. An internal lumen extends the length of the protection cover 126 and the cover 126 includes a ring seal 132 placed within a proximal end thereof. The ring seal 132 functions to hold the cover 126 on a pusher member 116.

The delivery device bay 128 can further include a bayonet lock mount 134 that couples a spring loaded cartridge 136 to the delivery device bay 128. Housed within the cartridge is a compression spring 138 configured about the pusher member 116. The spring cartridge 138 can also include a lock-out structure 140 which operates to limit the tension placed on the anchor member 82 and connector 94 until the needle 112 is withdrawn sufficiently from the interventional site to avoid damage from the needle 112 inadvertently engaging the anchor/connector assembly 82,94. That is, the pusher 116 includes a proximal end configured with an anchor deployment tab 142 that engages the lock-out structure 140, prohibiting the compression spring 138 from applying tension to the anchor/connector assembly 82, 94 before the needle assembly 112 is clear of the interventional site.

Figure 7D:
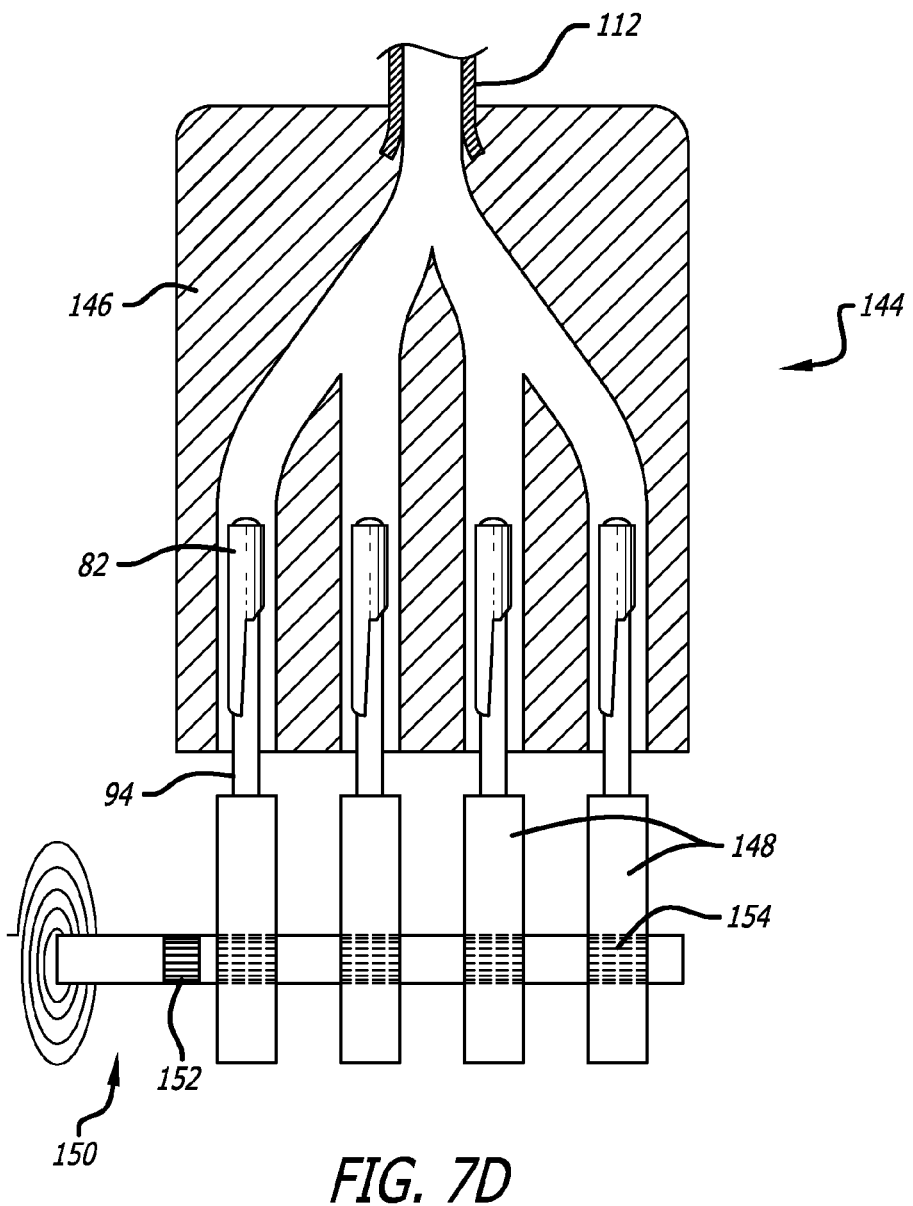
FIG. 7D is an elevation view, depicting an anchor cartridge assembly.

In another contemplated variation (FIG. 7D), the anchor delivery device can be fashioned with a multi-shooter anchor cartridge assembly 144. One feature of this approach is the involvement of a manifold 146 including four entries which feed into a lumen extending into a needle assembly 112, each entry configured to receive one anchor/connector assembly 82,94. Proximal sections of the connector 94 are configured into spools 148 which are driven by a torsional spring drive shaft 150. The drive shaft 150 is in turn, configured with complementary teeth structures 154 formed on each spool. The assembly further includes structure (not shown) adapted to cause lateral movement in the driveshaft 150 so that its teeth 152 indexes from spool to spool 148 to thereby turn the spools 148 and advance the anchor members 82 within the needle assembly 112. Once the anchors 82 are advanced through the needle 112, the torsion spring retracts excess connector 94 length and clears the needle 112 for the next anchor member 82.

Figure 7E:
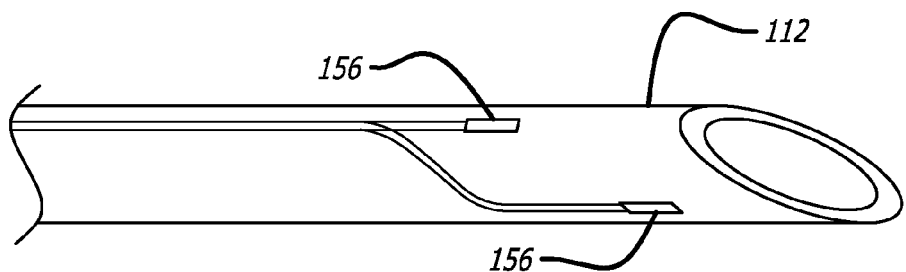
FIG. 7E is a perspective view, depicting a needle assembly equipped with a sensor.

It is further contemplated that in certain embodiments, the anchor delivery device can include the ability to detect forces being applied thereby or other environmental conditions. Although various sections of the device can include such devices, in the depicted structure of FIG. 7E, sensors 156 can be placed along the needle assembly 112. In this way, an operator can detect for example, whether the needle has breached the target anatomical structure at the interventional site and the extent to which such breaching has occurred. Other sensors which can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Figure 8A:
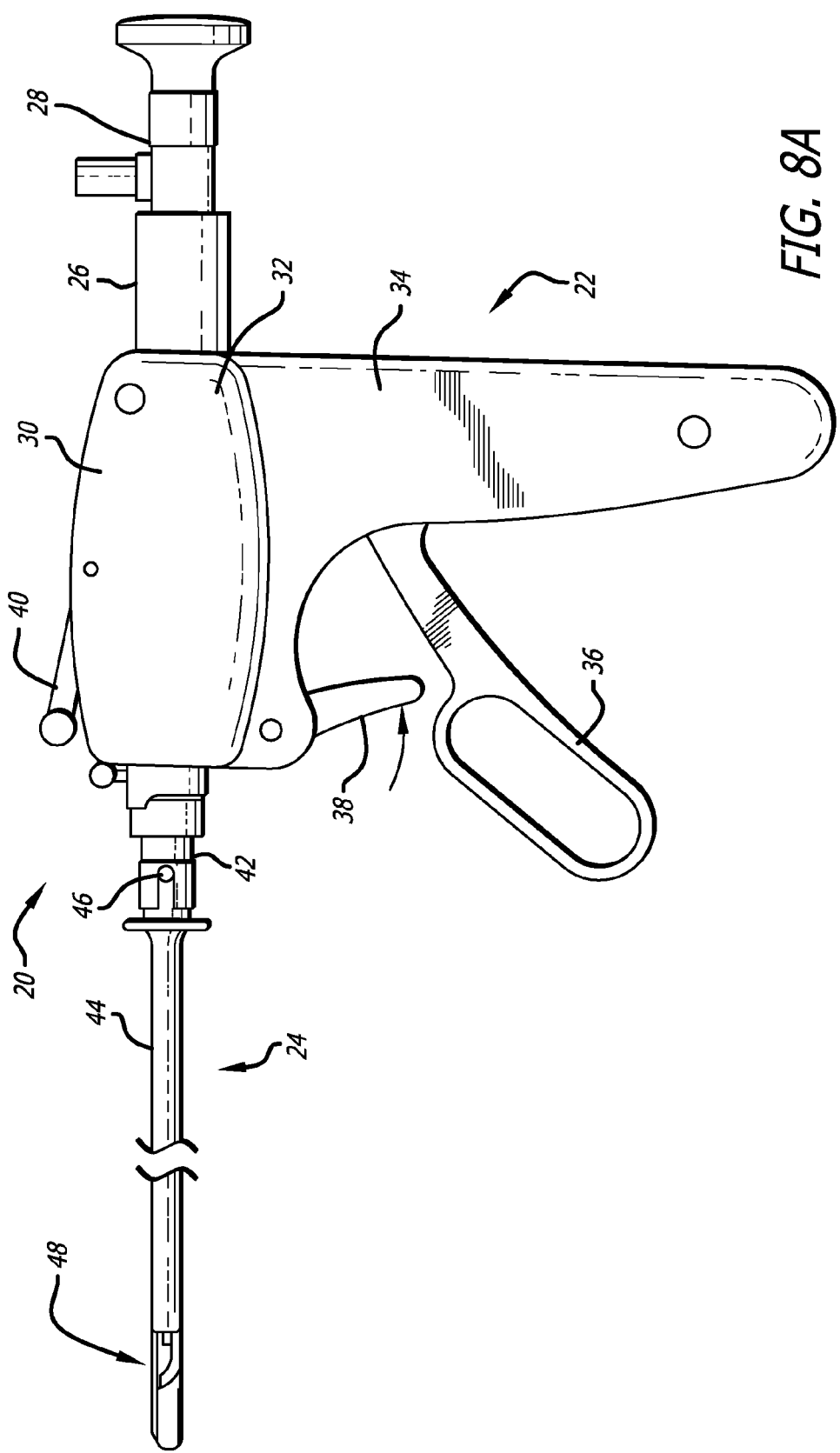
FIG. 8A is a cross-sectional view, depicting the pivoting of the second actuator with respect to the handle.
Figure 8B:
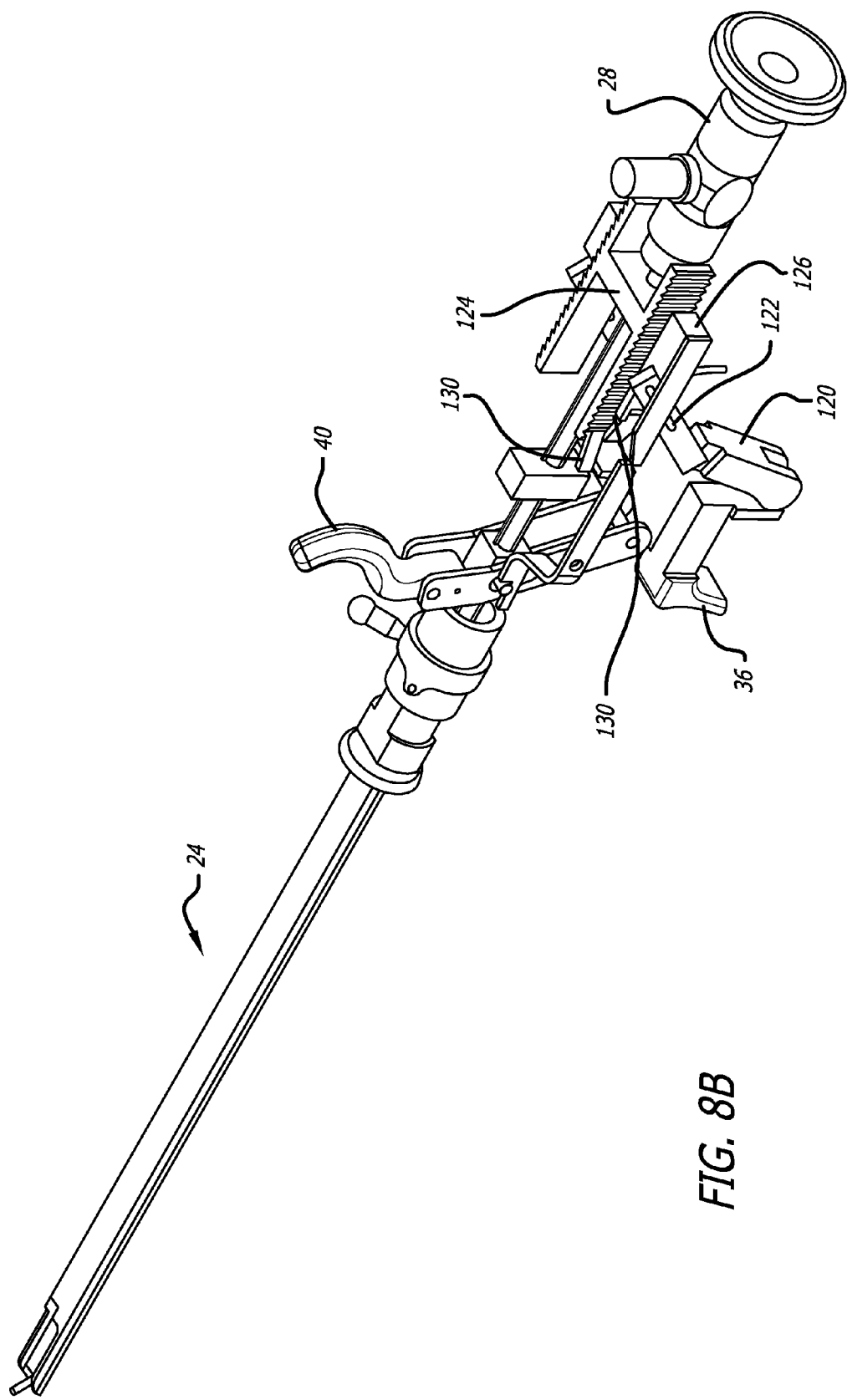
FIG. 8B is an isometric view, depicting internal components operatively associated with the second actuator and with other components of the anchor deployment device removed.

In a next stage of anchor deployment, with reference to FIGS. 8A-E, after the first actuator 36 is completely released thereby effecting the complete withdrawal of both the needle assembly 112 and pusher member 116, the second actuator 36 is pulled proximally to initiate the assembly of the second or proximal anchor member 52,98 (See FIG. 8A). Note that in FIGS. 8C, D and E, member 113 is shown in its advanced or forward position within slot 115, wherein member 119 is shown with its terminal end truncated. With reference to FIG. 8B, which depicts internal components of the integrated anchor assembly associated with the second actuator (other structure being removed for better understanding), as the second actuator 36 is depressed, it engages a lever assembly 120 including a slotted portion 122 to drive a rack assembly 124 distally. The slotted portion 122 of the lever assembly 120 provides the lever with the ability to both rotate with respect to a mount 126 of the rack assembly 124 as well as advance the mount 126 as well as the rest of the rack assembly 124 distally. Various pawls 130 are provided to releasably lock the rack assembly 124 in desired stages of advancement. It is to be recognized, however, that various other approaches to manually locking or unlocking structure for advancing components of the second anchor assembly are contemplated. In the depicted embodiment, the rack assembly 124, is in turn, connected to a telescoping pusher member which is configured to engage a second part o the second or proximal anchor assembly.

Figure 8C:
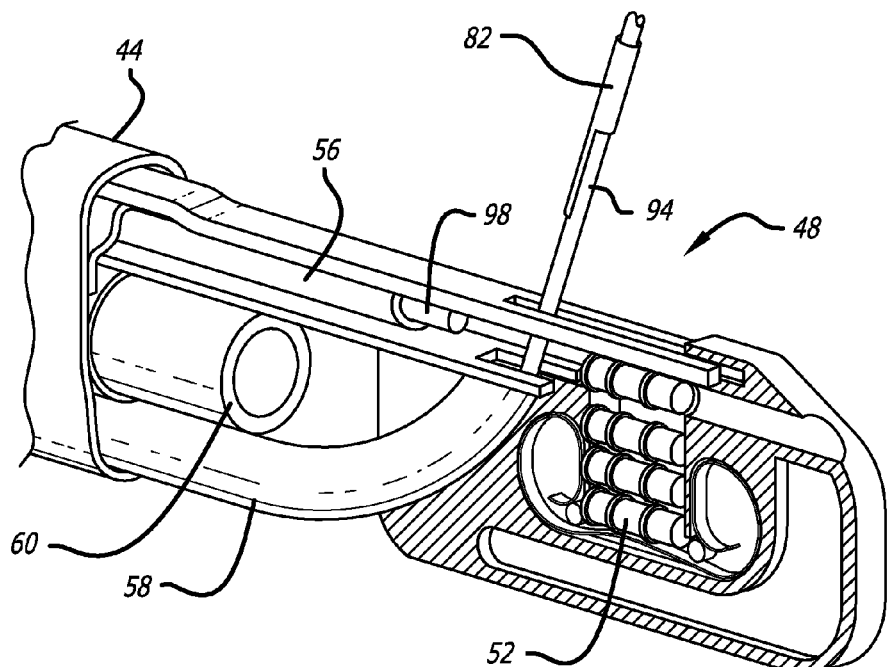
FIG. 8C is a partial cross-sectional view, depicting a distal end portion of the integrated anchor deployment device of FIG. 8A.
Figure 8D:
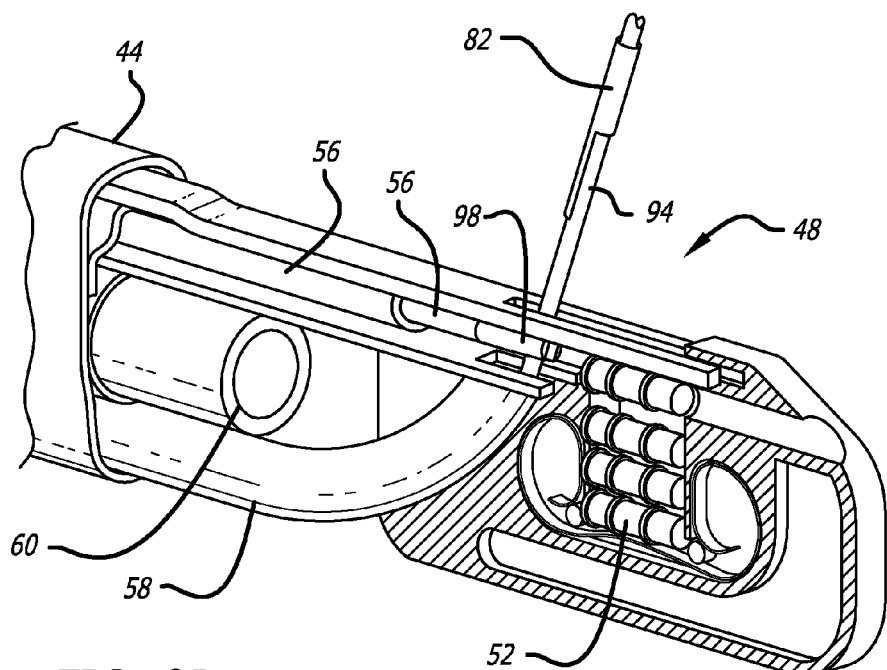
FIG. 8D is a partial cross-sectional view, depicting the deployment device of FIG. 8C with a second component of the second anchoring member being advanced toward a first component of the second anchoring member.
Figure 8E:
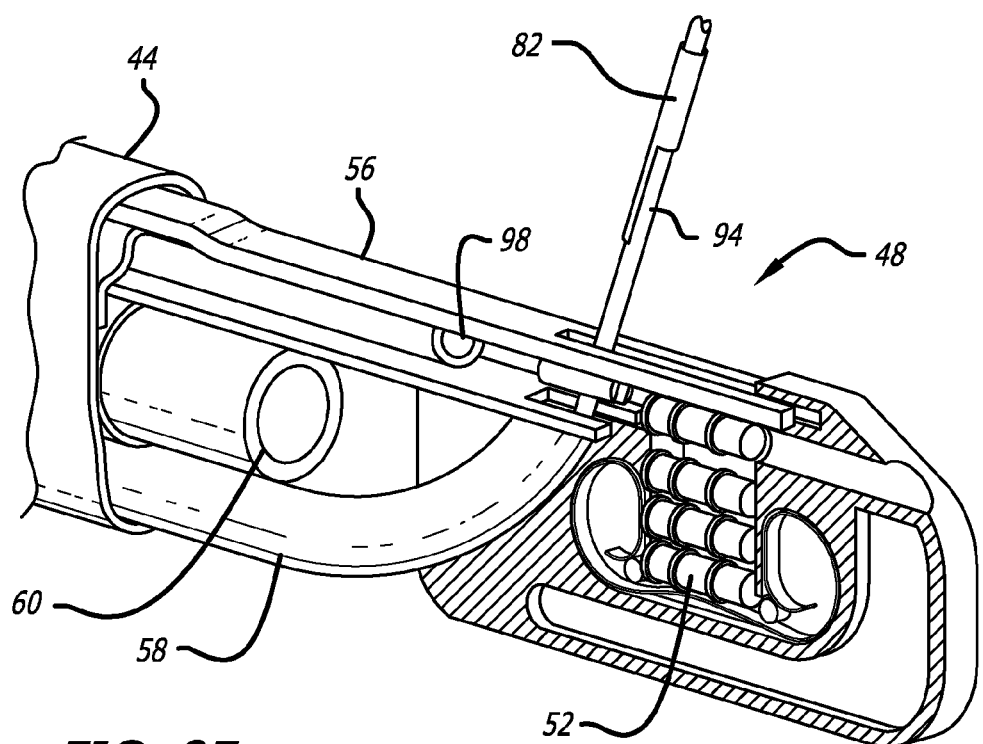
FIG. 8E is a perspective view, depicting the deployment device of FIG. 8B with the second component completely advanced into locking engagement with the first component.

As shown in FIGS. 8C-E, depressing the second actuator 38 causes a pusher 157 to advance a second part 98 of the second or proximal anchor member to be advanced towards and into locking engagement with the first part 52 of the second anchor member. As the second part 98 is advanced, it captures the connector structure 94 and retains it in a locking engagement between the first 52 and second 98 parts.

It is at this stage that the connector 94 is severed to thereby accomplish the formation of the complete anchoring assembly (See FIG. 3E). In one embodiment, the severing can be effected by the advancement of the telescoping pusher member via the depression of the second actuator 38. Alternatively, the severing action is operatively associated with the actuation of the third actuator 40. Thereafter, the second actuator 38 is released, automatically or manually, to permit the re-staging of both the first 52 and second 98 parts of the second anchoring member. That is, in one contemplated approach, members 113 and 119 are withdrawn to allow the release and deployment of the second anchoring member 52, 98 and then advanced again after the desired staging of component 52.

The present invention also contemplates a myriad of alternative embodiments of the proximal or second anchoring member. In a majority in the next presented descriptions regarding these embodiments, the second anchoring member is comprised of a first part 52 which is placed into a locking engagement with a second part 98. In doing so, the first 52 and second parts 98 are affixed to the connector 94. It is to be recognized that the first and second parts can be formed of any conventional materials such as metals or polymeric materials.

Figure 9A:
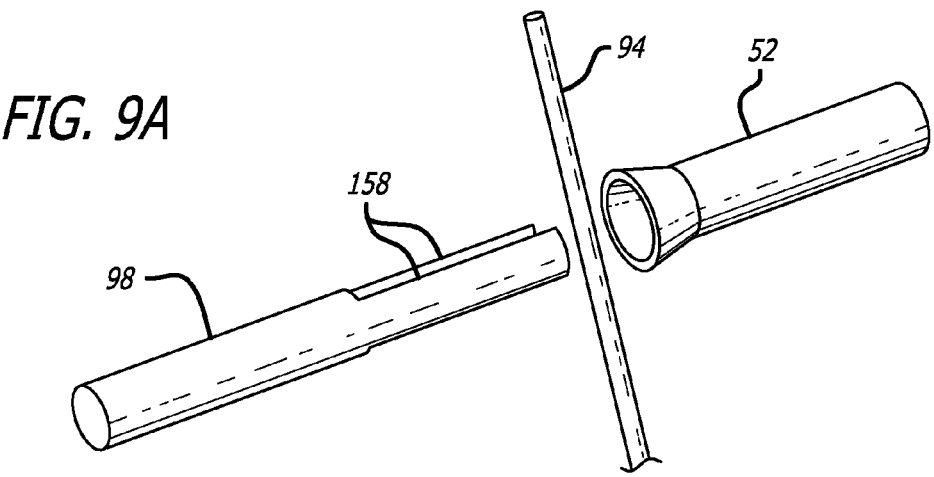
FIG. 9A is an enlarged perspective view, depicting a first step in joining the first and second components of the second anchoring member.
Figure 9B:
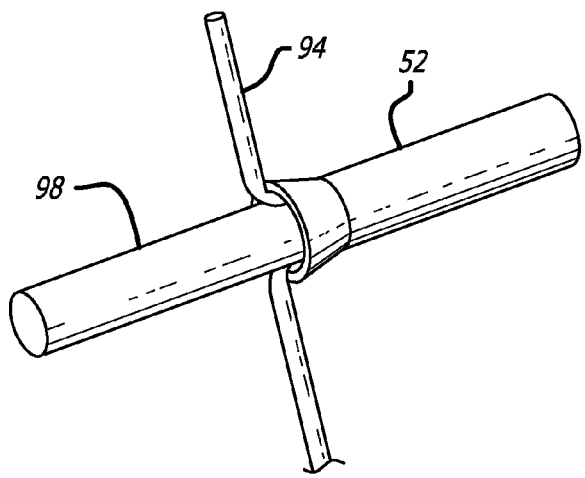
FIG. 9B is an enlarged perspective view, depicting a second step in joining the first and second components of the second anchoring member.
Figure 9C:
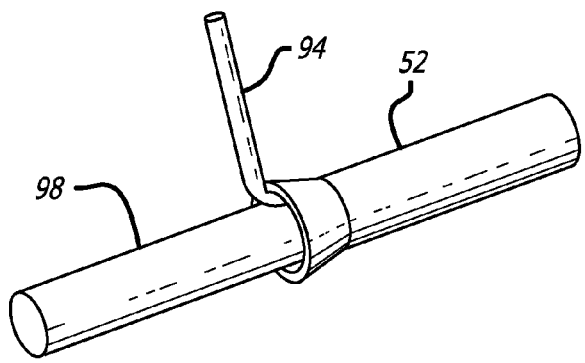
FIG. 9C is an enlarged perspective view, depicting a third step in joining the first and second components of the second anchoring member.

With reference to FIGS. 9A-C, the second anchoring member includes a generally tubular first part 52 including a slightly flared mouth configured to receive both a portion of the connector 94 and a second part 98. In this embodiment, the second part includes a pair of spaced arms 158 which capture the connector and facilitates advancing the connector within the mouth of the first part. It is contemplated that the arms 158 are spaced to an extent greater than an interior of the tubular first part 52 so that in combination with the area occupied by the connector 94, a locking engagement between the first and second parts is accomplished upon the full insertion of the second part 98 within the first part 52. Thereafter, excess connector 94 length can be cut away to form a complete second anchoring assembly.

Figure 9D:
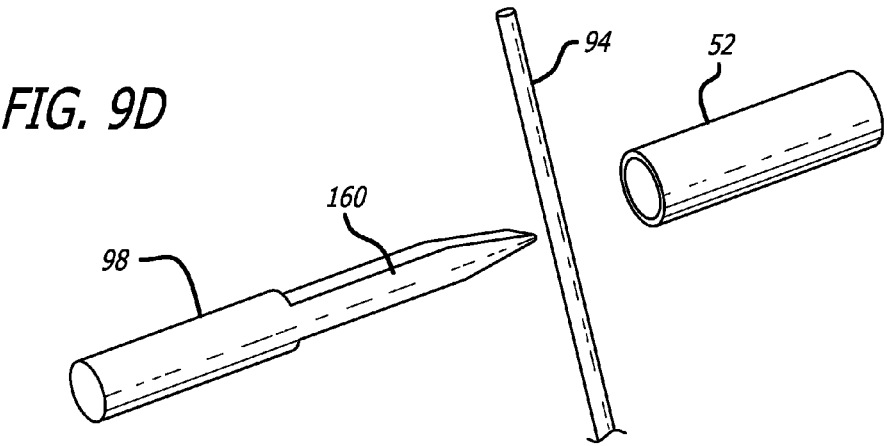
FIG. 9D is an enlarged perspective view, depicting a first step in an alternate approach in joining the first and second components of the second anchoring member.
Figure 9E:
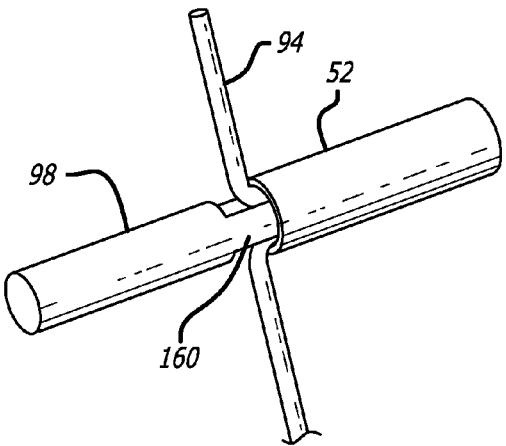
FIG. 9E is an enlarged perspective view, depicting a second step in the alternate approach in joining the first and second components of the second anchoring member.
Figure 9F:
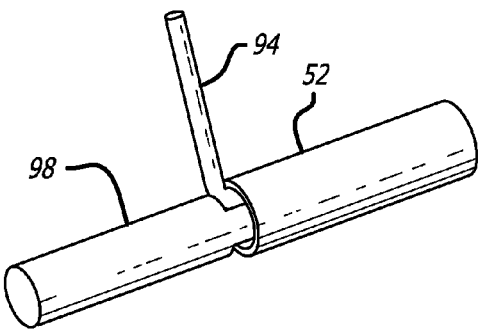
FIG. 9F is an enlarged perspective view, depicting a third step in the alternate approach in joining the first and second components of the second anchoring member.

In a slightly modified approach (FIGS. 9D-9F), the second part 98 includes a spike-like terminal end portion 160 which can be configured to engage the connector 94 and insert it within an interior of a tubular first part 52. The spike-like terminal end portion 160 defines a tapered structure, a section with an enlarging dimension of which is sized and shaped to lockingly engage with the interior of the first part 52. The completed assembly is characterized by a portion of the connector 94 retained between the first 52 and second parts 98.

Figure 9G:
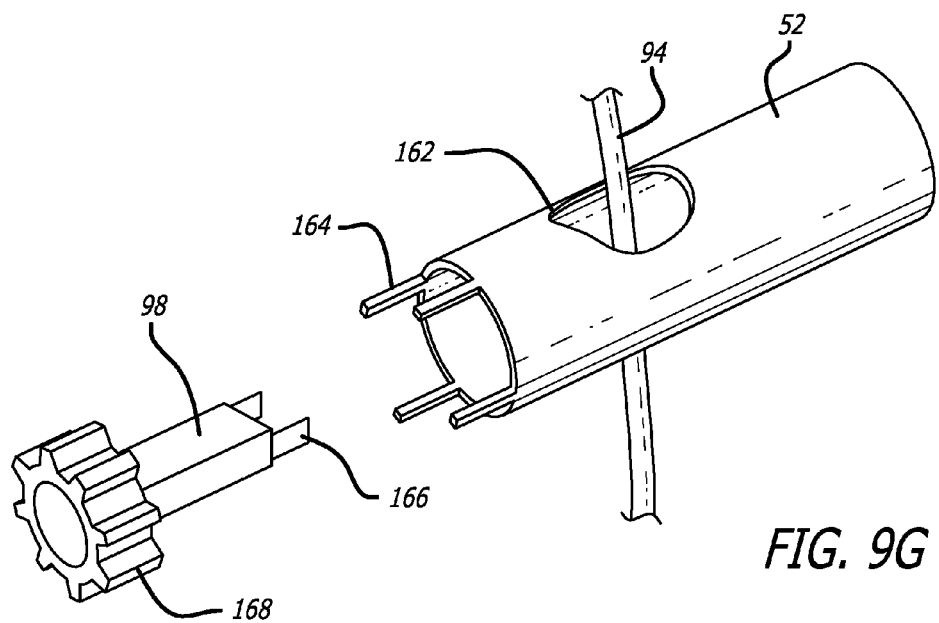
FIG. 9G is a perspective view, depicting another alternate embodiment of the first and second components of the second anchoring member.
Figure 9H:
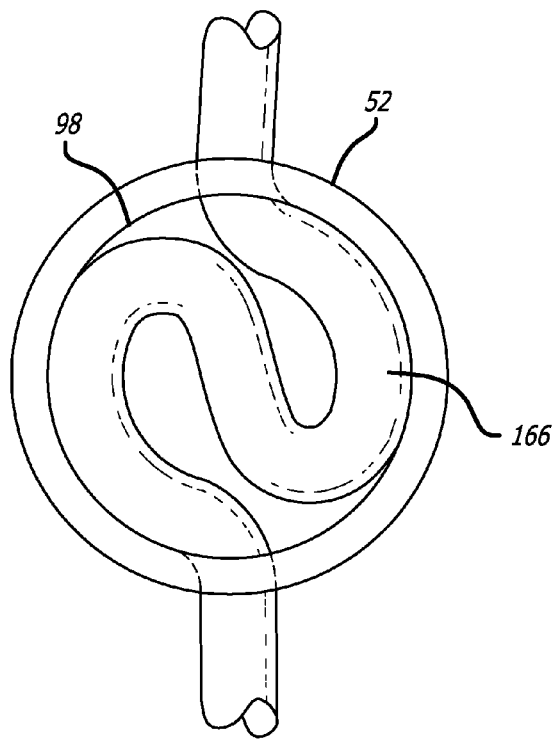
FIG. 9H is a cross-sectional view, depicting an interior of the assembly shown in FIG. 9G.

The approach depicted in FIGS. 9G and H is slightly different. The connector 94 is arranged to be threaded through a pair of oppositely arranged apertures 162 formed in a generally tubular first part 52. The first part 52 further includes a mouth equipped with a plurality of proximally oriented, radially spaced arms 164. The second part 98 also defines a generally tubular structure, one having a section with a smaller outer profile than an interior of the first part 52. The second part 98 further includes a pair of distally oriented projections 166 as well as a back end equipped with a gear-like collar 168. To accomplish a locking arrangement between the first 52 and second 98 parts, the second part 98 is inserted within the first part 52 so that the projections 166 are configured on opposite sides of the connector. The collar 168 is then used to rotate the second part 98 with respect to the first part until the connector 94 defines an S-shaped portion within an interior of the first part. The second part 98 is thereafter fully inserted into the first part, the gear-like collar being configured to register between the radially spaced arms 164 of the first part 52 to thereby lock the two parts to each other. Furthermore, it is to be recognized that these structures of the first 52 and second 98 parts can be reversed in that the first part 52 can assume the structure of the described second part and vice versa.

Figure 9I:
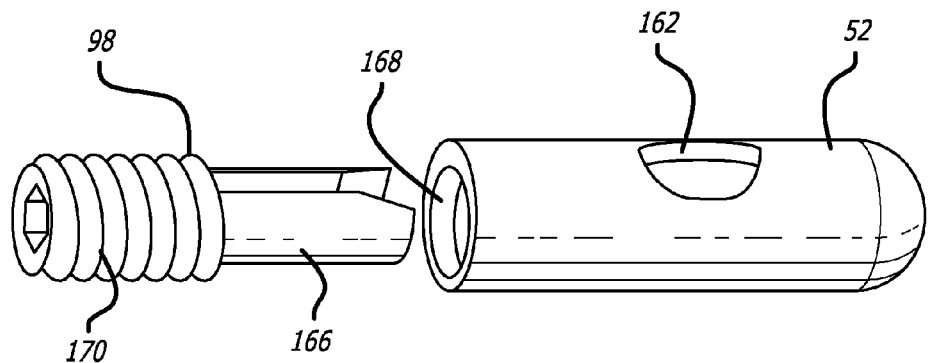
FIG. 9I is a perspective view, depicting yet another alternative embodiment of the first and second components of the second anchoring member.
Figure 9J:
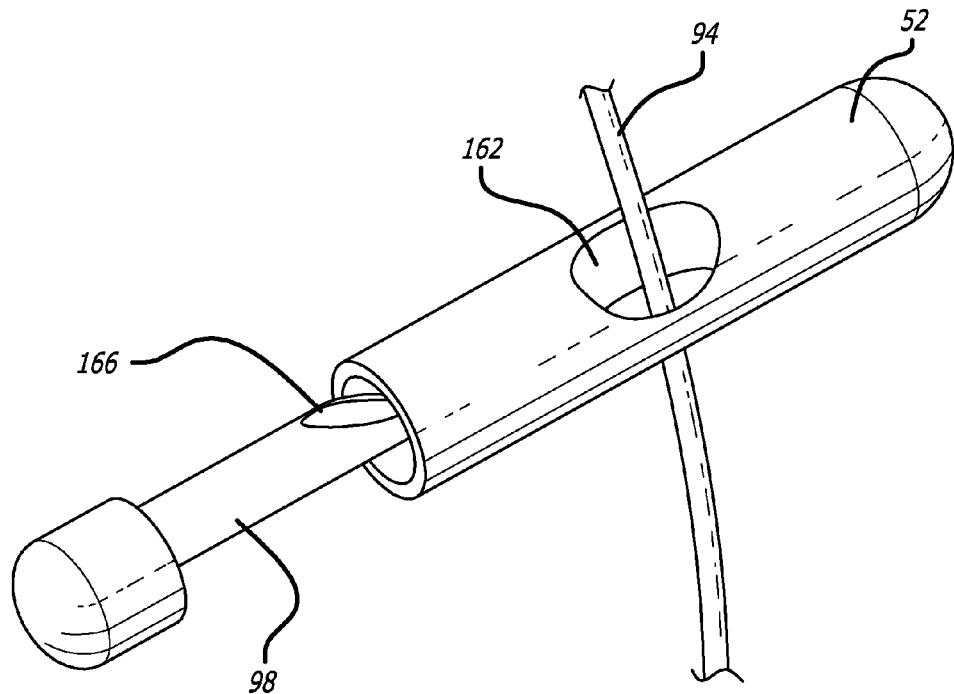
FIG. 9J is a perspective view, depicting yet another embodiment of the second anchoring member.

The embodiments depicted in FIGS. 9I and J take a similar approach to that shown in FIGS. 9G and H. That is, each take advantage of a locking engagement resulting from the rotation of one part of the second anchoring member with respect to the other. Again, each of these embodiments include a first part 52 with pair of apertures 162 through which a connector 94 is threaded. The assembly depicted in FIG. 9I includes a first part 52 configured with internal threads 168 which are complementary to external threads 170 formed on a second part 98. Thus, as the second part 98 is placed within the first part 52, it is rotated, the complementary threaded portions forming the locking engagement between the two parts. The assembly of FIG. 9J takes advantage of a second part 98 including arms 166 which are bent radially outwardly and the bent portion being sized to facilitate a locking arrangement with an interior of the first part 52. This particular approach is also characterized by the first 52 and second 98 parts having rounded terminal ends which provide an atraumatic surface which can be desirable in certain situations. Again, the structures of the first and second parts can be reversed if desired as can those of the following approaches.

Figure 9K:
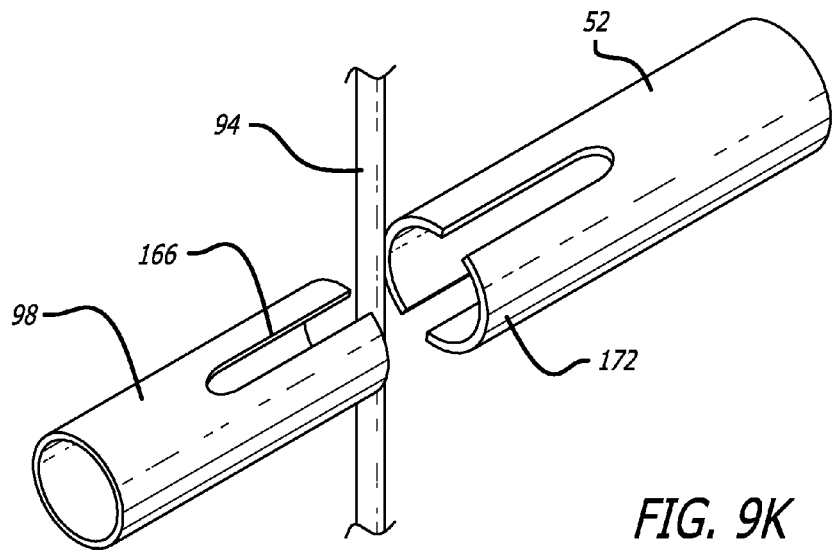
FIG. 9K is a perspective view, depicting a further embodiment of the second anchoring member.

As shown in FIG. 9K, another approach involves a first part 52 including a pair of proximally oriented projections 172 which can be formed by splitting longitudinally the mouth to the generally tubular first part 52. The connector 94 is captured between the distally oriented spaced projections 166 of the second part 98 and the proximally oriented projections 172 of the first part 52 as the second part 98 is inserted within the first part 52.

Figure 9L:
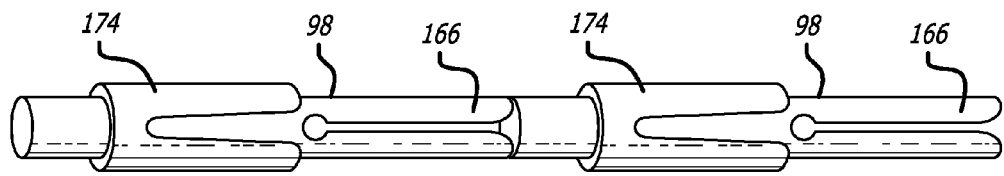
FIG. 9L is a perspective view, depicting yet a further embodiment of the second anchoring member.

In yet another approach (FIG. 9L), the second part 98 is pre-loaded with a lock ring 174, which is oriented about the second part 98 at a proximal end portion thereof. As the second part 98 is advanced over a connector and into engagement with a first part, its spaced arms 166 enter an interior of the first part. Once the second part 98 is seated within the first part, the lock ring 174 is then advanced over the second part 98 to accomplish a locking arrangement.

Figure 9M:
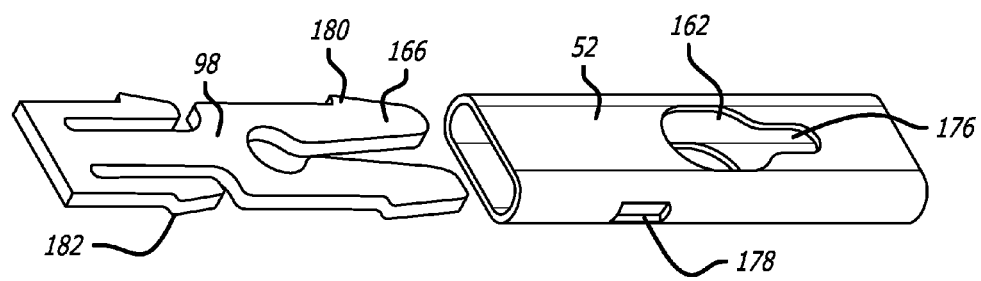
FIG. 9M is a perspective view, depicting another embodiment of the second anchoring member.

The first part 52 can also define a generally tubular member having an oval cross-sectional profile. Such a structure is depicted in FIGS. 9M and N. Further, one of the oppositely oriented apertures 162 formed in the first part 52 can further include a slotted-portion 172 sized to receive a portion of a connector after the first part 52 is placed in a locking arrangement with the second part 98. The first part 52 further includes a pair of openings 178 configured on opposite lateral sides of the device. In these embodiments, the second part 98 defines a relatively flat member, the distally oriented arms 166 of which include projections 180 having a ramped portion. Although different structure is employed, both embodiments of the second part 98 further include a second pair of projections 182 formed at proximal end portions of the respective devices. As the second parts 98 of these approaches is advanced within the first part 52, the first projections 180 act to compress the arms together then are advanced past the lateral apertures 178 of the first part 52 and are configured beyond a distal end (not shown) of the first part 52. Once the second part 98 is fully inserted in the first part 52, the second pair of projections 182 register within the lateral openings 178 formed in the first part 52, thus forming a locking engagement.

The first part 52 can also be formed form a member having a deformable, enlarged mid-section 184 (See FIGS. 9O and P). In one approach, the enlarged mid-section 184 can be formed by longitudinally cutting a portion of the first part 52 and separating the material forming this portion to define the opening 162 which is as before, intended to receive a portion of the connector. As the second part 98 in the form of a generally tubular sleeve is advanced over the first part 52, the mid-section 184 is compressed, such compression effecting a locking engagement between the first and second parts.

The second part 98 (See FIGS. 9Q and R) can also include laterally spaced tabs 180 which slide within an interior of a generally tubular first part 52. The spaced areas 166 capture a portion of the connector 94. Once the second part 98 is fully inserted within the first part 52, the laterally spaced tabs lock in place outside a proximal end of the first part 52. In the process, the portion of the connector 94 captured by the arms 166 is compressed and held in place between the first 52 and second parts 98.

Turning now to FIGS. 9S-U, further approaches to accomplishing a locking arrangement between first 52 and second 98 parts are presented. The embodiment of FIG. 9S is characterized by a first part having a generally oval cross-sectional profile and including both the first lateral apertures 178 as well as a pair of oppositely oriented, second lateral apertures 186. The second part is a generally flat member characterized by a proximal end configured with a stop in the form of a T-bar 184. As the second part 98 is advanced within the first part 52 (not shown), the tabs 180 formed on the second part first register within the first lateral openings 178. Thereafter, the second part is further inserted within the first part 52 to capture the connector which is threaded through the apertures 162 formed in the first part 52. Yet further advancement of the second part 98 configure the detents 180 within the second lateral openings 186 of the first part 52. The proximal stop 188 is at this time placed in apposition with a proximal end of the first part.

In a similar approach (See FIGS. 9T-U), the generally flat second part 98 includes both the first 180 and second 182 tab structures. As the second part 98 is advanced within the first part 52, the first tabs 180 initially register within lateral openings 178 of the first part 52, which can act as a staging for subsequent advancement and capture of a connector. Upon such subsequent advancement, the first tabs 180 are held within an interior of the first part 52 and the second tabs 182 register within the lateral openings 178 of the first part 52.

Figure 9V:
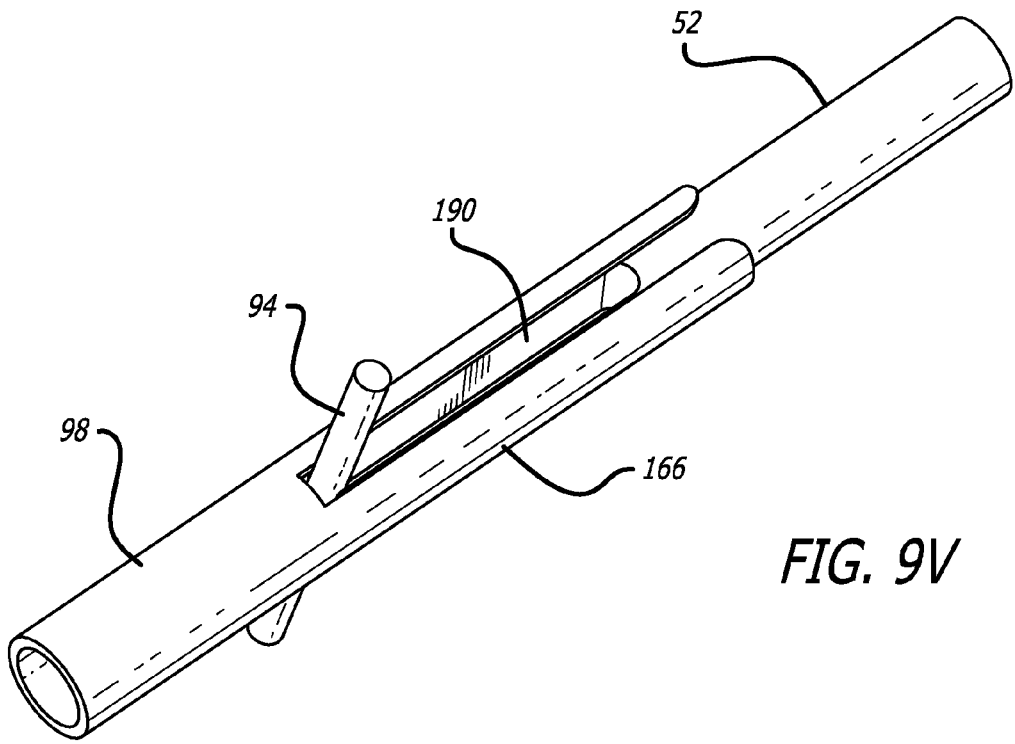
FIG. 9V is a perspective view, depicting another embodiment of the second anchoring member.
Figure 9W:
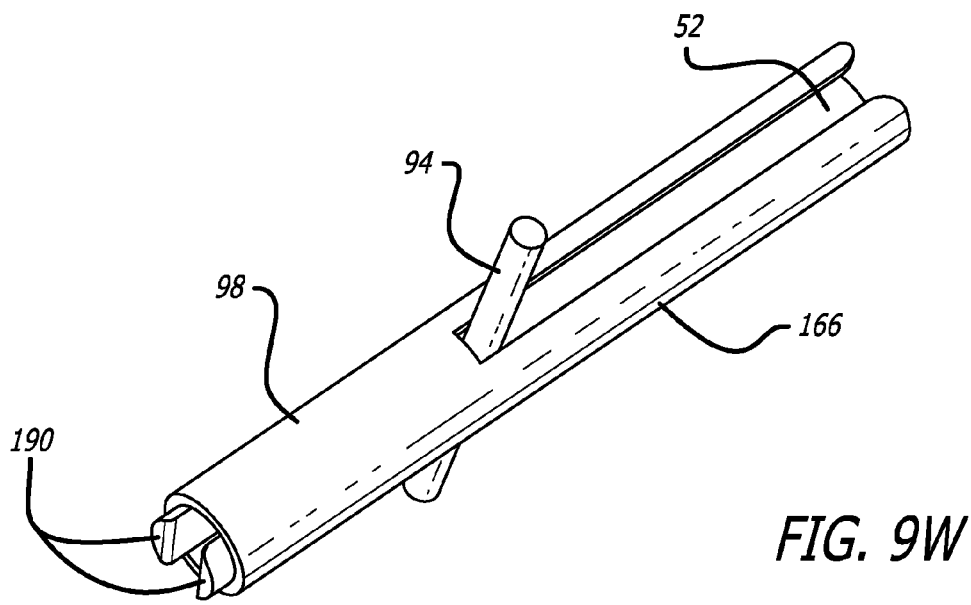
FIG. 9W is a perspective view, depicting the embodiment of FIG. 9V in an assembled form.

As shown in FIGS. 9V and W, the first part 52 can also assume a pin-like structure with spaced arms 190. The second part 98 can define a generally tubular structure including distally oriented arms 166. Insertion of the first part 52 within the second part 98 causes the spaced arms 190 of the first part 52 to compress about a portion of a connector to form a locking arrangement. It is to be recognized that this approach to a locking arrangement can be modified in principle, in that, as stated above, the structures of the first 52 and second 98 parts can be reversed.

Figure 9X:
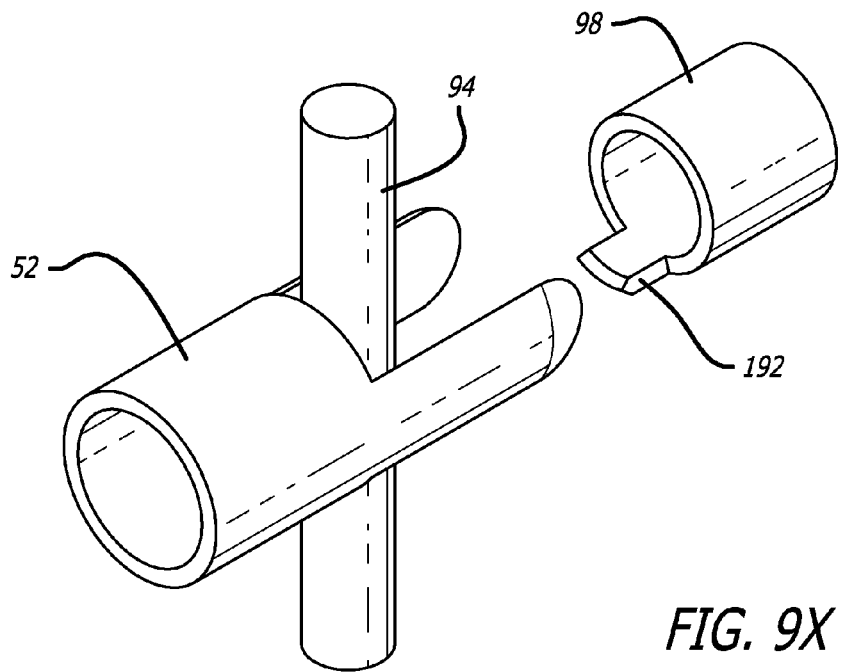
FIG. 9X is a perspective view, depicting another embodiment of the second anchoring member.

Moreover, the second part 98 can assume a generally tubular structure including a cutting projection 192 (See FIG. 9X) arranged to engage a connector 94 upon insertion of the first part 52 within the second part 98. In this way, further action beyond placing the first 52 and second 98 parts into locking engagement, is not required to sever the connector 94. Again, it is to be recognized that the structures of the first 52 and second 98 parts can be reversed to also take advantage of this approach.

Figure 9Y:
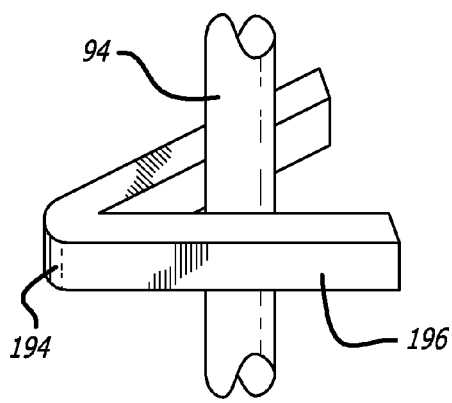
FIG. 9Y is a perspective view, depicting another embodiment of the second anchoring member.
Figure 9Z:
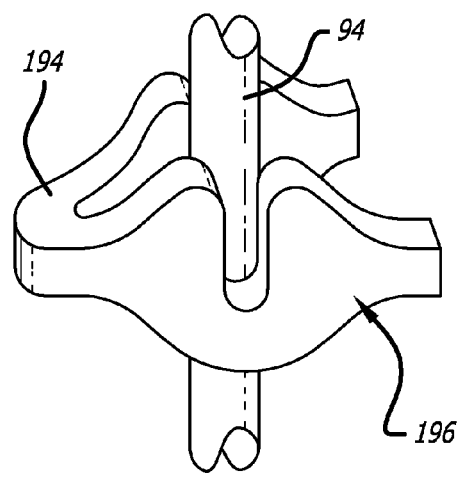
FIG. 9Z is a perspective view, depicting another embodiment of the second anchoring member.
Figure 9A:
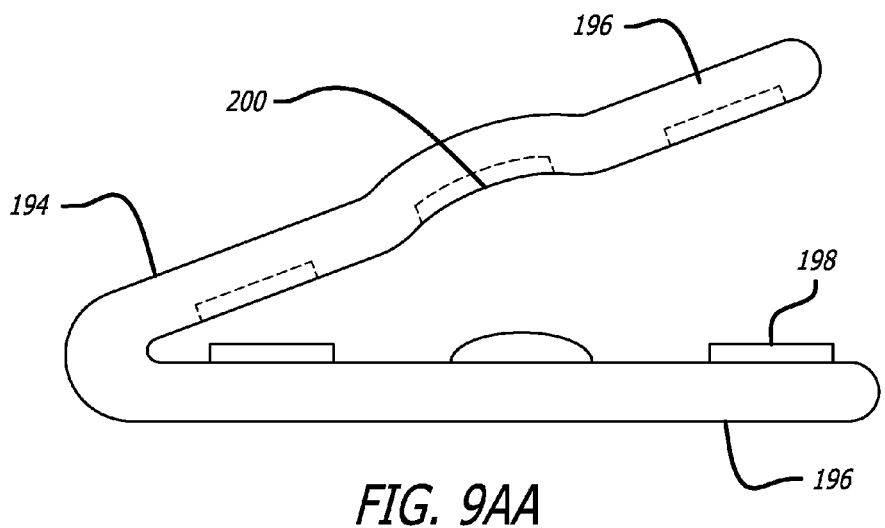
Figure 9A:
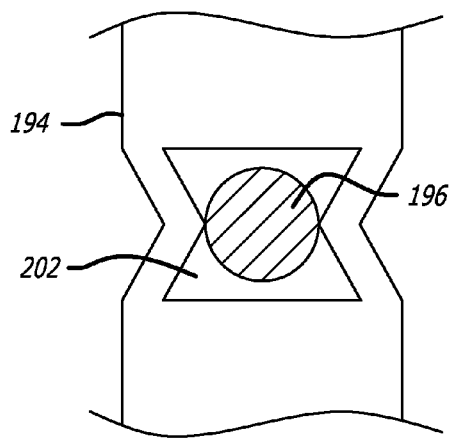
Figure 9A:
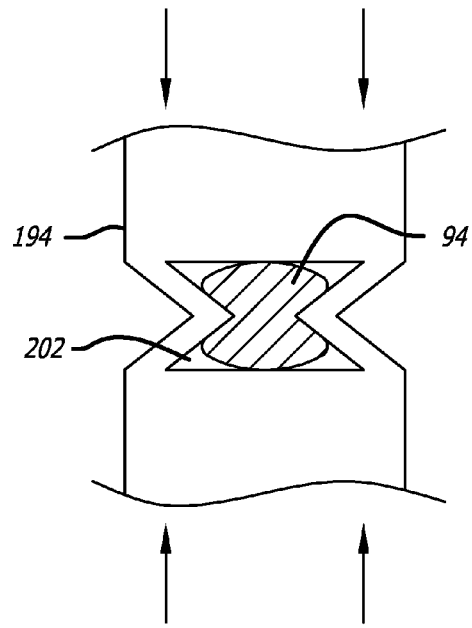
Figure 9A:
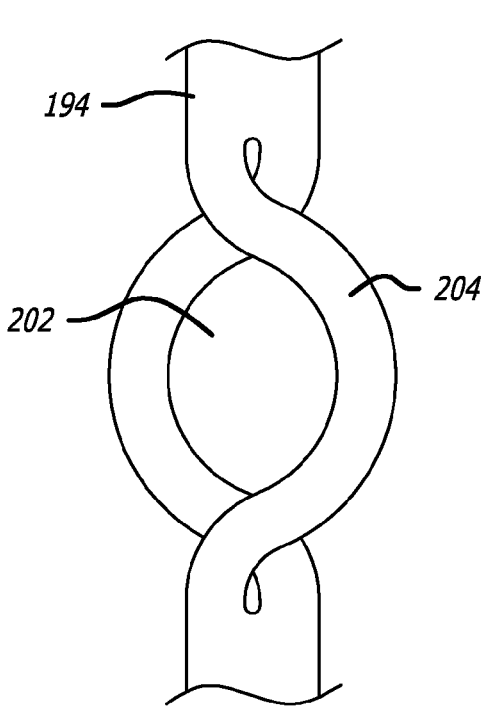
Figure 9A:
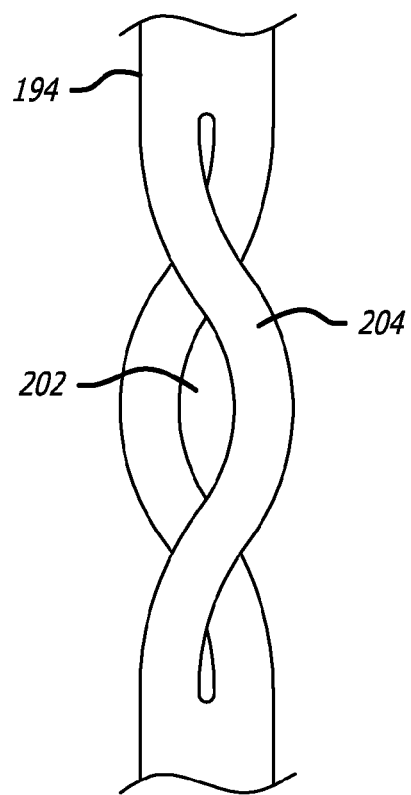
Figure 9A:
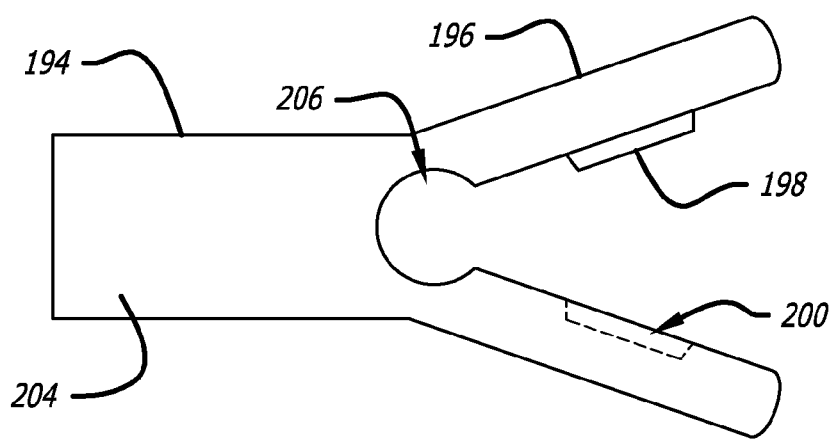
Figure 9A:
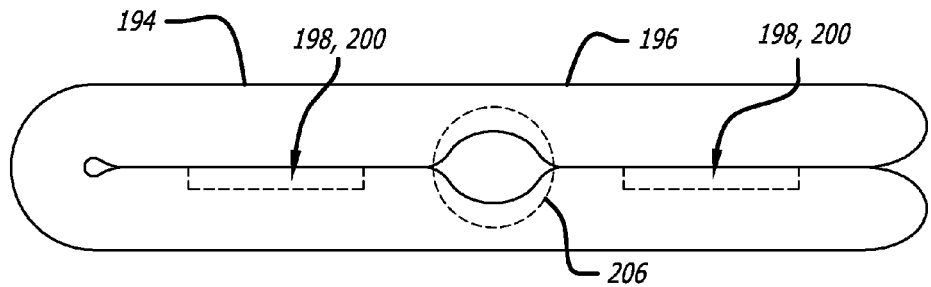
Figure 9A:
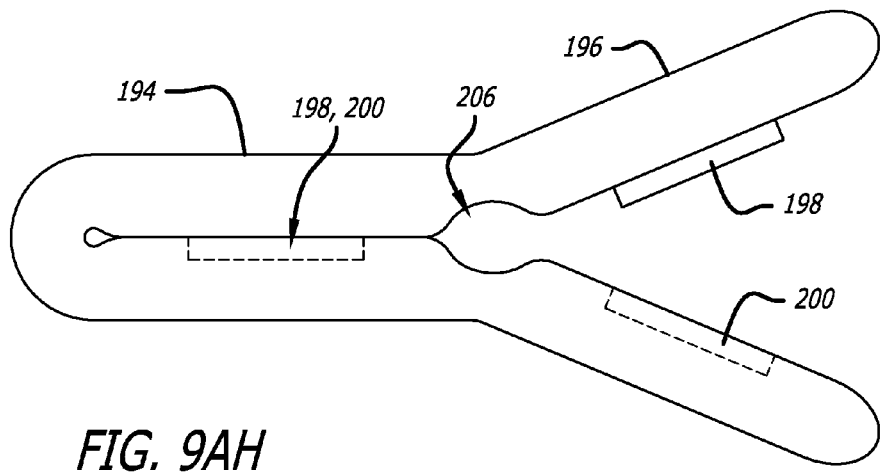
Figure 9A:
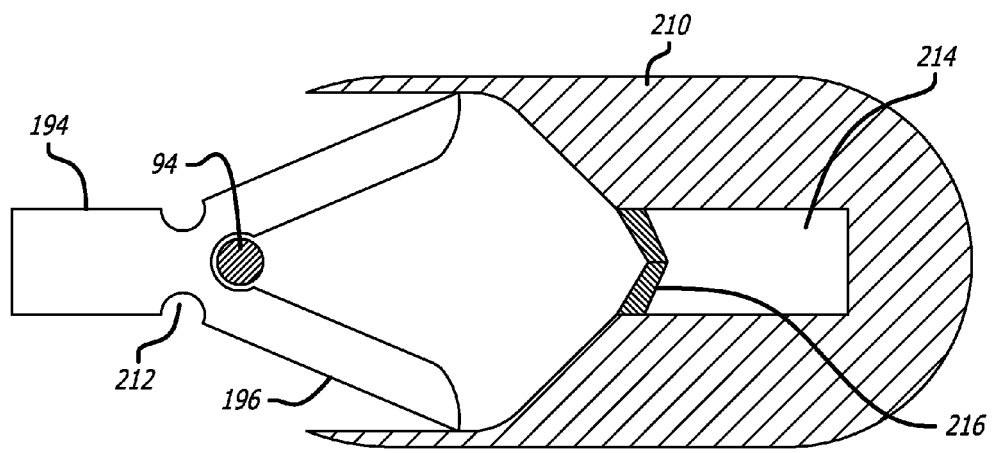
Figure 9A:
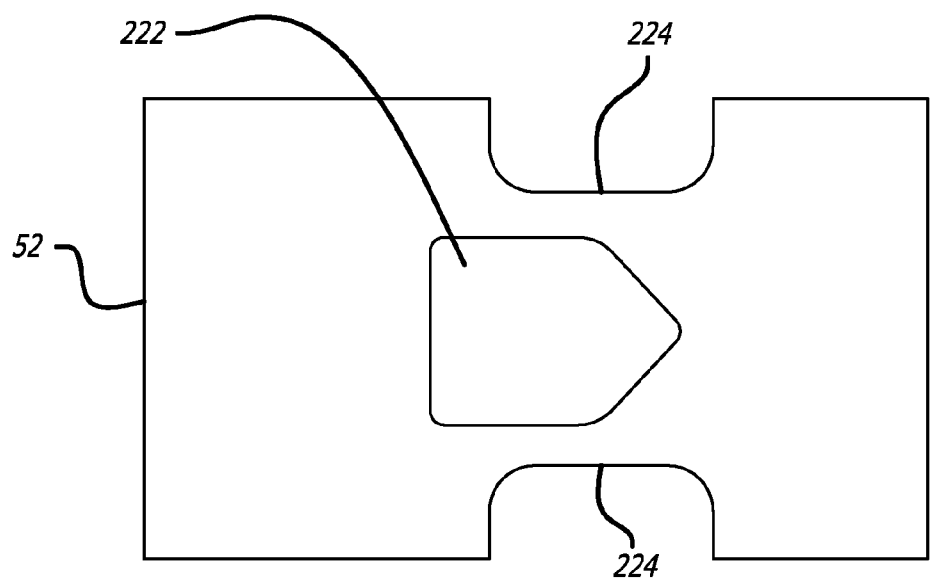
Figure 9A:
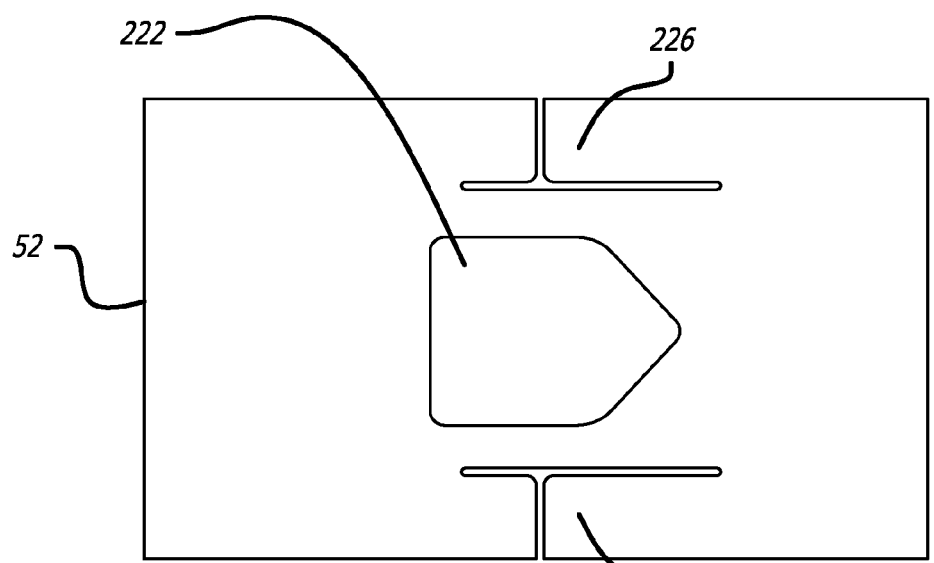

In a number of related approaches (See FIGS. 9Y-9AH), the second anchoring component can be formed of a single integral locking member 194. Certain of these members 194 are intended to be formed of plastically deformable material so that it can first assume a generally open configuration and then be deformed to define a closed position in a locking arrangement about a connector member. Alternatively, these members 194 can be formed of resilient material and be first held open and then allowed to self-collapse about a connector. In one such locking member (FIG. 9Y), the integral member 194 is generally V-shaped and includes a pair of diverging arms 198 which can be arranged into locking contact with a connector 194. Another locking member 194 (FIG. 9Z) is characterized by a clam shell profile, an interior of the arms 196 of which is suited to lock with a portion of a connector 94. The locking member 194 of FIG. 9AA is also generally V-shaped and further includes a pair of diverging arms 196, one of which includes bosses 198 designed to mate with recesses 200. A center section of one arm 196 is bent to provide space to receive a connector.

In FIGS. 9AB-AC, there is shown a plastically deformable locking member 194 that is configured with a collapsible aperture 202. In an undeformed configuration, the aperture 202 is formed by walls defining a generally hour glass shape. Applying a longitudinal compression force to the locking member 194 causes the aperture 202 to collapse about and lock with a portion of a connector 94, the walls deforming inwardly and engaging the connector 94.

The locking member 194 can also be embodied in a device including a mid-section characterized by helically arranged members 204 (See FIGS. 9AD-AE). The opening 202 defined by the helical member 204 is sized to receive a connector member. This device can either be formed of plastically or elastically deformable materials such that collapsing the opening 202 about a connector can be accomplished through the application of a force to the locking member 194 or by removing a compression force from the member.

In still yet other approaches (FIGS. 9AF-9AH), the locking member 194 can be embodied in a member including diverging arms 196 projecting from a cylindrical base 204. One arm includes a boss or raised portion 198 sized to fit within a recess 200. A mid-section of the device further includes a generally circular space 206 defined by semi-circular cutouts formed in the opposing arms 196. This space is sized to lockingly engage a connector when the arms 196 are in a closed configuration. The locking member 194 of FIGS. 9AG-AH also includes this circular space 206 defined by semi-circular cutouts formed in the diverging opposing arms 196 as well as the locking projections 198. However, rather than the cylindrical base 204 of the embodiment of FIG. 9AF, the arms 196 and the locking member 194 extend proximally beyond the circular space 206. This portion of the arms 196 also include a complementary projection 198 and recess 200 arrangement.

In a related approach (See FIG. 9AI), the locking member 194 can be deformed about a connector 94 employing an anvil 210. Such an anvil custom designed for the various approaches can be employed to deform the previous disclosed embodiments of other members. As the locking member 194 is advanced within the anvil, angled surfaces within an interior of the anvil operate to close the arms 196 of the locking member 194. Narrowed portions 212 of the locking member facilitate such closing of the arms about a portion of the connector 94. Once the arms are inserted into an interior cavity 214 of the anvil 210, a cutting blade 216 severs the connector 94 to length as desired.

Turning now to FIGS. 9AJ-K, further embodiments of a second anchoring member including a first part 52 and a second part 98 are presented.

In these approaches, the second part 98 includes arms 196 which are biased to an open configuration. Using an anvil 210 housing a first part 52 in the interior cavity 214, the second part 98 is caused to be inserted and held within the first part 52. In a first embodiment (FIG. 9AJ), the arms 196 of the second part 98 are relatively long compared to those of a second embodiment (FIG. 9AK). In both approaches, however, a generally tubular first part 52 retains the arms 196 in a closed position in locking engagement about the connector 94.

Returning to the concept of a second anchoring member defining a locking member 194 (See FIGS. 9AL-AM), in still yet another approach the capturing of the connector can be accomplished using a clip-like structure. A pair of arms 196 begin at a proximal end of the device in a spaced arrangement. As the arms extend distally, they cross at mid-point 218 beyond which a distal portion of the arms are adjacently arranged in apposition. One or both arms 196 can include a recess providing a space to allow the arms 196 to cross at the mid-point 218. Applying a force to the proximal, spaced portion of the arms 196 causes the distal portion of the arms 196 to open. When opened, the arms 196 can be configured to receive a connector. A closing force between the distal portion of the arms 196 of the locking member 194 accomplish locking the structure on a connector.

The first part 52 of the second anchoring member can also be configured from a flat sheet of material into which a pattern is cut to form various slots and tabs (See FIGS. 9AN-AO). These first parts 52 can be formed of material which is capable of self-forming from the flat configuration into a generally tubular configuration when unconstrained. For example, material such as nitinol which has memory properties can be used to form such structure. A first contemplated flat pattern (See FIG. 9AN) includes a central five sided aperture 222 on either side of which are configured slots 224 cut in from lateral side edges of the structure. In a second pattern (FIG. 9AO), the lateral slots 222 are replaced with cutouts which define tabs 226.

Figure 10A:
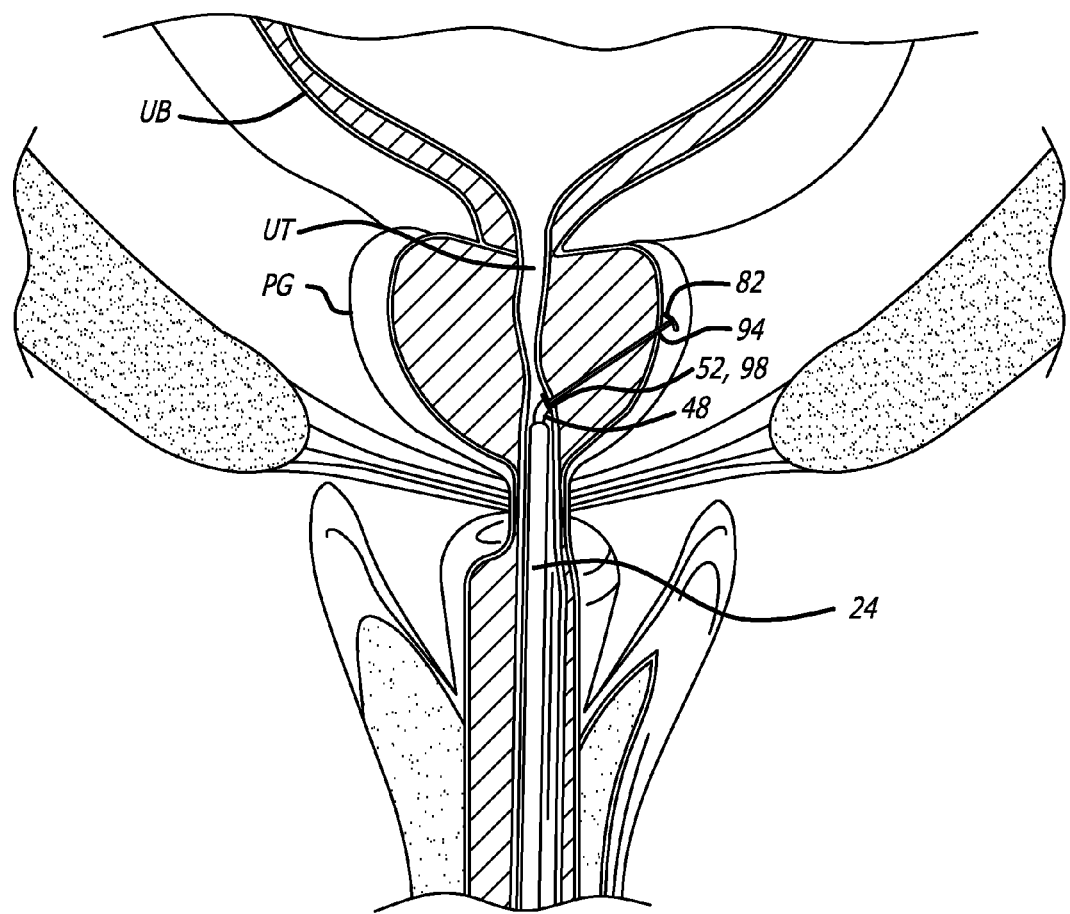
FIGS. 10A-B are cross-sectional views, depicting yet further steps involved in treating a prostate gland using the present invention.
Figure 10B:
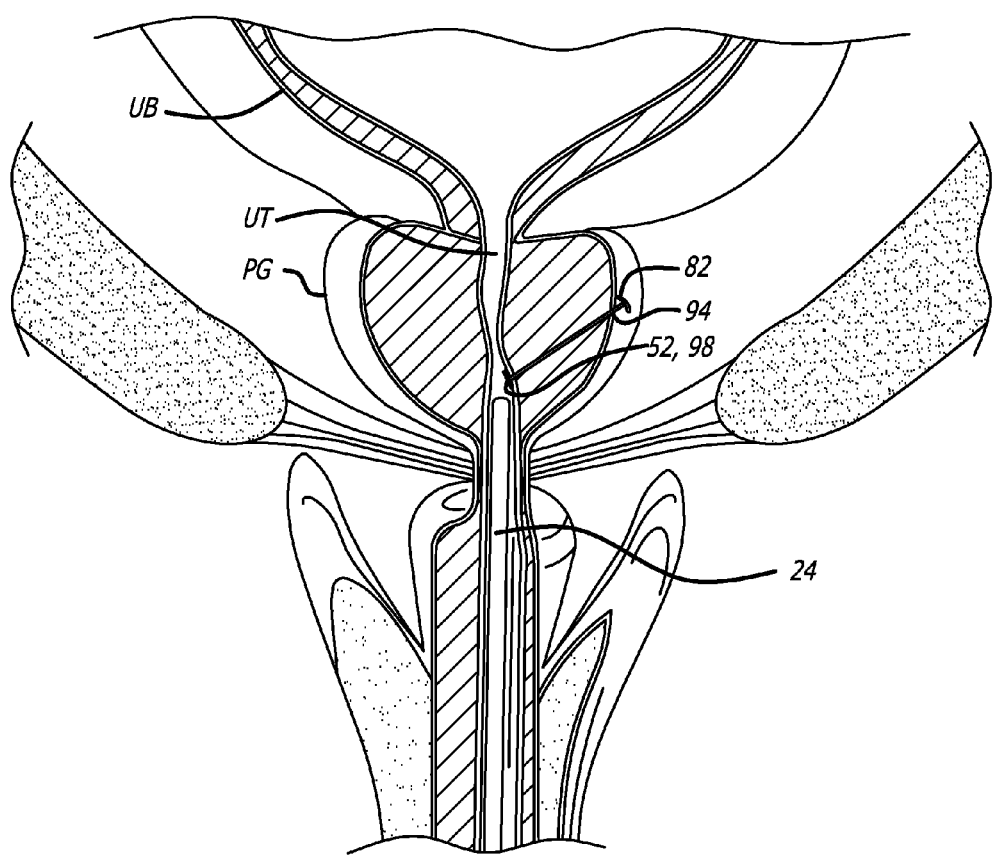

Irrespective of the specific form of the anchoring assembly, a next step in the context of prostate treatment involves positioning the proximal anchor assembly 52, for example, within a desired section of the urethra (UT) of the patient (See FIG. 10A). Prior to doing so, the patient can be monitored to determine whether there has been any evidence of improvement through the placement of the anchor. One such symptom is whether there has been any urination. After so checking, the proximal anchor assembly 52 can be implanted. The patient is the again checked for evidence of improvement (i.e., flow improvement, visual appearance, opening of the urethra, urination, etc.). Next, the connector 94 is severed and the integrated anchor delivery device is withdrawn (See FIG. 10B) and ultimately removed from the patient's body.

Accordingly, the present invention contemplates both pushing directly on anchor portions of an anchoring assembly as well as pushing directly upon the connector of the anchor assembly. Moreover, as presented above, the distal or first anchoring component is advanced and deployed through a needle assembly and at least one component of the proximal or second anchoring component is advanced and deployed through a generally tubular potion of the anchor deployment device. Further, both a single anchor assembly or multiple anchor assemblies can be delivered and deployed at an intervention site by the deployment device. Consequently, in the context of prostate treatment, the present invention accomplishes the compression of both the urethra and prostate gland, the delivering of an implant at the interventional site, applying tension between ends of the implant, and the invagination of the implant within natural tissue. Moreover, drug delivery is both contemplated and described as a further remedy in BPH in treatment.

Figure 11A:
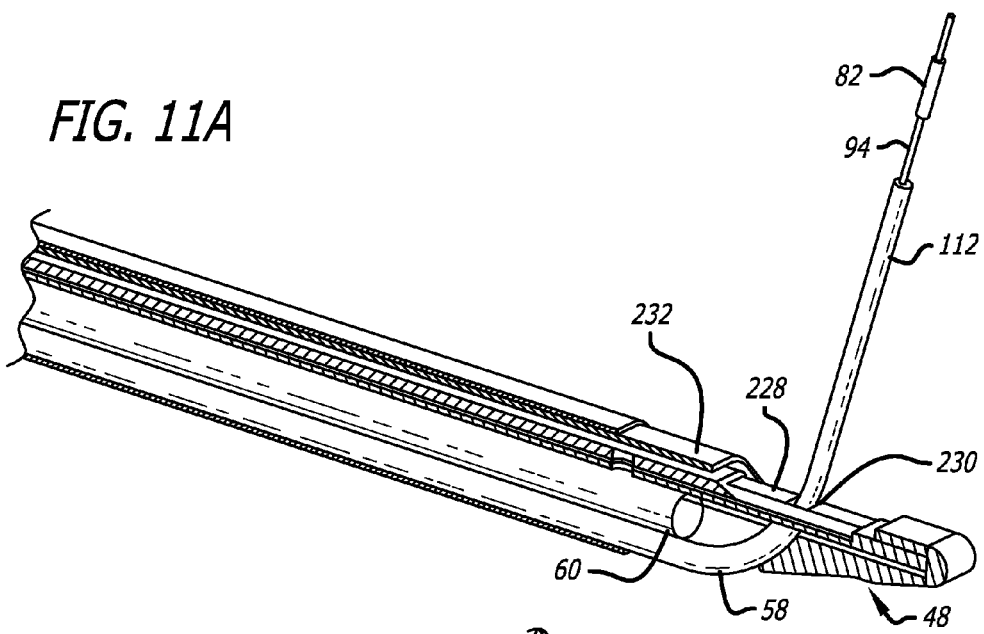
FIG. 11A is a cross-sectional view, depicting a first step in an alternative approach to anchor assembly and deployment.
Figure 11B:
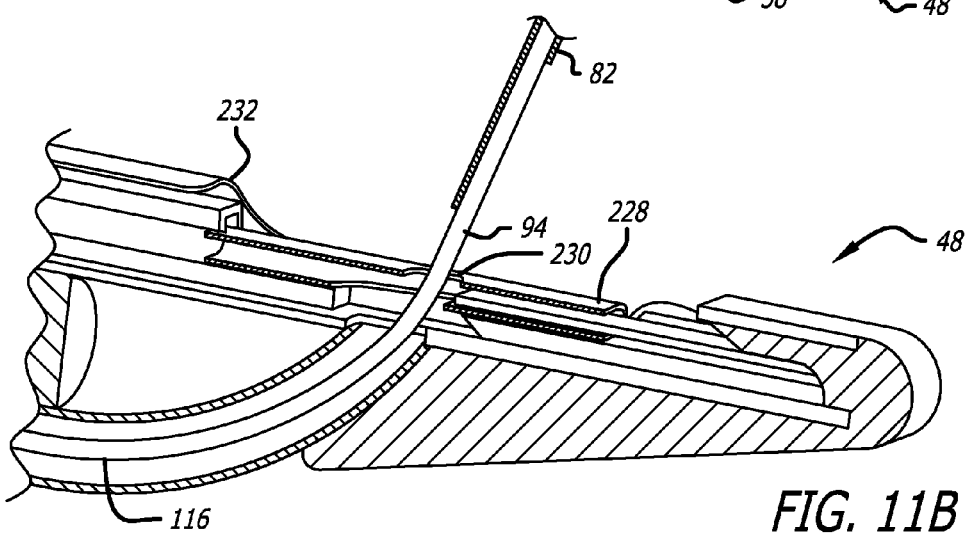
FIG. 11B is a cross-sectional view, depicting a second step in an alternative approach to anchor assembly and deployment.
Figure 11C:
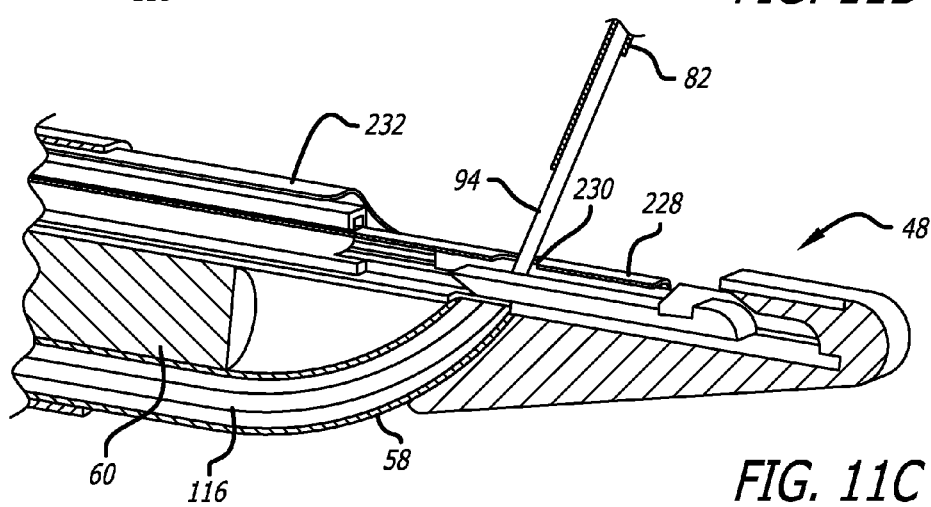
FIG. 11C is a cross-sectional view, depicting a third step in an alternative approach to anchor assembly and deployment.

An alternate embodiment of a distal portion of an anchor delivery device is shown in FIGS. 11A-C. FIG. 11A depicts the device in a stage of operation where the needle assembly 112 has been extended through the needle housing 60 and configured to project laterally from a distal end portion 48 of the device and is in the process of being withdrawn over the connector 94 and first anchor member 82 assembly. FIG. 11B shows the position of the pusher assembly 116 once the needle assembly has been fully retracted within the needle housing 58. A retractable cover 228 shown in its advanced position includes a side aperture 230 through which the needle 112 and pusher 116 assemblies can be advanced to thereby place the connector 94 in a position for engagement by first and second 98 parts of the second anchoring member. To effect longitudinal movement of the cover 228, a sliding arm 232 is provided and placed into engagement with the cover. The sliding arm 232, in turn, is operatively associated with an actuator (not shown) pivotably attached to a device handle. In a further step of use (See FIG. 11C), the connector 94 is severed and equipped at its proximal end with one embodiment of a second anchoring member assembly.

Figure 12A:
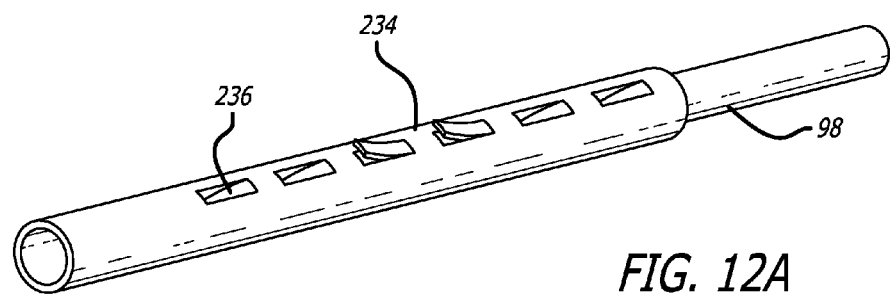
FIG. 12A is a perspective view, depicting structure configured to align components of the anchoring assembly.
Figure 12B:
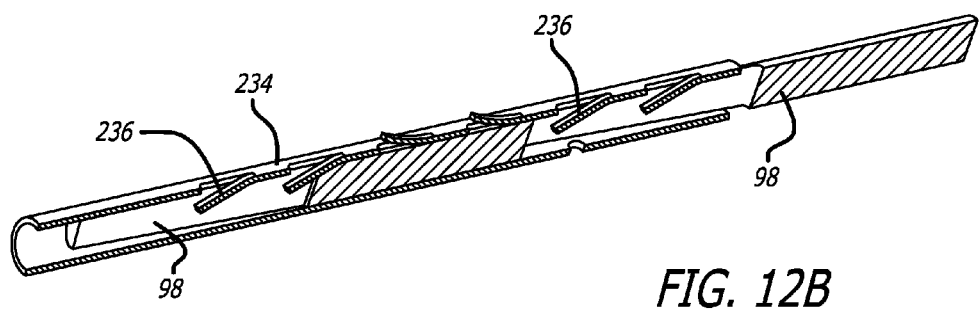
FIG. 12B is a cross-sectional view, depicting the structure of FIG. 12A.

In one particular approach (See FIGS. 12A-B), the delivery device can be equipped with an alignment tube 234 including inwardly directed tabs 236 sized and shaped to be received into complementary recesses formed in second parts 98 of a second or proximal anchoring assembly. Such tabs 230 not only provide structure for advancing the second parts 98 but it also ensures proper rotational alignment of the second part 98 as they are advanced to receive a portion of the connector and to lockingly engage with a first part of the second anchoring assembly.

Figure 13A:
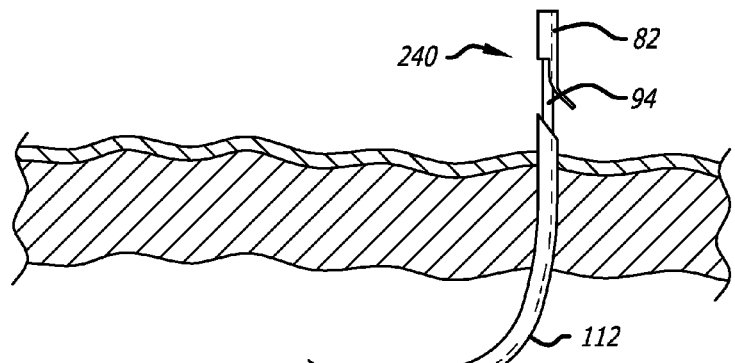
FIG. 13A is a partial cross-sectional view, depicting a first step in an alternative approach to implanting an integrated anchor assembly.
Figure 13B:
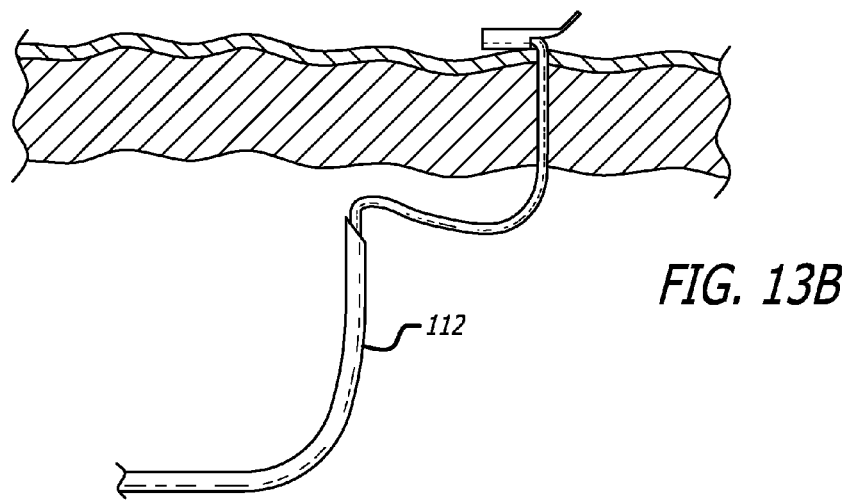
FIG. 13B is a partial cross-sectional view, depicting a second step in an alternative approach to implanting the integrated anchor assembly of FIG. 13A.
Figure 13C:
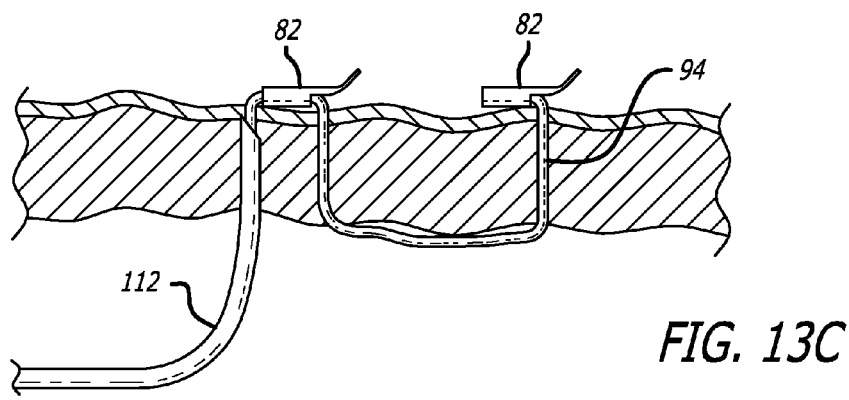
FIG. 13C is a perspective view, depicting a third step in an alternative approach to implanting the integrated anchor assembly of FIG. 13A.

With reference to FIGS. 13A-C, an integrated anchor 240 including a plurality of anchors 82 attached to each other by a connector 94 can also be used to manipulate anatomical structures. In this approach, a needle assembly 112 is utilized in a sewing motion to place various portions of the integrated anchor 240 on opposite sides of anatomical structures to accomplish the desired manipulation at an interventional site.

Figure 13D:
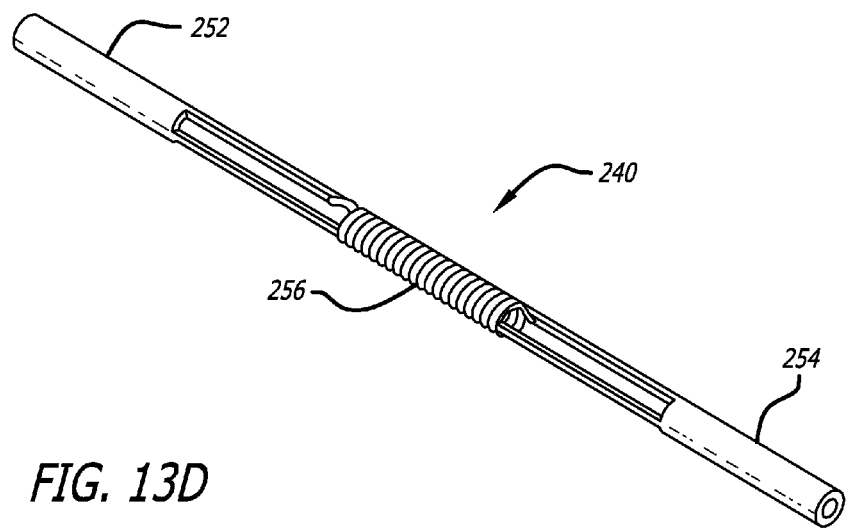
FIG. 13D is a perspective view, depicting yet another embodiment of an integrated anchor.
Figure 13E:
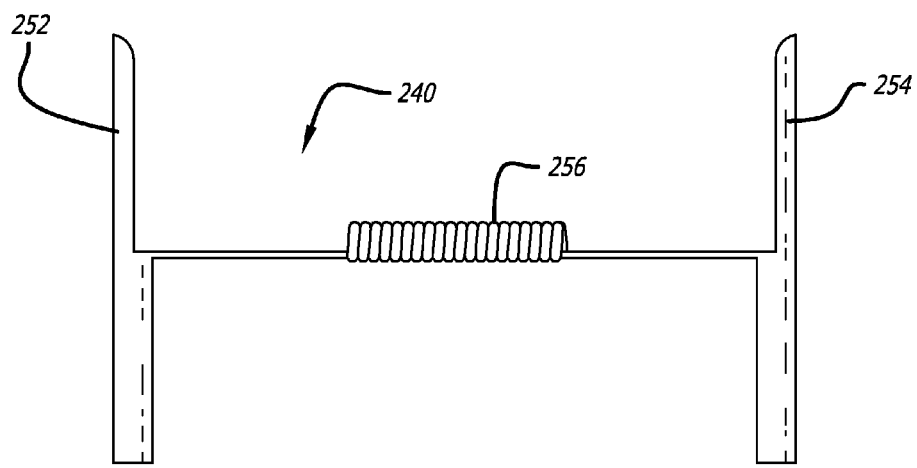
FIG. 13E is an elevation view, depicting the anchor of FIG. 13D in a flipped configuration.
Figure 13F:
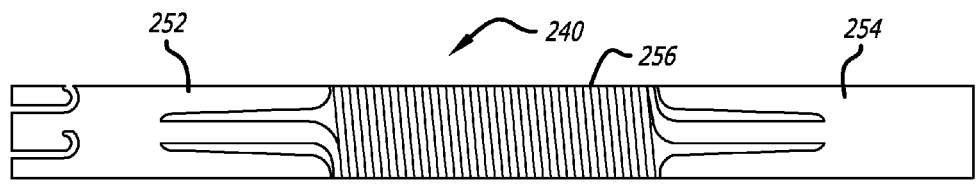
FIG. 13F is an elevation view, depicting the anchor of FIG. 13D in a flat configuration.

The integrated anchor 240 can also be cut from a pattern (FIG. 13F) to form a device which can assume a generally straight tubular configuration (FIG. 13D) for delivery to an interventional site. Once at the site, the device can be permitted to deform a generally H-shape (FIG. 13E), a first portion 252 being placed in apposition with a first anatomical structure and a second portion 254 configured against a second anatomical structure. A mid-section of the device can include a spring-like structure 256 which is particularly suited for applying a tension to the first 252 and second 254 portions.

It is to be recognized that various materials are contemplated for manufacturing the disclosed devices. Moreover, one or more components such as distal anchor, proximal anchor, connector, of the one or more anchoring devices disclosed herein may be designed to be completely or partially biodegradable or biofragmentable.

Moreover, as stated, the devices and methods disclosed herein may be used to treat a variety of pathologies in a variety of tubular organs or organs comprising a cavity or a wall. Examples of such organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. An anchor delivery apparatus, comprising: a handle assemble; a plurality of anchor assemblies, each anchor assembly comprising a ring component and a second component; and an elongate member extending from the handle assembly, the elongate member including a feeder assembly configured to releasably retain a plurality of ring components of the anchor assembly; wherein the feeder includes a biasing member that biases the ring components into a position for assembly with the second components of the anchor assembly.

2. The apparatus of claim 1, wherein the plurality of ring components are stacked vertically.

3. The apparatus of claim 2, wherein the biasing member is positioned beneath the vertically stacked ring components.

4. The apparatus of claim 3, wherein the feeder forms a distal end portion of the elongate member.

5. The apparatus of claim 4, wherein the distal end portion is shaped to accomplish testing the position of the ring component prior to releasing the ring component from the anchor delivery apparatus.

6. The apparatus of claim 3, wherein the biasing member is a leaf spring.

7. The apparatus of claim 1, wherein the anchor delivery apparatus further includes a needle assembly having a terminal end and the anchor delivery apparatus is configured to deliver first and second components of an anchor assembly.

8. The apparatus of claim 7, wherein the first component is positioned distal to the terminal end of the needle and the second component is positioned proximal to the terminal end of the needle.

9. The apparatus of claim 1, wherein the anchor delivery apparatus includes structure housing a pin component sized to mate with the ring component and an assembly that accomplishes the in-line delivery of the pin into engagement with the ring component.

* * * * *